United States Patent
Palomo Nicolau et al.

(10) Patent No.: US 9,284,296 B2
(45) Date of Patent: Mar. 15, 2016

(54) BIPYRIDINE SULFONAMIDE DERIVATIVES FOR THE TREATMENT OF NEURODEGENERATIVE DISEASES OR CONDITIONS

(75) Inventors: Francisco Palomo Nicolau, Tres Cantos (ES); Jorge Sánchez-Quesada, Tres Cantos (ES); Javier López Ogalla, Tres Cantos (ES); Félix Hernández Juan, Tres Cantos (ES); Javier Villasante Prieto, Tres Cantos (ES); Miguel Medina Padilla, Tres Cantos (ES); Ana Fuertes Huerta, Tres Cantos (ES); Juan Manuel Dominguez Correa, Tres Cantos (ES); Susana Herrero Santos, Tres Cantos (ES); Mercedes Alonso Cascón, Tres Cantos (ES)

(73) Assignee: AUBERGINE PHARMACEUTICALS LLC, Bannockburn, IL (US)

( * ) Notice: Subject to any disclaimer, the term of this patent is extended or adjusted under 35 U.S.C. 154(b) by 245 days.

(21) Appl. No.: 13/988,722

(22) PCT Filed: Nov. 21, 2011

(86) PCT No.: PCT/EP2011/070593
§ 371 (c)(1),
(2), (4) Date: Sep. 3, 2013

(87) PCT Pub. No.: WO2012/069428
PCT Pub. Date: May 31, 2012

(65) Prior Publication Data
US 2014/0005195 A1    Jan. 2, 2014

(30) Foreign Application Priority Data

Nov. 22, 2010 (EP) .................................. 10382308

(51) Int. Cl.
| C07D 513/04 | (2006.01) |
|---|---|
| C07D 471/04 | (2006.01) |
| C07D 417/14 | (2006.01) |
| C07D 413/14 | (2006.01) |
| C07D 409/14 | (2006.01) |
| C07D 405/14 | (2006.01) |
| C07D 401/14 | (2006.01) |
| C07D 401/04 | (2006.01) |
| C07D 213/71 | (2006.01) |
| C07D 213/68 | (2006.01) |

(52) U.S. Cl.
CPC ............ *C07D 401/04* (2013.01); *C07D 213/68* (2013.01); *C07D 213/71* (2013.01); *C07D 401/14* (2013.01); *C07D 405/14* (2013.01); *C07D 409/14* (2013.01); *C07D 413/14* (2013.01); *C07D 417/14* (2013.01); *C07D 471/04* (2013.01); *C07D 513/04* (2013.01)

(58) Field of Classification Search
CPC .. C07D 213/68; C07D 213/71; C07D 401/04; C07D 401/14; C07D 405/14; C07D 409/14; C07D 413/14; C07D 417/14; C07D 471/04; C07D 513/04
See application file for complete search history.

(56) References Cited

U.S. PATENT DOCUMENTS

| 2009/0088459 A1 | 4/2009 | Dehmlow et al. |
| 2009/0111858 A1 | 4/2009 | Starrett, Jr. et al. |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the internet, URL:http://www.cnn/com/2003/HEALTH/conditions/09/24/alzheimers.drug.ap/index.html>.*

* cited by examiner

*Primary Examiner* — Rebecca Anderson
(74) *Attorney, Agent, or Firm* — Hultquist IP; Steven J. Hultquist

(57) ABSTRACT

The present invention relates to novel bipyridine sulfonamide derivatives of formula (I) and their use for the treatment and/or prophylaxis of a neurodegenerative disease or condition, particularly Alzheimers disease (AD), a cardiovascular disease or a pathology involving ischemia. Additionally, processes for preparing such derivatives and pharmaceutical compositions comprising them are provided.

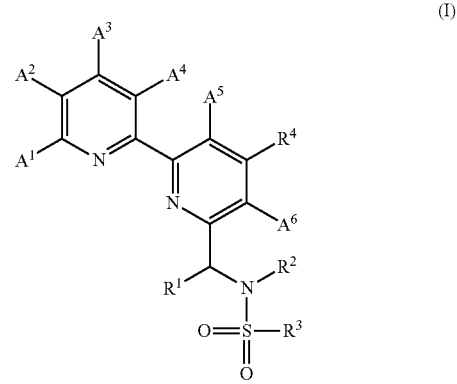

18 Claims, No Drawings

BIPYRIDINE SULFONAMIDE DERIVATIVES FOR THE TREATMENT OF NEURODEGENERATIVE DISEASES OR CONDITIONS

CROSS-REFERENCE TO RELATED APPLICATIONS

This application is a U.S. national phase under the provisions of 35 U.S.C. §371 of International Patent Application No. PCT/EP11/70593 filed Nov. 21, 2011, the disclosure of which is hereby incorporated herein by reference, for all purposes, which in turn claims priority of European Patent Application No. 10382303.4 filed Nov. 22, 2010.

FIELD OF THE INVENTION

The present invention relates to novel bipyridine sulfonamide derivatives and their use for the treatment and/or prophylaxis of a neurodegenerative disease or condition, particularly Alzheimer's disease (AD), a cardiovascular disease or a pathology involving ischemia. Additionally, processes for preparing such derivatives and pharmaceutical compositions comprising them are provided.

BACKGROUND OF THE INVENTION

Oxidative Stress

Oxidative stress is known to be involved in many diseases, including atherosclerosis and other cardiovascular diseases, pathologies involving ischemia, and neurodegenerative diseases or conditions, such as Parkinson's disease (PD) and Alzheimer's disease (AD), and may also be important in ageing.

Reactive oxygen species (ROS), such as oxygen radical superoxide ($O^{2-}$) or hydrogen peroxide ($H_2O_2$), are produced during normal metabolic processes and perform several useful functions [Halliwell B., *J. Neurochem.;* 1992, 59 859: 1609-1623]. Cells are provided with several mechanisms to control levels of these oxidative agents, for instance, superoxide dismutase (SOD), glutathione or vitamin E. In normal physiological conditions, a balance between ROS and these anti-oxidative mechanisms exists. An excessive production of ROS and a loss of efficiency of the anti-oxidative defenses can lead to cellular oxidative stress and thus to pathological conditions in cells and provoke tissue damage. Oxidative stress leads to the destruction of multiple cell types through apoptotic pathways; it can lead to apoptosis in neurons, endothelial cells (ECs), cardiomyocytes, and smooth muscle cells that involve separate as well as overlapping pathways. Oxidative stress in conjunction with processes of mitochondrial dysfunction can contribute to a variety of disease states such as ischemia, cognitive loss, Alzheimer's disease, pain sensation, trauma [for a review. see Maiese K. et al. *Exp Gerontol.* 2010; 45(3): 217-234] and diabetes and diabetic complications, including microvascular and macrovascular changes leading to retinopathy, nephropathy, neuropathy and damage to critical blood vessels, such as the coronary arteries, and the peripheral arterial disease [for a review, see Yang H. et al. *Clin Chem Lab Med* 2011; 49(11):1773-1782].

Neurons are particularly vulnerable to oxidative stress, because of their high rate of metabolic activity, and thus seems to be related to a series of degenerative processes, diseases and syndromes, for example AD, PD, amyotrophic lateral sclerosis (ALS) and schizophrenia [Schulz et al., *Eur. J. Biochem.;* 2000, 267, 4904-4911], Huntington's Disease [Segovia J. and Pérez-Severiano F, *Methods Mol. Biol.;* 2004; 207: 321-334], brain injuries, such as stroke and ischemia [El Kossi et al., Stroke; 2000; 31: 1889-1892; Allen & Bayraktutan, *Int J Stroke,* 2009, 4(6):461-70], vascular cognitive impairment and cerebrovascular dysfunction [Iadecola C. Acta *Neuropathol.* 2010; 120(3): 287-296], multiple sclerosis [Gilgun-Sherki Y. et al., *J. Neurol.;* 2004; 251 (3): 261-8], epilepsy [Costello D. J. and Delanty N., *Expert. Rev. Neurother.;* 2004; 4(3):541-553], and Friedreich's Ataxia [Calabrese et al., *J. Neurol. Sci.;* 2005]. Treatments that lead to an enhancement of the anti-oxidative mechanisms may slow down the progression of some of the mentioned diseases.

In addition to its direct damaging effect on macromolecules, ROS can act as biochemical messengers that regulate various intracellular signaling pathways. ROS have been implicated in regulation of calcium ($Ca^{2+}$) induced signaling in the vasculature which in turn can activate calcium dependent protein kinases and phosphatases activity such as PKC and calcineurin. Intracellular ROS also affect the activity of protein kinase pathways by influencing the redox state of the cell. Gene expression pattern is also regulated by ROS via modulation of transcription factor activity particularly nuclear factor kappaB (NFκB), AP-1 and the peroxisome proliferators activated receptor (PPAR) family of transcriptional activators. There is recent evidence that shows that cardiovascular disease mechanisms are strongly linked to the production of reactive oxidant species and the dysregulation of oxidant-antioxidants pathways in different pathologies such as hypertension, atherosclerosis, heart failure, angina and myocardial infarction [for a review, see Elahi M. M. et al. *Oxidative Medicine and Cellular Longevity,* 2009, 2:5, 259-269].

Another type of cellular stress is the endoplasmic reticulum (ER) stress. The ER is an intracellular organelle represented by an extensive network formed by cisternae and microtubules and which extends from the nuclear envelope to the cell surface in all eukaryotic cells. ER plays several vital functions: the rough ER is the place for protein synthesis and postranslational changes for the correct folding of proteins, ER is the common transport route to deliver proteins to their proper destination within the cell and it is also a $Ca^{2+}$ reservoir. Disturbances in the function of ER lead to accumulation of unfolded proteins within the ER, including oxidative stress, ischemia/hypoxia, disturbance of calcium homeostasis, and overexpression of normal and/or incorrectly folded proteins, inducing a condition generally referred to as ER stress. The resulting ER stress triggers the unfolded protein response (UPR) that induces signal transduction events to reduce the accumulation of unfolded proteins by increasing ER resident chaperones, inhibiting protein translation, and accelerating the degradation of unfolded proteins. However, if stress is severe and/or prolonged, the ER also initiates apoptotic signaling which leads to cell death via mitochondria-dependent and -independent apoptotic pathways. Recent animal and human studies have revealed that the UPR and ER-initiated apoptosis are implicated in the pathophysiology of various cardiovascular diseases, including heart failure, ischemic heart disease, the development of atherosclerosis, and plaque rupture [Minamino T. & Kitakaze M. *J Mol Cell Cardiol.* 2010; 48(6): 1105-10]. Some studies [Chen et al., *FASEB J.* 2004; 18(10):1162-4] demonstrate that ER stress activates the enzyme glycogen synthase kinase 3β, an enzyme involved in the neurodegenerative process occurred in patients with AD and in other pathological pathways.

A further common sign of neurodegenerative diseases is the accumulation and deposits of misfolded proteins which affect several signalling pathways which finally lead to neuronal death. Some authors [Lindholm et al., *Cell Death and Differentiation;* 2006; 13: 385-392] consider that ER stress is related to several neurodegenerative diseases, such as PD, AD, ALS, and transmissible spongiform encephalopaties (TSEs).

Additionally, oxidative stress plays a relevant role in other pathologies or conditions such as hepatic ischemia/reperfusion (I/R) injury [Klune J. R. & Tsung A. *Surg Clin North Am.* 2010 August; 90(4):665-77], renovascular disease and ischemic nephropathy [Textor & Lerman. *Am J. Hypertens.* 2010; 23(11): 1159-1169], organ transplantation [Czubkowski et al. *Ann Transplant.* 2011; 16(1):99-108] and inflammation [Gill et al. *Free Radic Biol Med.* 2010 May 1; 48(9):1121-32]. Furthermore, ischemia is one of the key factors determining the pathophysiology of many retinal diseases, such as diabetic retinopathy, glaucoma, anterior ischemic optic neuropathy, age-related macular degeneration, retinopathy of prematurity [Neroev V. V. et al. *Vestn Oftalmol.* 2010 May-June; 126(3):59-64]

In view of the above, an interesting approach for developing new pharmaceutical compounds for treating neurodegenerative diseases, cardiovascular diseases, pathologies involving ischemia and other diseases mentioned above, is the design of compounds which inhibit cellular oxidative stress.

Beta Amyloid

β-Amyloid peptides (Aβ) are generated in neuronal secretory vesicles by proteolytic cleavage of the type I transmembrane amyloid precursor protein (APP) by aspartyl-proteases, called β-secretase and γ-secretase, that cleave at the N terminus and variant C-termini of Aβ within APP, respectively, resulting in Aβ of 40 or 42 amino acids (Aβ40 and Aβ42, respectively) [Hook V. et al. (2008). *Biological Chemistry* 389 (8): 993-1006]. As an example of their effects, both peptides have been believed to initiate aggregation and later deposition in the neuritic plaques characteristic for AD [Findeis et al. (2007). *Alzheimer's disease Pharmacol. Therapeut* 116: 266-286].

The literature on Aβ biology is replete with a variety of different mechanisms of action, some of which may relate to varying structural states of the peptide. In primary neuronal cultures, Aβ oligomers and Aβ-derived diffusible ligands (ADDLs) can bind avidly to neuronal membranes and induce rapid cell death through the mitochondrial apoptotic pathway. In contrast, Aβ fibrils appear to induce a more chronic form of neuritic dystrophy and neuronal cell death. Rapid toxic effects of Aβ have been associated with a pro-oxidant effect of the peptide and may be mediated in part through RAGE (Receptor for Advanced Glycation End products). Aβ can also induce apoptosis through activation of caspases and calpain. Another mechanism of toxicity may involve aberrant activation of cell cycle reentry in neurons, which has been observed in Aβ-treated neuronal cultures and in AD. Little is known about the factors that regulate the generation of toxic Aβ aggregates in the aging brain, although recent studies suggest potential roles for insulin/insulin-like growth factor-1 signalling and calcium homeostasis. Another class of signalling pathways activated by Aβ is involved in the microglial inflammatory response. Amyloid deposits are closely associated with activation of microglia in AD and in APP transgenic mice [for a review: Yankner B. A. and Lu T. (2009). *Journal of Biological Chemistry* 284 (8): 4755-4759].

Moreover, it has been recently established that oxidative stress and hypoxia significantly increase beta-site APP cleaving enzyme (BACE1) gene transcription through the overexpression of hypoxia inducible factor 1alpha, resulting in increased BACE1 secretase activity and amyloid-beta production [Guglielmotto M. et al. (2009). *J. Neurochem.* 108 (4): 1045-56].

The presence of Aβ deposits in the brain has been related to numerous diseases, such as Alzheimer's disease [Iversen et al. (1995). *Biochem J* 311(Pt 1):1-16; Sisodia S. S. (1999). *J Clin Invest* 104:1169-1170; Selkoe D. J., (2001). *Physiol Rev* 81:741-766; Gandy et al. (2003). *Alzheimer Dis Assoc Disord* 17:259-266], memory loss, attention deficit symptoms associated with Alzheimer's disease, diffuse Lewy body type Alzheimer's disease [Gomperts S. N. et al. (2008). *Neurology,* 16; 71(12): 903-10], mild cognitive impairment [Frankfort S. V. et al. (2008). *Curr Clin Pharmacol.* 3(2): 123-31], Hereditary Cerebral Haemorrhage with Amyloidosis of the Dutch-Type [Maat-Schieman M. et al. (2005). *Neuropathology,* 25(4): 288-97], β-amyloid angiopathy and cerebral bleeding such as cerebral bleeding due to solitary cerebral amyloid angiopathy [Pezzini A. and Padovani A. (2008). *Neurol Sci.* 29 Suppl 2: S260-3], prion infections [Lupi O. and Peryassu M. A. (2007). *Prion* 1(4):223-7], type II diabetes [Götz J., Ittner L. M. and Lim Y. A. (2009). *Cell Mol Life Sci.* 66(8):1321-5], degenerative dementias, including dementias of mixed vascular and degenerative origin [Eikelenboom P. et al. (2008). *Neurodegener Dis.* 5(3-4):190-3], frontotemporal dementia [Rosso S. M. and van Swieten J. C. (2002). *Curr Opin Neurol.* 15(4): 423-8], pre-senile dementia, senile dementia [Tian J. et al. (2004). *Panminerva Med.* 46(4): 253-64], AIDS associated dementia [Everall I. P. et al (2005). *Neurotox Res.* 8(1-2): 51-61], parkinsonian disorders such as Parkinson's disease (PD), subacute sclerosing panencephalitis, postencephalitic parkinsonism, dementia pugilistica, guam parkinsonism-dementia complex, Pick's disease, multiple system atrophy (MSA), progressive supranuclear palsy (PSP), and corticobasal degeneration (CBD) [Constantinescu R. et al. (2008). *Parkinsonism Relat Disord.* 15(3): 205-12], Down syndrome [Lott I. T. et al. (2006). *Curr Alzheimer Res.* 3(5): 521-8], Lewy body disease [Hanson J. C. and Lippa C. F. (2009). *Int. Rev. Neurobiol.* 84:215-28], Huntington's Disease [Mena M. A. et al. (2009). *Prion.* 3(1): 5-11], amyotrophic lateral sclerosis [Harrison R. S. et al. (2007). *Rev Physiol Biochem Pharmacol.* 159: 1-77], multiple sclerosis [Mattsson N. et al. (2009). *Mult Scler.* 15(4): 448-54] and neurotraumatic diseases and acute stroke [Smith E. E. and Greenberg S. M. (2009). *Stroke.* 40(7): 2601-6], epilepsy [Palop J. J. and Mucke L. (2009). *Arch Neurol.* 66(4): 435-40], mood disorders such as depression, schizophrenia and bipolar disorders [Lavretsky H. et al. (2009). *Am. J. Geriatr. Psychiatry.* 17(6): 493-502], promotion of functional recovery post stroke, ischemia [Guglielmotto M. et al. (2009). *J. Neurochem.* 108(4): 1045-56], brain injury, especially traumatic brain injury [Chen X. H. et al. (2004). *Am. J. Pathol.* 165(2):357-71], inflammation and chronic inflammatory diseases [Salminen A. et al. (2009). *Prog Neurobiol.* 87(3):181-94].

The importance of this therapeutic potential of inhibiting the deposition of β-amyloid peptides has motivated many researchers to isolate and characterize secretase enzymes and try to identify potential inhibitors thereof (see, e.g., WO01/23533 A2, EP0855444, WO00/17369, WO00/58479, WO00/47618, WO00/77030, WO01/00665, WO01/00663, WO01/29563, WO02/25276, U.S. Pat. No. 5,942,400, U.S. Pat. No. 6,245,884, U.S. Pat. No. 6,221,667, U.S. Pat. No. 6,211,235, WO02/02505, WO02/02506, WO02/02512, WO02/02518, WO02/02520, WO02/14264, WO05/058311, WO05/097767, WO06/041404, WO06/041405, WO06/0065204, WO06/0065277, US2006287294, WO06/138265, US20050282826, US20050282825, WO06/138217, WO06/

138230, WO06/138264, WO06/138265, WO06/138266, WO06/099379, WO06/076284, US20070004786, US20070004730, WO07/011,833, WO07/011,810, US20070099875, US20070099898, WO07/049,532, WO07/149,033). These documents describe the development of drugs as a treatment and/or prophylaxis of Aβ-related pathologies such as Down syndrome and β-amyloid angiopathy, such as but not limited to cerebral amyloid angiopathy, hereditary cerebral hemorrhage, disorders associated with cognitive impairment, such as, but not limited to, MCI ("mild cognitive impairment"), Alzheimer's disease, memory loss, attention deficit symptoms associated with Alzheimer's disease, neurodegeneration associated with diseases such as Alzheimer's disease or dementia including dementia of mixed vascular and degenerative origin, pre-senile dementia, senile dementia and dementia associated with Parkinson's disease, progressive supranuclear palsy or cortical basal degeneration.

Therefore, due to the involvement of β-amyloid in these diseases, there is a need to develop therapeutic agents that effectively reduce β-amyloid deposition.

Particularly, Alzheimer's disease (AD) is a neurodegenerative disorder characterized by the presence of β-amyloid protein (Aβ) deposits in the core of neuritic plaques and neurofibrillary tangles (NFTs) in the brain of AD patients. Abnormal accumulation of neurotoxic Aβ peptides is a significant factor in the development of AD, and thought to be the likely cause of memory and cognitive loss in this disease condition [Iversen et al. (1995). *Biochem J* 311(Pt 1):1-16; Sisodia S. S. (1999). *J Clin Invest* 104:1169-1170; Selkoe D. J., (2001). *Physiol Rev* 81:741-766; Gandy et al. (2003). *Alzheimer Dis Assoc Disord* 17:259-266]. Neuropathological examination of brains from AD patients reveals that the accumulation of secreted Aβ peptides in extracellular amyloid plaques is involved in neuronal loss in brain regions (hippocampus and cortex) responsible for memory and cognitive functions. Clearly, strategies to reduce Aβ production will facilitate development of therapeutic agents for the treatment of AD [Hook V. et al. (2008). *Biological Chemistry* 389 (8): 993-1006].

Alpha Secretase

In spite of the amyloidogenic processing of APP explained above, the vast majority of APP is converted constitutively in the non-amyloidogenic pathway by α-secretase and γ-secretase activities. Proteolysis of APP by α-secretase occurs within the extracellular region of APP between amino acids Lys 16 and Leu 17 of the Aβ sequence, and therefore precludes the formation of Aβ peptides [Haass C. et al. (1992). *Nature* 357(6378): 500-503; Sisodia S. S. (1992). *Proc Natl Acad Sci USA* 89(13): 6075-6079; Anderson J. P. et al. (1991). *Neurosci Lett* 128(1): 126-128; Esch F. S. et al. (1990). *Science* 248(4959): 1122-1124; Sisodia S. S. et al. (1990). *Science* 248(4954): 492-495]. In addition, α-secretase cleavage releases the N-terminal extracellular domain of APP termed sαAPP, which has neurotrophic and neuroprotective properties [Small D. H. et al. (1994). *J Neuroscience* 14(4): 2117-2127; Furukawa K. et al. (1996). *J Neurochem* 67(5): 1882-1896], enhances long-term potentiation and is implicated in modulation of synaptic plasticity [Ishida A. et al. (1997). *Neuro Rep* 8(9-10): 2133-2137]. A decrease in α-secretase activity may contribute to the development of AD, because lower levels of soluble APP (sAPP) were found in the cerebrospinal fluid (CSF) of AD patients [Lannfelt L. et al. (1995). *Nat Med* 1(8): 829-832; Sennvik K. et al. (2000). *Neurosci Lett* 278(3): 169-172; Palmed M. R. et al. (1990). *Neurology* 40(7): 1028-1034].

A number of studies performed with cultures cells showed that sAPP enhances synaptogenesis, neurite outgrowth, cell survival and cell adhesion [Mattson M. P. (1997). *Physiol Rev* 77(4): 1081-1132)]. Several investigations performed with mice have shown the neuroprotective function of sAPP in vivo. Ring et al. demonstrated that in APP knock-in lines the expression of APP N-terminal domains either grossly attenuated or completely rescued the prominent deficits of APP knock-out mice, such as reductions in brain and body weight, grip strength deficits, alterations in circadian locomotor activity, exploratory activity, and the impairment in spatial learning and long-term potentiation [Ring S. et al. (2007). *The Journal of Neuroscience* 27(29):7817-7826]. Furthermore, Bell et al. confirmed the neurotrophic influence of sαAPP on cortical synaptogenesis since they demonstrated that exogenous infusion of sαAPP led to significant elevations in the cholinergic, glutamatergic and GABAergic cortical presynaptic boutons [Bell K. F. et al. (2008). *Neurobiol Aging* 29(4): 554-65]. Moreover, Caillé et al. demonstrated that infusion of a recombinant sAPP-Fc protein into the lateral ventricle of adult mice (that is the largest neurogenic area of the adult brain) increased the number of EGF-responsive progenitor cells by their increased proliferation confirming the role for sAPP in adult neurogenesis [Caillé I. et al. (2004). *Development and disease* 131(9): 2173-2181]. Finally, Meziane et al. (1998) shown that secreted forms of the β-amyloid precursor protein (APPs 751 and APPs 695), mainly produced by α-secretase cleavage, have potent memory-enhancing effects and block learning deficits induced by scopolamine when administered intracerebroventricularly to mice [Meziane H. et al. (1998). *Proc. Natl. Acad. Sci. USA* 95: 12683-12688].

Activation of several G protein-coupled receptors (GPCRs) has been reported to increase the non-amyloidogenic processing of APP. For example, cellular APP processing can be modulated by muscarinic acetylcholine receptors (mAChR) [Nitsch R. M. et al. (1992). *Science* 258 (5080): 304-307; Hung et al. (1993). *J Biol Chem* 268(31): 22959-22962]. Stimulation of other PLC-coupled GPCRs, such as the metabotropic glutamate receptor 1α (mGluR1α) or serotonin 5-HT2a and 5-HT2c receptors, also results in enhanced amounts of secreted APP [Nitsch R. M. et al. (1996). *J Biol Chem* 271(8): 4188-4194]. Other cellular signalling pathways linked to increased α-secretase processing of APP include mitogen-activated protein kinases (MAP kinases) [Mills J. et al. (1997). *J Neurosci* 17(24): 9415-9422; Kojro et al. (2006). *FASEB J*] and phosphatidylinositol 3-kinase (PI3-kinase) [Solano D. C. et al. (2000). *FASEB J* 14(7): 1015-1022; Kojro et al. (2006). *FASEB J Published online]*.

Increasing the α-secretase cleavage of APP represents an alternative strategy to decrease the concentration of Aβ peptides. Most important, this strategy has an additional beneficial impact compared to β/γ-secretase inhibition since it enhances the amount of neuroprotective sαAPP [Postina R. (2008). *Current Alzheimer Research* 5: 179-186].

Therefore, α-secretase activators are expected to have a therapeutic application for numerous diseases related to the presence of Aβ deposits in the brain, such as Alzheimer's disease, memory loss, attention deficit symptoms associated with Alzheimer's disease, diffuse Lewy body type Alzheimer's disease, mild cognitive impairment, Hereditary Cerebral Haemorrhage with Amyloidosis of the Dutch-Type, β-amyloid angiopathy and cerebral bleeding such as cerebral bleeding due to solitary cerebral amyloid angiopathy, prion infections, type II diabetes, degenerative dementias, including dementias of mixed vascular and degenerative origin, frontotemporal dementia, pre-senile dementia, senile dementia, AIDS associated dementia, parkinsonian disorders such as Parkinson's disease (PD), subacute sclerosing panencephalitis, postencephalitic parkinsonism, dementia pugilistica, guam parkinsonism-dementia complex, Pick's disease, multiple system atrophy (MSA), progressive supranuclear palsy (PSP), and corticobasal degeneration (CBD), Down syndrome, Lewy body disease, Huntington's Disease, amyotrophic lateral sclerosis, multiple sclerosis, neurotraumatic diseases, acute stroke, epilepsy, mood disorders such as depression, schizophrenia and bipolar disorders, promotion of functional recovery post stroke, ischaemia, brain injury, especially traumatic brain injury, inflammation and chronic inflammatory diseases.

Thus there is an existing need to provide alternative compounds for the treatment and/or prophylaxis of cognitive, neurodegenerative or neuronal diseases or disorders. Said compounds should preferably improve existing treatments, for example in terms of improved activity, efficacy bioavailability or reduced toxicity.

Bipyridine Sulfonamide Derivatives

A few bipyridine sulfonamide derivatives, wherein an optionally substituted sulfonamidemethyl group is directly linked to the bipyridine moiety, have been described so far.

Regarding substitution at position 2 of the pyridine (those most similar to the compounds according to the present invention), only for two compounds a biological activity has been described, namely their ability to catalyze the dephosphorylation of ATP [Qian, Ligang et al.; *Journal of Coordination Chemistry* (1991), 23(1-4), 155-72].

Regarding substitution at other positions of the pyridine, one further biological activity has been described for compounds substituted at position 3 of the pyridine, namely promoting of LDL receptor gene transcription, disclosed in Patent Application WO2002055484.

BRIEF DESCRIPTION OF THE INVENTION

A novel family of compounds has been developed, namely bipyridine sulfonamide derivatives, defined by Formula (I) as detailed below, which show the property of protecting cells from oxidative stress, particularly from hydrogen peroxide induced cell death.

Further, some of the developed bipyridine sulfonamide derivatives have been tested for determining their potential of inhibiting Aβ secretion and activating stimulation of sAPPα secretion; they have displayed such activities, as shown herein.

Bipyridine sulfonamide derivatives of Formula (I) according to the present invention are thus expected to be useful for the treatment or prophylaxis of neurodegenerative diseases or conditions, cardiovascular diseases or pathologies involving ischemia.

Therefore, according to a first aspect, the present invention is directed to a compound of Formula (I):

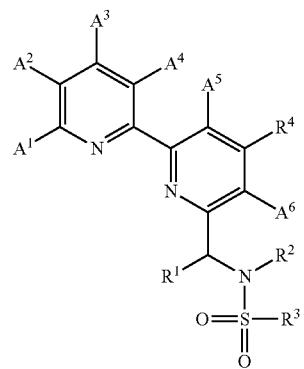

wherein
$R^1$ is selected from hydrogen, optionally substituted $C_1$-$C_6$ alkyl, halogen, nitro and amino;
$R^2$ is selected from hydrogen, optionally substituted heterocycloalkylalkyl, optionally substituted heteroarylalkyl, optionally substituted —($SO_2$)-thiophene and optionally substituted $C_1$-$C_6$ alkyl.
$R^3$ is selected from optionally substituted aryl, optionally substituted arylalkyl, optionally substituted heteroaryl, optionally substituted heterocycloalkyl, optionally substituted $C_1$-$C_6$ alkyl, optionally substituted cycloalkyl, optionally substituted heterocycloalkylalkyl, optionally substituted heteroarylalkyl, cyano, ethenyl and —$N(R^7)(R^8)$, wherein $R^7$ and $R^8$ are independently selected from hydrogen or substituted or unsubstituted alkyl, and when $R^7$ and $R^8$ are substituted or unsubstituted alkyl, they may together form a heterocycloalkyl, containing five to seven members with the nitrogen atom and may intracyclically contain one or more further heteroatoms selected from nitrogen, oxygen and sulphur;
$R^4$ is selected from —O—$R^5$, wherein $R^5$ is optionally substituted $C_1$-$C_6$ alkyl, or —$SO_2$—$R^6$, wherein $R^6$ is $C_1$-$C_6$ alkyl;
$A^1$, $A^2$, $A^3$, $A^4$, $A^5$, $A^6$ are independently selected from hydrogen and $C_1$-$C_6$ alkyl;
or a tautomer, salt, solvate or prodrug thereof.

A further aspect of the present invention is a method for the preparation of a compound of Formula (I) as defined above, or a tautomer, salt, solvate or prodrug thereof, comprising mixing a compound of formula:

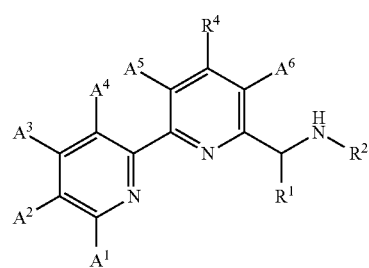

with a sulfonyl chloride of formula $ClSO_2R^3$ in an aprotic or protic solvent,
wherein $R^1$-$R^4$ and $A^1$-$A^6$ are as defined above.

Another aspect of the present invention relates to a pharmaceutical composition comprising at least one of the compounds of Formula (I), or tautomers, salts, solvates or prodrugs thereof, and at least one pharmaceutically acceptable carrier, adjuvant and/or vehicle.

Another aspect of the present invention is a compound of Formula (I), or a tautomer, salt, solvate or prodrug thereof, for use as a medicament.

A further aspect of the present invention refers to a compound of Formula (I), or a tautomer, salt, solvate or prodrug thereof, for use as a medicament for the treatment and/or prophylaxis of a cognitive, neurodegenerative or neuronal disease or disorder, a cardiovascular disease, diabetes or a diabetic complication, a pathology involving ischemia, inflammation or organ transplantation complications due to oxidative stress.

DETAILED DESCRIPTION OF THE INVENTION

In the context of the present invention, the following terms of the compounds of formula (I) have the meaning indicated below:

The term "alkyl" refers to a linear or branched hydrocarbon chain radical consisting of carbon and hydrogen atoms, containing no instauration, having one to twelve, or one to eight, or one to six, or one to three carbon atoms, and which is attached to the rest of the molecule by a single bond. Examples of alkyl groups include, but are not limited to alkyl groups such as methyl, ethyl, n-propyl, isopropyl, isobutyl, 3-methyl-1-pentyl, 4-methyl-1-pentyl, 3,3-dimethyl-1-butyl, t-butyl, pentyl, isopentyl, and hexyl. An alkyl group may be optionally substituted by one or more substituents, the substituents being as defined below.

The term "cycloalkyl" means a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, $C_3$-$C_7$ fully saturated cycloalkyl groups, such as cyclopropyl, cyclobutyl, cyclopentyl, cyclohexyl, and cycloheptyl, and saturated cyclic and bicyclic terpenes and $C_3$-$C_7$ cycloalkenyl groups, such as cyclopropenyl, cyclobutenyl, cyclopentenyl, cyclohexenyl, and cycloheptenyl, and unsaturated cyclic and bicyclic terpenes. A cycloalkyl group can be unsubstituted or substituted by one or two suitable substituents, the substituents being as defined below. Preferably, the cycloalkyl group is a monocyclic ring or bicyclic ring.

The term "heterocycloalkyl" means a non-aromatic monocyclic or polycyclic ring comprising carbon and hydrogen atoms and at least one heteroatom, preferably, 1 to 4 heteroatoms selected from nitrogen, oxygen, and sulfur. A heterocycloalkyl group can have one or more carbon-carbon double bonds or carbon-heteroatoms double bonds in the ring as long as the ring is not rendered aromatic by their presence. Examples of heterocycloalkyl groups include aziridinyl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 2 to 6 carbon atoms and from 1 to 3 heteroatoms, referred to herein as $C_1$-$C_6$ heterocycloalkyl. A heterocycloalkyl group may be optionally substituted by one or more substituents, the substituents being as defined below.

The term "halogen" refers to chloro, bromo, iodo or fluoro.

The term "aryl" refers to an aromatic group having between 6 to 18, or between 6 to 10, or 6, 7 or 8 carbon atoms, comprising 1, 2 or 3 aromatic nuclei, optionally fused, including the following non-limiting examples: phenyl, naphthyl, diphenyl, indehyl, phenantryl. An aryl group may be optionally substituted by one or more substituents, the substituents being as defined below.

"Heteroaryl" refers to a stable 3- to 15-membered aromatic ring radical, which consists of carbon atoms and from one to five heteroatoms selected from the group consisting of nitrogen, oxygen and sulphur. In an embodiment of the invention the heteroaryl group is 3- to 10-, or a 5- or 6-membered aromatic ring radical. For the purposes of this invention, the heteroaryl can be monocyclic, bicyclic or tricyclic ring system, which can include systems of fused rings; and the nitrogen, carbon or sulphur atoms in the heteroaryl radical may be optionally oxidized; or the nitrogen atom may be optionally quaternized. Example of such heteroaryl include, but are not limited to, benzimidazole, benzothiazole, furan, pyrrole, thiophene, pyridine, bipyridine, pyrimidine, isothiazole, isoxazol, imidazole, indole, purine, quinoline, thiadiazole. Preferably, heteroaryl refers to pyridine, bipyridine, pyrimidine or isoxazol. An heteroaryl group may be optionally substituted by one or more substituents, the substituents being as defined below.

The term "heteroarylalkyl" relates to an alkyl group substituted with a heteroaryl group as defined above. Preferably, the term "heteroarylalkyl" refers to a group having between 4 and 16 carbon atoms ("$C_{4-16}$ heteroarylalkyl").

The term "heterocycloalkylalkyl" relates to an alkyl group substituted with a heterocycloalkyl group as defined above.

The term "arylalkyl" relates to an alkyl group substituted with an aryl group as defined above. Preferably, the term "arylalkyl" refers to a group having between 7 and 16 carbon atoms ("$C_{7-16}$ arylalkyl").

The term "alkoxyl" refers to a group —O-alkyl, wherein alkyl is as defined above.

The term "alkylcarbonyl" refers to a group —C(O)-alkyl, wherein alkyl is as defined above.

The term "alkoxycarbonyl" refers to a group —C(O)O-alkyl, wherein alkyl is as defined above.

The term "alkylamide" refers to a group —NH—C(O)-alkyl, wherein alkyl is as defined above.

The term "amine" refers to a group $NK^1K^2$, wherein $K^1$ and $K^2$ are independently hydrogen or an alkyl group as defined above. Examples of such amines include, but are not limited to, dimethylamine and ethanolamine.

According to a first aspect, the present invention is directed to a compound of Formula (I):

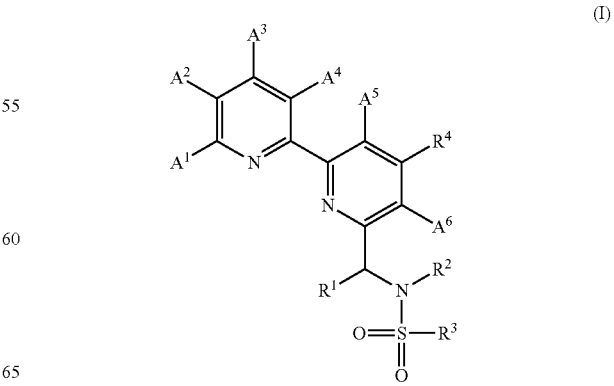

wherein

R¹ is selected from hydrogen, optionally substituted $C_1$-$C_6$ alkyl, halogen, nitro and amino;

R² is selected from hydrogen, optionally substituted heterocycloalkylalkyl, optionally substituted heteroarylalkyl, optionally substituted —($SO_2$)-thiophene and optionally substituted $C_1$-$C_6$ alkyl.

R³ is selected from optionally substituted aryl, optionally substituted arylalkyl, optionally substituted heteroaryl, optionally substituted heterocycloalkyl, optionally substituted $C_1$-$C_6$ alkyl, optionally substituted cycloalkyl, optionally substituted heterocycloalkylalkyl, optionally substituted heteroarylalkyl, cyano, ethenyl and —N(R⁷)(R⁸), wherein R⁷ and R⁸ are independently selected from hydrogen or substituted or unsubstituted alkyl, and when R⁷ and R⁸ are substituted or unsubstituted alkyl, they may together form a heterocycloalkyl, containing five to seven members with the nitrogen atom and may intracyclically contain one or more further heteroatoms selected from nitrogen, oxygen and sulphur;

R⁴ is selected from —O—R⁵, wherein R⁵ is optionally substituted $C_1$-$C_6$ alkyl, or —$SO_2$—R⁶, wherein R⁶ is $C_1$-$C_6$ alkyl;

A¹, A², A³, A⁴, A⁵, A⁶ are independently selected from hydrogen and $C_1$-$C_6$ alkyl;

or a tautomer, salt, solvate or prodrug thereof.

In the above, "optionally substituted" means that the substituents may be further substituted, at any position which may be substituted (including carbon atoms and heteroatoms), with one or more substituents selected from halogen (fluor, chloro, bromo); alkoxyl, preferably methoxyl; alkylcarbonyl, preferably methylcarbonyl; alkoxycarbonyl, preferably methoxycarbonyl and ethoxycarbonyl; hydroxycarbonyl; optionally substituted methyl, e.g. trifluoromethyl; cyano; nitro, methanesulfonyl; isobutyl; tert-butyl; ethanone; acetamide methyl (—$CH_2$—NH—CO—$CH_3$); oxazole or isoxazole optionally substituted by $C_1$-$C_3$ alkyl such as methyl; pyridine; hydroxyl; phenyl; alkylamide, preferably isobutyramide (—NH—CO—CH—($CH_3$)$_2$), O-alkylamino-alkyl, preferably O—($CH_2$)$_2$—N—($CH_2$—$CH_3$)$_2$; N-acetamide; [1,2,3]thiadiazole; dialkylamine, preferably dimethylamine; ethyl; ethyl substituted by an amine such as a dialkylamine or dialkylcarboxyamide, preferably dimethylamine and diethylamine, and preferably wherein the dialkylamine of the dialkylcarboxyamide forms a 4, 5, 6 or 7 membered ring; isopropyl; N-propionamide and ketone.

Preferably, the above substituents are selected from fluor, chloro, bromo, methoxy, methylcarbonyl, methoxycarbonyl, hydroxycarbonyl, ethoxycarbonyl, optionally substituted methyl, e.g. trifluoromethyl, cyano, nitro, methanesulfonyl, pyridine, tertbutyl, acetamide methyl (—$CH_2$—NH—CO—$CH_3$), oxazole or isoxazole optionally substituted by $C_1$-$C_3$ alkyl such as methyl, phenyl, O—($CH_2$)$_2$—N—($CH_2$—$CH_3$)$_2$, N-acetamide, dimethylamine, isopropyl, N-propionamide and ketone.

According to a preferred embodiment, in the compounds of Formula (I):

R¹ is hydrogen;

R² is selected from hydrogen, optionally substituted heteroarylalkyl and optionally substituted —($SO_2$)-thiophene.

R³ is selected from optionally substituted aryl, optionally substituted arylalkyl, optionally substituted heteroaryl, optionally substituted heteroarylalkyl, optionally substituted heterocycloalkyl, optionally substituted heterocycloalkylalkyl, optionally substituted $C_1$-$C_6$ alkyl, optionally substituted cycloalkyl and ethenyl.

In the above, "optionally substituted" means that the substituents may be further substituted, at any position which may be substituted (including carbon atoms and heteroatoms), with one or more substituents, preferably selected from halogen, methoxy, optionally substituted methyl, trifluoromethyl, carboxylic acid methyl ester, cyano, methanesulfonyl, pyridinyl and carboxylic acid.

R² is preferably selected from hydrogen; pyridinemethyl optionally substituted with one or more substituents selected from alkoxyl, pyridine and O-alkylaminoalkyl; and —($SO_2$)-thiophene optionally substituted with halogen.

R³ is preferably selected from optionally substituted phenyl, optionally substituted naphthyl, optionally substituted thiophene, optionally substituted benzothiophene, optionally substituted pyridine, optionally substituted 1,2,4-triazole, optionally substituted thiazole, optionally substituted furane, optionally substituted isoxazole, optionally substituted pyrazole, optionally substituted dihydro-benzo[1,4]dioxine, optionally substituted tetrahydrofurane-methyl, optionally substituted piperidine, optionally substituted pyridine-ethyl, optionally substituted quinoline, optionally substituted benzofurane, optionally substituted imidazole, optionally substituted 2,3-dihydrothiazole, optionally substituted pyrimidine, optionally substituted benzothiazole, optionally substituted cyclohexyl, optionally substituted cyclopropane, optionally substituted methyl, optionally substituted ethyl, optionally substituted propyl, optionally substituted isopropyl, optionally substituted tert-butyl, ethenyl, optionally substituted tetrahydrofurane, and optionally substituted N-morpholine.

More preferably, R² is selected from hydrogen; pyridinemethyl optionally substituted with one or more substituents selected from methoxyl, pyridine, —O—($CH_2$)$_2$—N—($CH_2$—$CH_3$)$_2$; and —($SO_2$)-thiophene optionally substituted with chloro.

More preferably, R³ is preferably selected from phenyl optionally substituted with one or more substituents selected from methoxy, methyl, methylcarbonyl, trifluoromethyl, fluor, chloro, cyano, bromo, methanesulfonyl, nitro, hydroxycarbonyl, tert-butyl and phenyl; naphthyl optionally substituted with dimethylamine; thiophene optionally substituted with one or more substituents selected from chloro, bromo, methyl, methylcarbonyl, oxazole, isoxazole, pyridine, —$CH_2$—NH—CO—$CH_3$, hydroxycarbonyl; benzothiophene optionally substituted with one or more substituents selected from methyl, fluor, chloro; pyridine; 1,2,4-triazole; thiazole optionally substituted with one or more substituents selected from methyl, chloro, N-acetamide; furane optionally substituted with one or more substituents selected from methoxycarbonyl, isoxazole, methyl, methylisoxazole; isoxazole optionally substituted with one or more methyl; pyrazole optionally substituted with one or more substituents selected from methyl, tert-butyl; dihydro-benzo[1,4]dioxine; tetrahydrofurane-methyl; piperidine optionally substituted with ethoxycarbonyl; pyridine-ethyl; quinoline; benzofurane; imidazole optionally substituted with one or more substituents selected from chloro, methyl; 2,3-dihydrothiazole optionally substituted with one or more substituents selected from methyl, ketone; pyrimidine optionally substituted with chloro; benzothiazole; cyclohexyl; cyclopropane; methyl optionally substituted with one or more substituents selected from cyano and fluor; propyl optionally substituted with one or more substituents selected from fluor, chloro; isopropyl; tert-butyl; ethyl optionally substituted with one or more fluor atoms; ethenyl; tetrahydrofurane; and N-morpholine.

According to a further preferred embodiment, in the compounds of Formula (I):

$R^1$ is selected from hydrogen, optionally substituted $C_1$-$C_6$ alkyl, halogen, nitro and amino;

$R^2$ is selected from hydrogen, optionally substituted heterocycloalkylalkyl, optionally substituted heteroarylalkyl, optionally substituted —$SO_2$-thiophene and optionally substituted $C_1$-$C_6$ alkyl;

$R^3$ is selected from optionally substituted aryl, optionally substituted heteroaryl, optionally substituted heterocycloalkyl, optionally substituted $C_1$-$C_6$ alkyl, optionally substituted heterocycloalkylalkyl, optionally substituted heteroarylalkyl and cyano.

In the above, "optionally substituted" means that the substituents may be further substituted, at any position which may be substituted (including carbon atoms and heteroatoms), with one or more substituents, preferably selected halogen, carboxylic acid, carboxylic acid ethyl ester, isobutyl, ethanone, acetamide methyl (—$CH_2$—NH—CO—$CH_3$), isoxazole, pyridine, hydroxy, phenyl, isobutyramide (—NH—CO—CH—($CH_3$)$_2$), methanesulfonyl, N-acetamide, oxazole, [1,2,3]thiadiazole, ethyl, methyl, tert-butyl cyano, isopropyl, N-propionamide and ketone.

According to a preferred embodiment, $R^3$ is preferably selected from the following:

In all of the above, $R^1$ is preferably selected from hydrogen and methyl.

In all of the above, $R^2$ is preferably selected from hydrogen and optionally substituted —($SO_2$)-thiophene.

$R^4$ is preferably selected from —O—CH$_3$, —O—(CH$_2$)$_2$—N(CH$_2$—CH$_3$)$_2$, or —SO$_2$—CH$_3$.

$A^1$, $A^2$, $A^3$, $A^4$, $A^5$, $A^6$ are preferably independently selected from hydrogen methyl, even more preferably are hydrogen.

According to a preferred embodiment, the compounds of Formula (I) are selected from the following:

| Compound | Structure |
|---|---|
| Compound 1 | 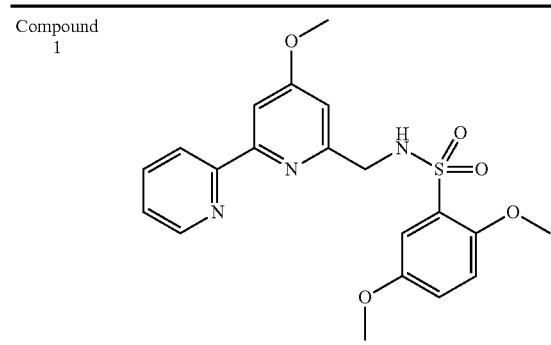 |
| Compound 2 | 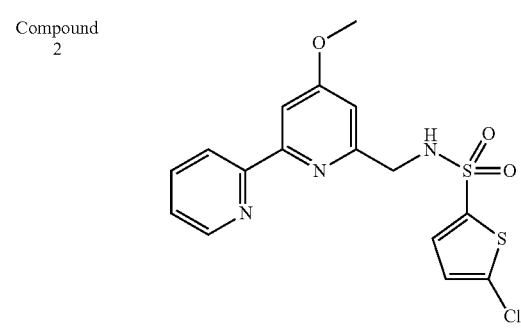 |
| Compound 3 | 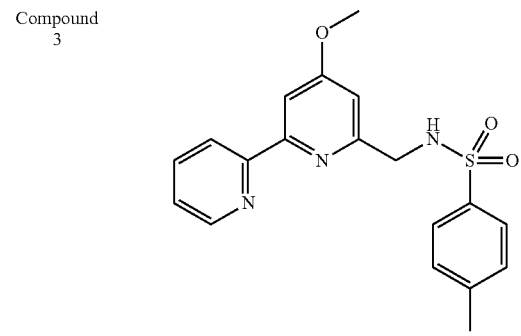 |
| Compound 4 | 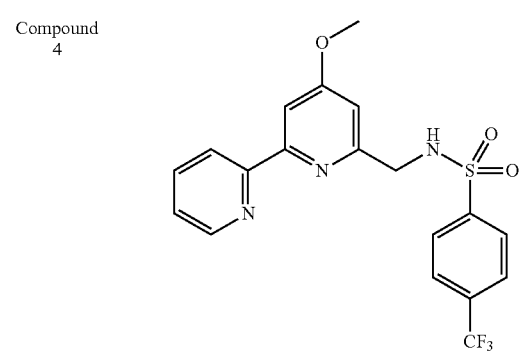 |

-continued

| Compound | Structure |
|---|---|
| Compound 5 | 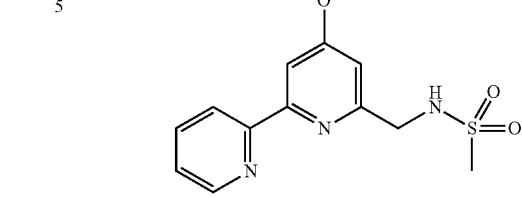 |
| Compound 6 | 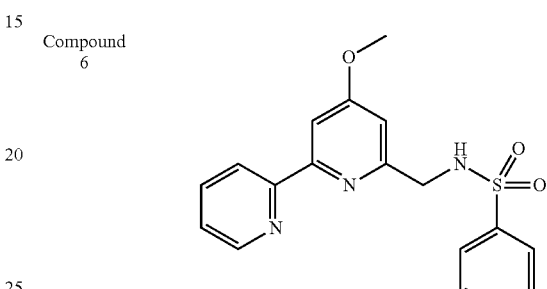 |
| Compound 7 | 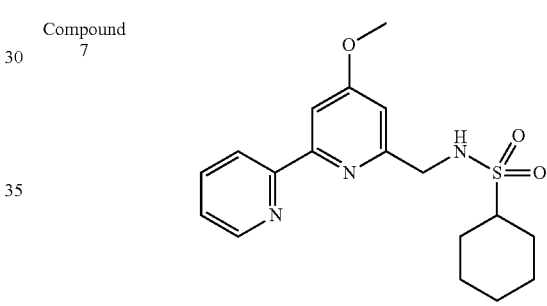 |
| Compound 8 | 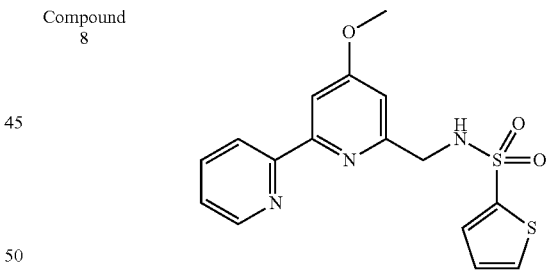 |
| Compound 9 | 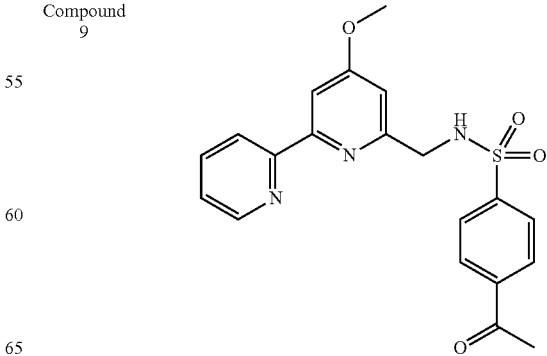 |

-continued

| Compound | Structure |
|---|---|
| Compound 10 | 4-methoxy-6-[(3,5-difluorophenylsulfonamido)methyl]-2,2'-bipyridine |
| Compound 11 | 4-methoxy-6-[(4-fluorophenylsulfonamido)methyl]-2,2'-bipyridine |
| Compound 12 | 4-methoxy-6-[(3-fluorophenylsulfonamido)methyl]-2,2'-bipyridine |
| Compound 13 | 4-methoxy-6-[(4-cyanophenylsulfonamido)methyl]-2,2'-bipyridine |
| Compound 14 | 4-methoxy-6-[(3-cyano-4-fluorophenylsulfonamido)methyl]-2,2'-bipyridine |
| Compound 15 | 4-methoxy-6-[(naphthalene-2-sulfonamido)methyl]-2,2'-bipyridine |
| Compound 16 | 4-methoxy-6-[(4-bromophenylsulfonamido)methyl]-2,2'-bipyridine |
| Compound 17 | 4-methoxy-6-[(trifluoromethylsulfonamido)methyl]-2,2'-bipyridine |
| Compound 18 | 4-methoxy-6-[(5-bromothiophene-2-sulfonamido)methyl]-2,2'-bipyridine |
| Compound 19 | 4-methoxy-6-[(2,5-dichlorothiophene-3-sulfonamido)methyl]-2,2'-bipyridine |

| Compound | Structure |
|---|---|
| Compound 20 | 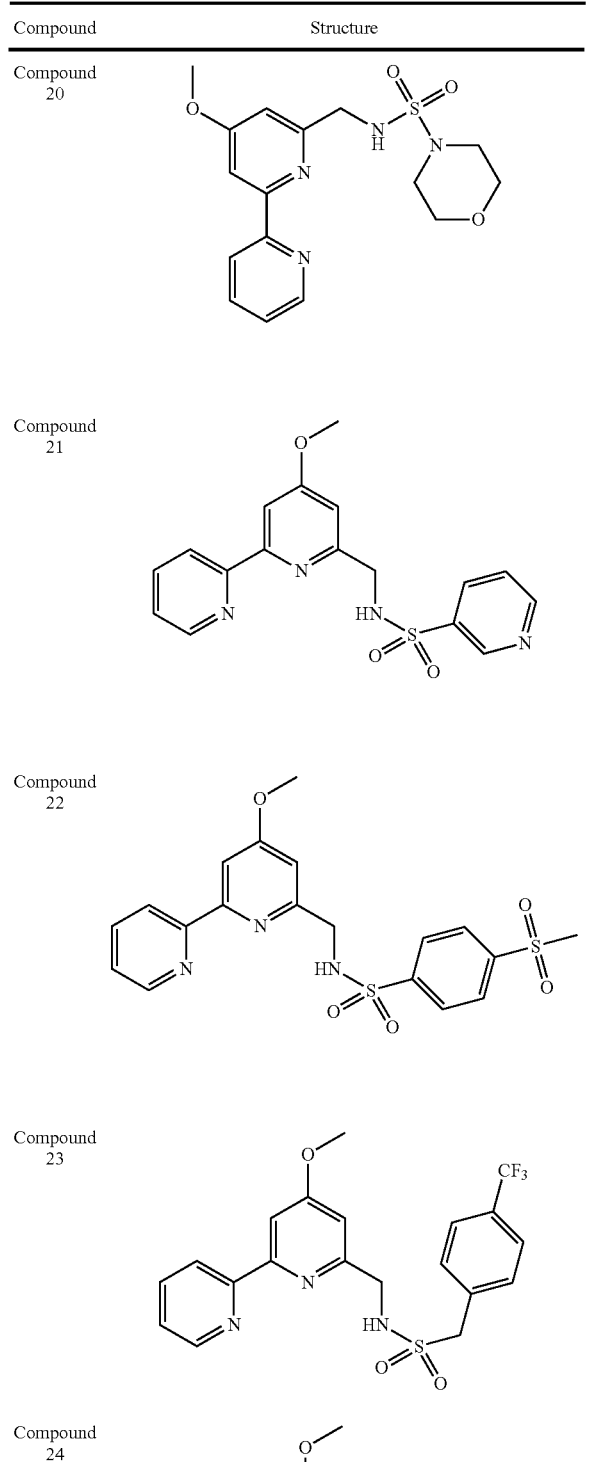 |
| Compound 21 | |
| Compound 22 | |
| Compound 23 | |
| Compound 24 | |
| Compound | Structure |
|---|---|
| Compound 25 | 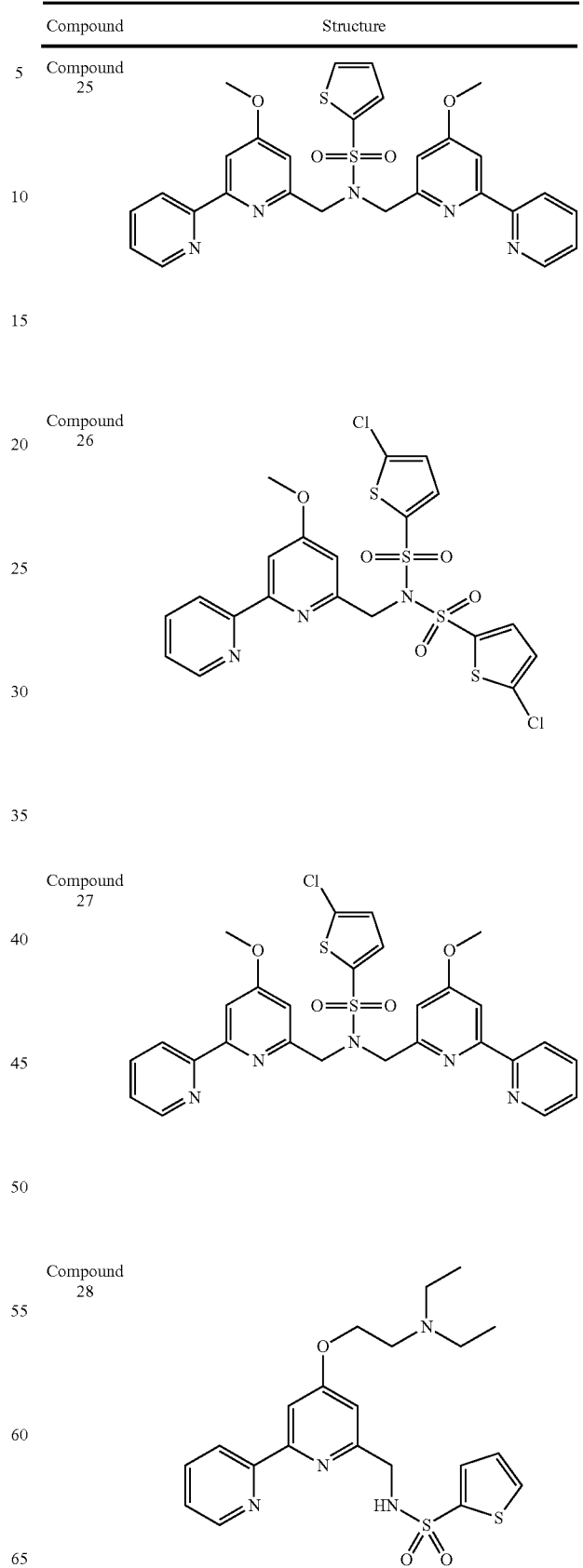 |
| Compound 26 | |
| Compound 27 | |
| Compound 28 | |

| Compound | Structure |
|---|---|
| Compound 29 | 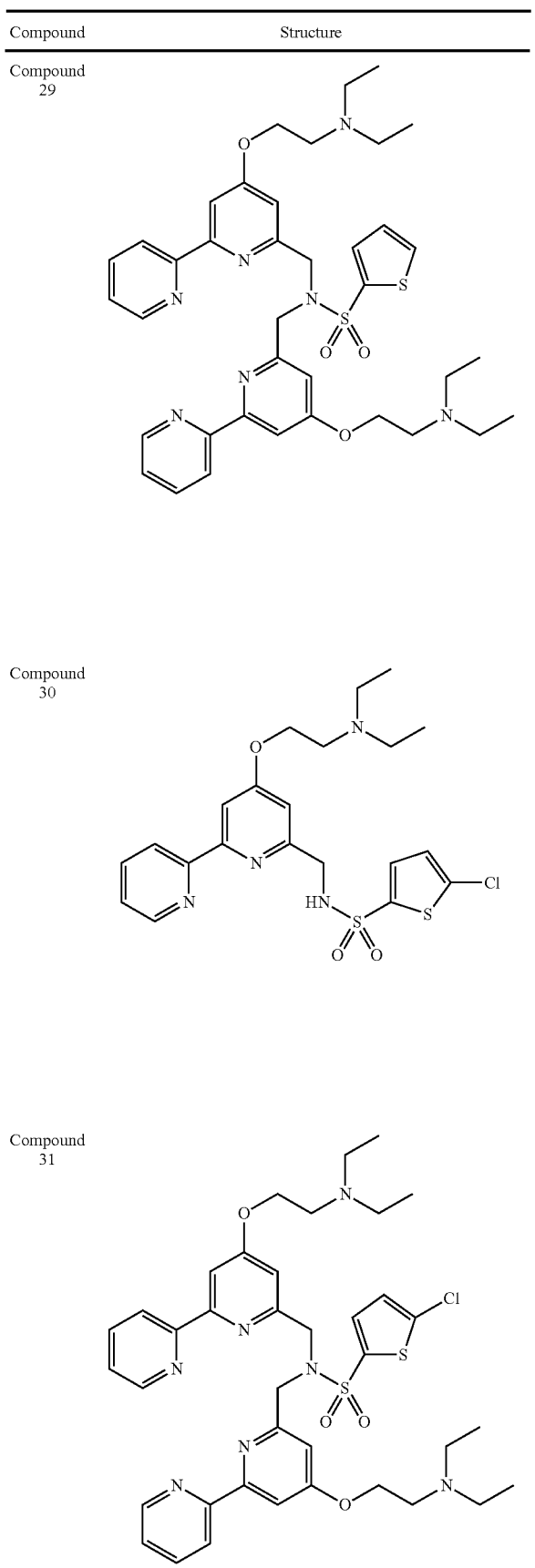 |
| Compound 30 | |
| Compound 31 | |
| Compound | Structure |
|---|---|
| Compound 32 | 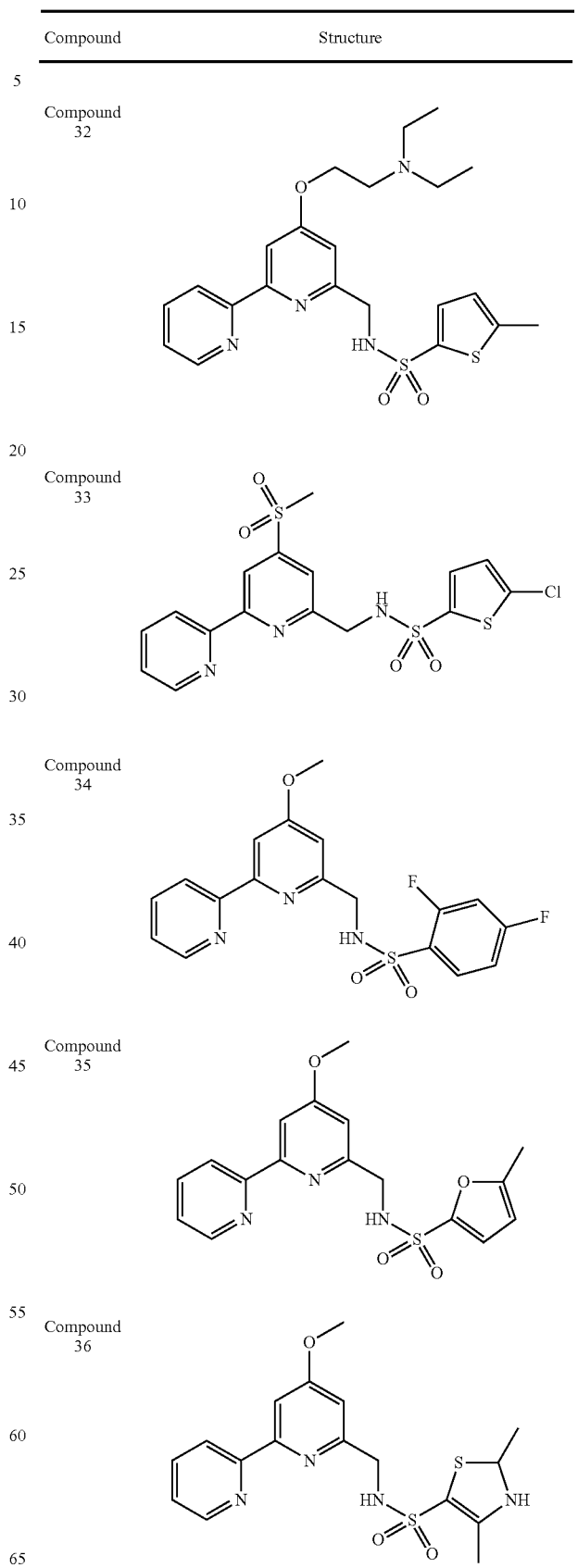 |
| Compound 33 | |
| Compound 34 | |
| Compound 35 | |
| Compound 36 | |

-continued

| Compound | Structure |
|---|---|
| Compound 37 | (4-methoxy-6-(pyridin-2-yl)pyridin-2-yl)methyl isobutylsulfonamide |
| Compound 38 | N-((4-methoxy-6-(pyridin-2-yl)pyridin-2-yl)methyl)-4-methoxybenzenesulfonamide |
| Compound 39 | 3-chloro-N-((4-methoxy-6-(pyridin-2-yl)pyridin-2-yl)methyl)propane-1-sulfonamide |
| Compound 40 | 2-cyano-N-((4-methoxy-6-(pyridin-2-yl)pyridin-2-yl)methyl)benzenesulfonamide |
| Compound 41 | 3-bromo-N-((4-methoxy-6-(pyridin-2-yl)pyridin-2-yl)methyl)benzenesulfonamide |

-continued

| Compound | Structure |
|---|---|
| Compound 42 | N-((4-methoxy-6-(pyridin-2-yl)pyridin-2-yl)methyl)-5-(isoxazol-5-yl)thiophene-2-sulfonamide |
| Compound 43 | 2-bromo-N-((4-methoxy-6-(pyridin-2-yl)pyridin-2-yl)methyl)benzenesulfonamide |
| Compound 44 | 5-chloro-2-fluoro-N-((4-methoxy-6-(pyridin-2-yl)pyridin-2-yl)methyl)benzenesulfonamide |
| Compound 45 | N-((4-methoxy-6-(pyridin-2-yl)pyridin-2-yl)methyl)-1H-1,2,4-triazole-3-sulfonamide |
| Compound 46 | N-((4-methoxy-6-(pyridin-2-yl)pyridin-2-yl)methyl)-5-(pyridin-2-yl)thiophene-2-sulfonamide |

| Compound | Structure |
|---|---|
| Compound 47 | (4-methoxy-6-(pyridin-2-yl)pyridin-2-yl)methyl sulfonamide of 2-chloro-4-methylthiazole-5-sulfonamide |
| Compound 48 | (4-methoxy-6-(pyridin-2-yl)pyridin-2-yl)methylamide of 3-cyanobenzenesulfonamide |
| Compound 49 | (4-methoxy-6-(pyridin-2-yl)pyridin-2-yl)methylamide of 3-chlorobenzenesulfonamide |
| Compound 50 | (4-methoxy-6-(pyridin-2-yl)pyridin-2-yl)methylamide of 2-fluorobenzenesulfonamide |
| Compound 51 | (4-methoxy-6-(pyridin-2-yl)pyridin-2-yl)methylamide of methyl 5-sulfamoylfuran-2-carboxylate |
| Compound 52 | (4-methoxy-6-(pyridin-2-yl)pyridin-2-yl)methylamide of 5-(acetamidomethyl)thiophene-2-sulfonamide |
| Compound 53 | (4-methoxy-6-(pyridin-2-yl)pyridin-2-yl)methylamide of 2-(pyridin-2-yl)ethanesulfonamide |
| Compound 54 | (4-methoxy-6-(pyridin-2-yl)pyridin-2-yl)methylamide of 3,5-dimethylisoxazole-4-sulfonamide |
| Compound 55 | (4-methoxy-6-(pyridin-2-yl)pyridin-2-yl)methylamide of 5-(oxazol-5-yl)thiophene-2-sulfonamide |
| Compound 56 | (4-methoxy-6-(pyridin-2-yl)pyridin-2-yl)methylamide of 3-chloro-2-fluorobenzenesulfonamide |

| Compound | Structure |
|---|---|
| Compound 57 | 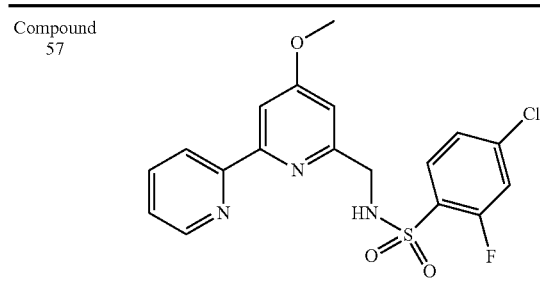 |
| Compound 58 | 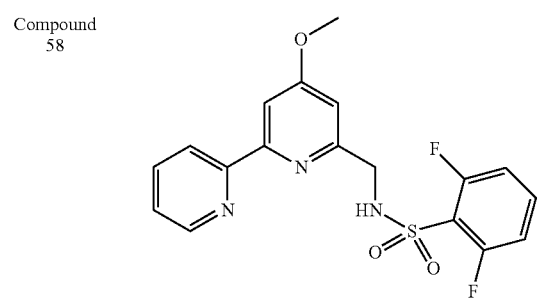 |
| Compound 59 | 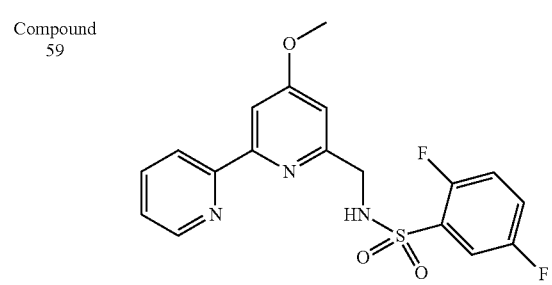 |
| Compound 60 | 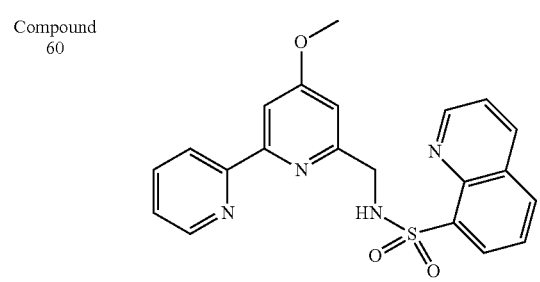 |
| Compound 61 | 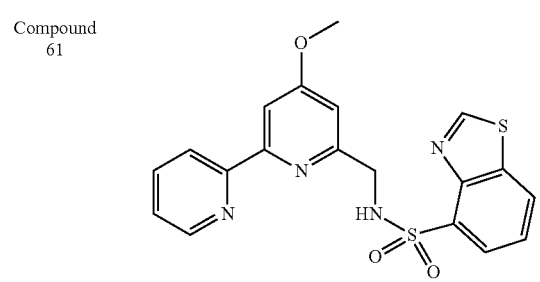 |
| Compound | Structure |
|---|---|
| Compound 62 | 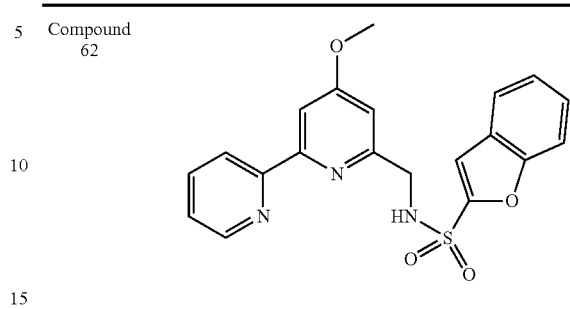 |
| Compound 63 | 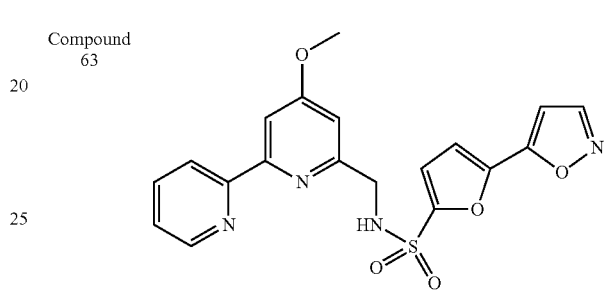 |
| Compound 64 | 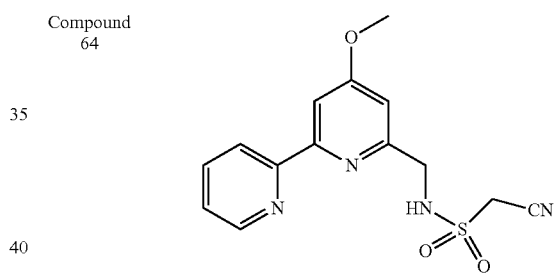 |
| Compound 65 | 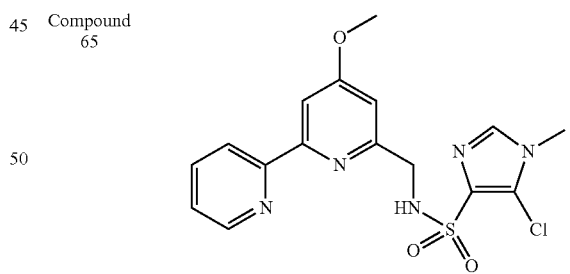 |
| Compound 66 | 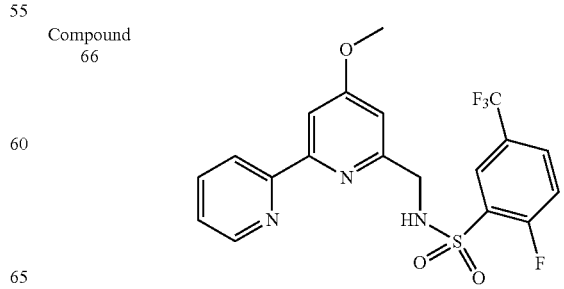 |

| Compound | Structure |
|---|---|
| Compound 67 | 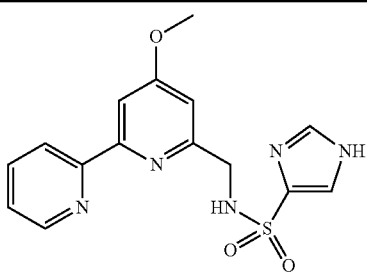 |
| Compound 68 | 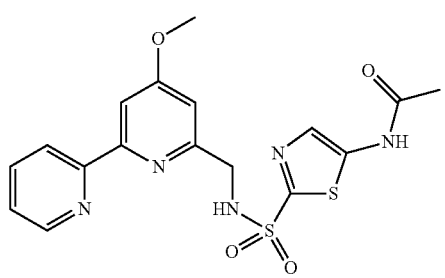 [SMILES: COc1cc(CNS(=O)(=O)c2ncc(NC(C)=O)s2)nc(-c2ccccn2)c1] |
| Compound 69 | 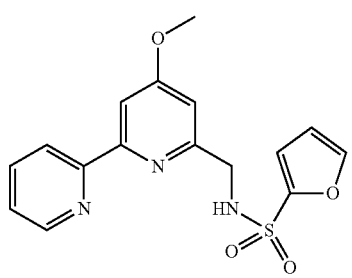 [SMILES: COc1cc(CNS(=O)(=O)c2ccco2)nc(-c2ccccn2)c1] |
| Compound 70 | 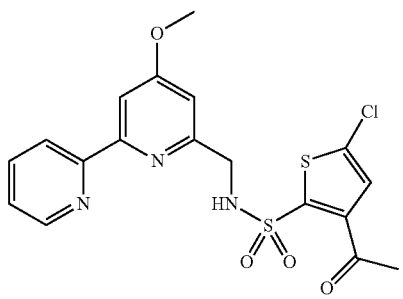 [SMILES: COc1cc(CNS(=O)(=O)c2sc(Cl)cc2C(C)=O)nc(-c2ccccn2)c1] |
| Compound 71 | 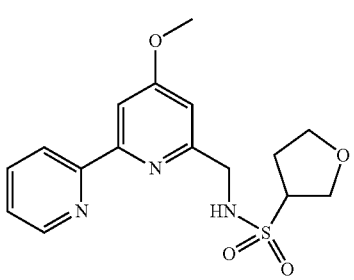 [SMILES: COc1cc(CNS(=O)(=O)C2CCOC2)nc(-c2ccccn2)c1] |
| Compound 72 | 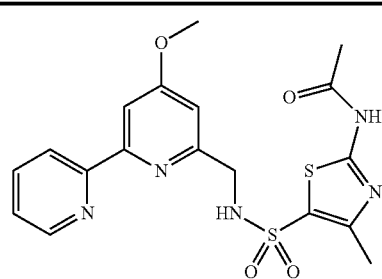 |
| Compound 73 | 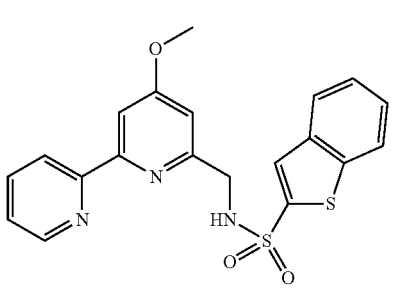 |
| Compound 74 | 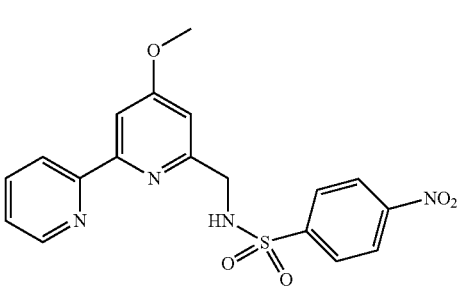 [SMILES: COc1cc(CNS(=O)(=O)c2ccc([N+](=O)[O-])cc2)nc(-c2ccccn2)c1] |
| Compound 75 | 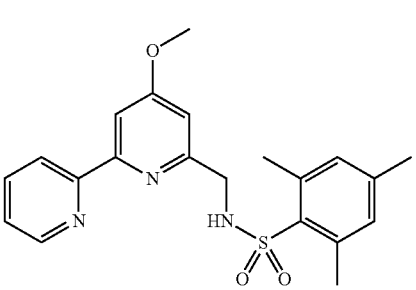 [SMILES: COc1cc(CNS(=O)(=O)c2c(C)cc(C)cc2C)nc(-c2ccccn2)c1] |
| Compound 76 | 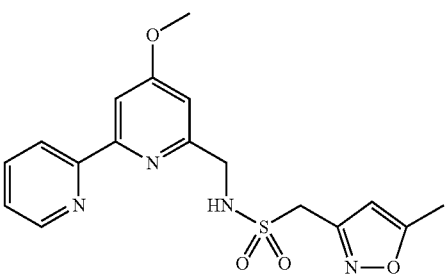 [SMILES: COc1cc(CNS(=O)(=O)Cc2cc(C)on2)nc(-c2ccccn2)c1] |

| Compound | Structure |
|---|---|
| Compound 77 | 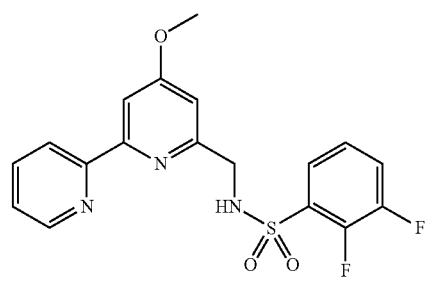 [SMILES: COc1cc(CNS(=O)(=O)c2cccc(F)c2F)nc(-c2ccccn2)c1] |
| Compound 78 | 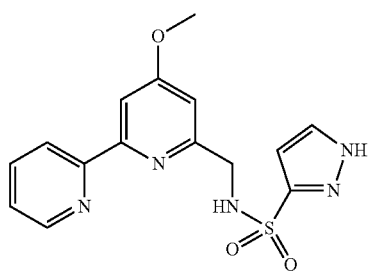 [SMILES: COc1cc(CNS(=O)(=O)c2cc[nH]n2)nc(-c2ccccn2)c1] |
| Compound 79 | 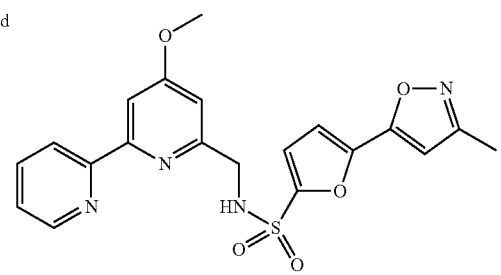 |
| Compound 80 | 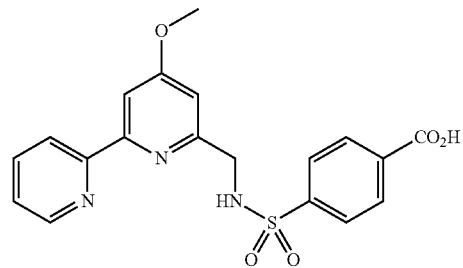 [SMILES: COc1cc(CNS(=O)(=O)c2ccc(C(=O)O)cc2)nc(-c2ccccn2)c1] |
| Compound 81 | 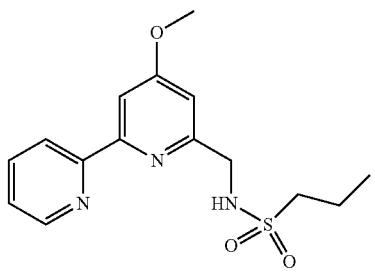 [SMILES: CCCS(=O)(=O)NCc1cc(OC)cc(-c2ccccn2)n1] |
| Compound | Structure |
|---|---|
| Compound 82 | 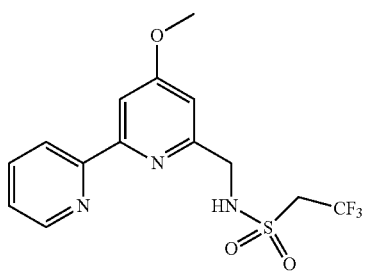 [SMILES: COc1cc(CNS(=O)(=O)CC(F)(F)F)nc(-c2ccccn2)c1] |
| Compound 83 | 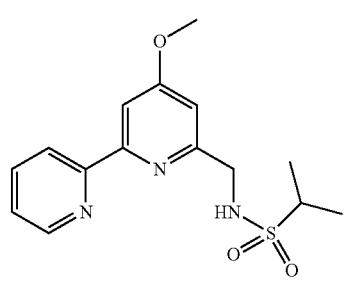 [SMILES: COc1cc(CNS(=O)(=O)C(C)C)nc(-c2ccccn2)c1] |
| Compound 84 | 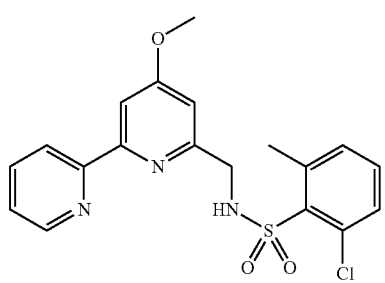 [SMILES: COc1cc(CNS(=O)(=O)c2c(C)cccc2Cl)nc(-c2ccccn2)c1] |
| Compound 85 | 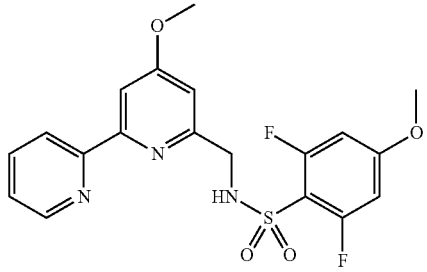 [SMILES: COc1cc(CNS(=O)(=O)c2c(F)cc(OC)cc2F)nc(-c2ccccn2)c1] |
| Compound 86 | 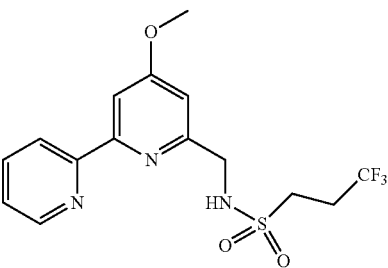 [SMILES: COc1cc(CNS(=O)(=O)CCC(F)(F)F)nc(-c2ccccn2)c1] |

| Compound | Structure |
|---|---|
| Compound 87 | 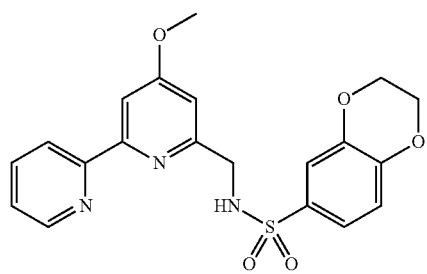 |
| Compound 88 | 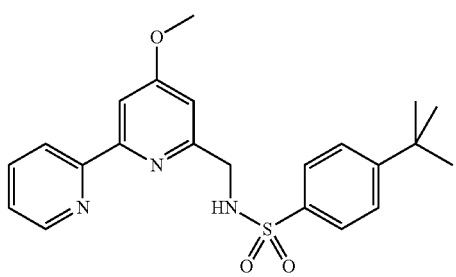 [SMILES: COc1cc(CNS(=O)(=O)c2ccc(C(C)(C)C)cc2)nc(-c2ccccn2)c1] |
| Compound 89 | 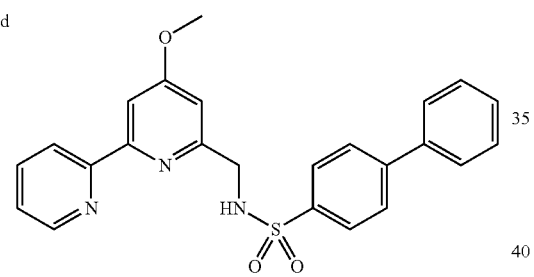 |
| Compound 90 | 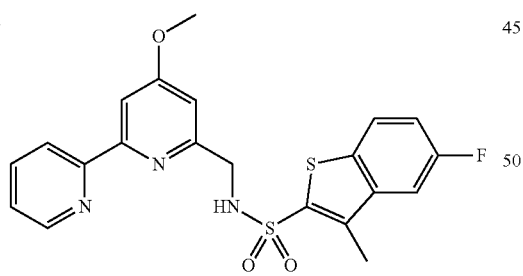 |
| Compound 91 | 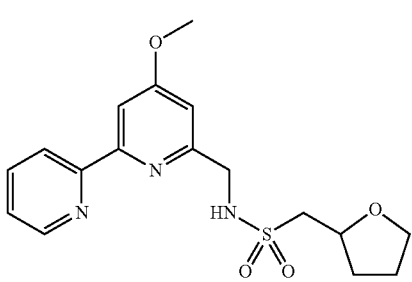 [SMILES: COc1cc(CNS(=O)(=O)CC2CCCO2)nc(-c2ccccn2)c1] |
| Compound | Structure |
|---|---|
| Compound 92 | 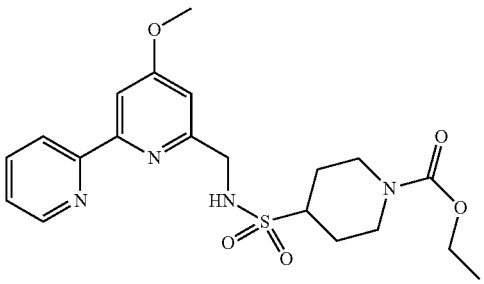 [SMILES: CCOC(=O)N1CCC(S(=O)(=O)NCc2cc(OC)cc(-c3ccccn3)n2)CC1] |
| Compound 93 | 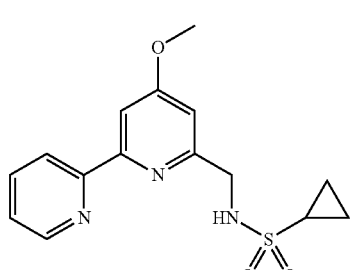 |
| Compound 94 | 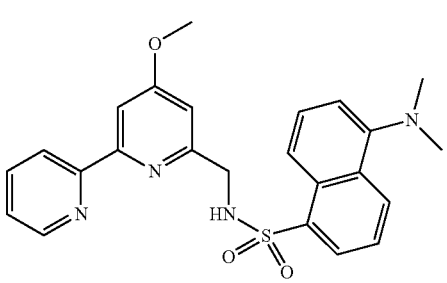 [SMILES: COc1cc(CNS(=O)(=O)c2cccc3c(N(C)C)cccc23)nc(-c2ccccn2)c1] |
| Compound 95 | 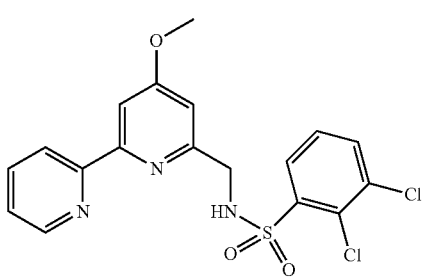 [SMILES: COc1cc(CNS(=O)(=O)c2cccc(Cl)c2Cl)nc(-c2ccccn2)c1] |
| Compound 96 | 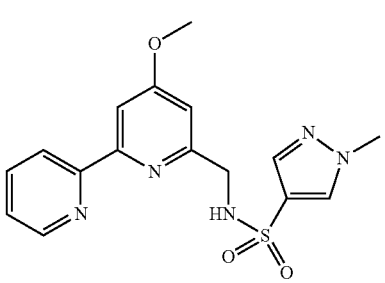 [SMILES: COc1cc(CNS(=O)(=O)c2cnn(C)c2)nc(-c2ccccn2)c1] |

| Compound | Structure |
|---|---|
| Compound 97 | 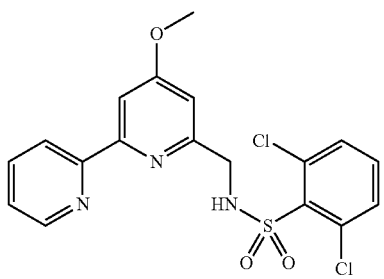 [SMILES: COc1cc(CNS(=O)(=O)c2c(Cl)cccc2Cl)nc(-c2ccccn2)c1] |
| Compound 98 | 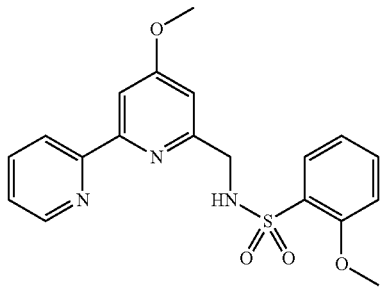 [SMILES: COc1cc(CNS(=O)(=O)c2ccccc2OC)nc(-c2ccccn2)c1] |
| Compound 99 | 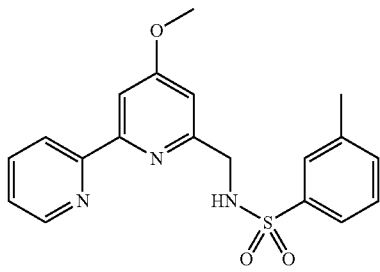 [SMILES: COc1cc(CNS(=O)(=O)c2cccc(C)c2)nc(-c2ccccn2)c1] |
| Compound 100 | 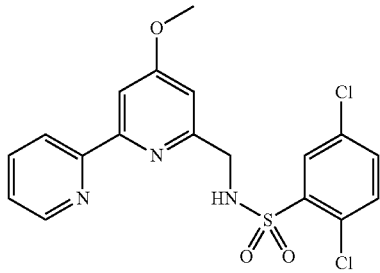 [SMILES: COc1cc(CNS(=O)(=O)c2cc(Cl)ccc2Cl)nc(-c2ccccn2)c1] |
| Compound 101 | 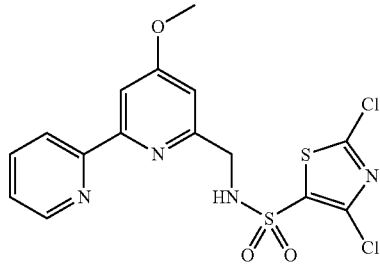 [SMILES: COc1cc(CNS(=O)(=O)c2sc(Cl)nc2Cl)nc(-c2ccccn2)c1] |
| Compound 102 | 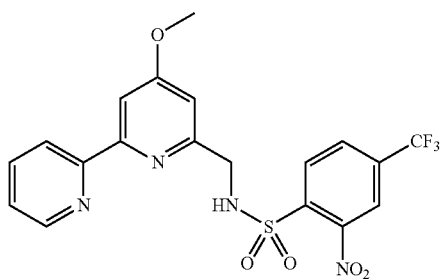 [SMILES: COc1cc(CNS(=O)(=O)c2ccc(C(F)(F)F)cc2[N+](=O)[O-])nc(-c2ccccn2)c1] |
| Compound 103 | 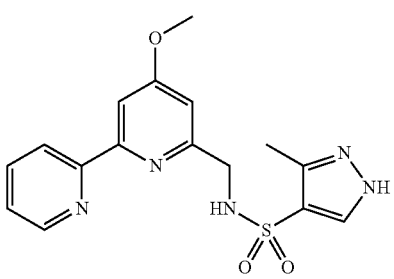 [SMILES: COc1cc(CNS(=O)(=O)c2c[nH]nc2C)nc(-c2ccccn2)c1] |
| Compound 104 | 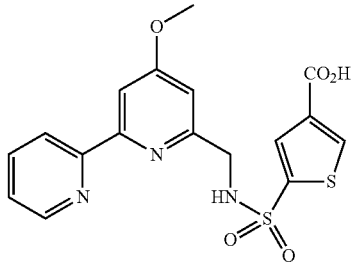 [SMILES: COc1cc(CNS(=O)(=O)c2cc(C(=O)O)cs2)nc(-c2ccccn2)c1] |
| Compound 105 | 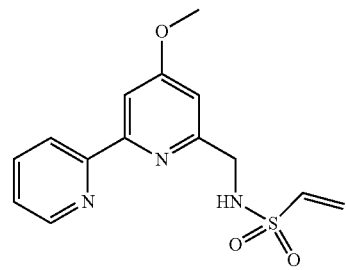 [SMILES: C=CS(=O)(=O)NCc1cc(OC)cc(-c2ccccn2)n1] |
| Compound 106 | 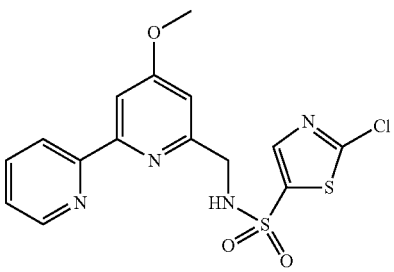 [SMILES: COc1cc(CNS(=O)(=O)c2cnc(Cl)s2)nc(-c2ccccn2)c1] |

| Compound | Structure |
|---|---|
| Compound 107 | 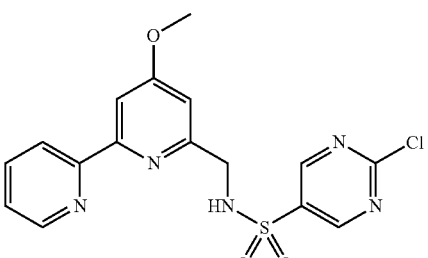 |
| Compound 108 | 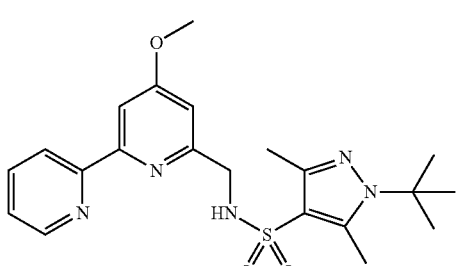 |
| Compound 109 | 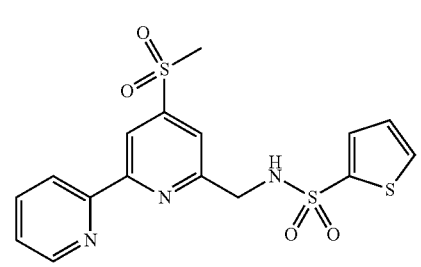 [SMILES: CS(=O)(=O)c1cc(CNS(=O)(=O)c2cccs2)nc(-c2ccccn2)c1] |
| Compound 110 | 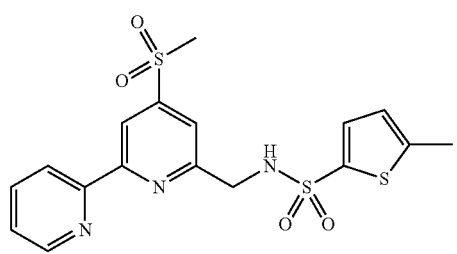 [SMILES: Cc1ccc(S(=O)(=O)NCc2cc(S(C)(=O)=O)cc(-c3ccccn3)n2)s1] |
| Compound 111 | 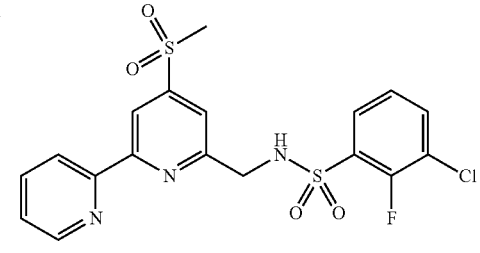 [SMILES: CS(=O)(=O)c1cc(CNS(=O)(=O)c2cccc(Cl)c2F)nc(-c2ccccn2)c1] |

According to a further embodiment, the invention is directed to compounds of formula (IA):

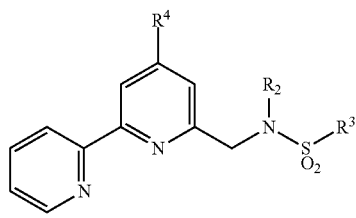

wherein $R^2$, $R^3$ and $R^4$ are as defined above, or a tautomer, salt, solvate or prodrug thereof.

According to a further preferred embodiment, the compounds of Formula (I) are selected from the following:

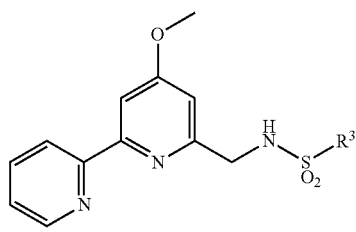

wherein $R^3$ is selected from:

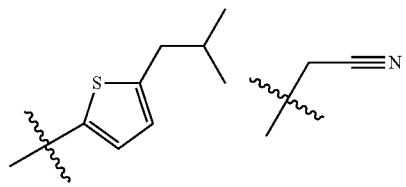

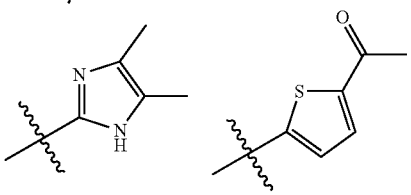

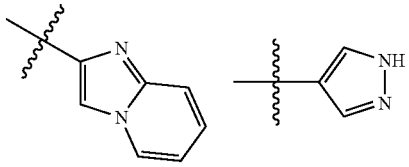

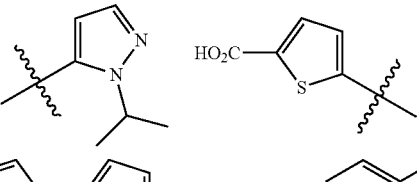

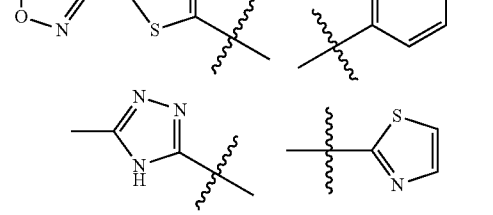

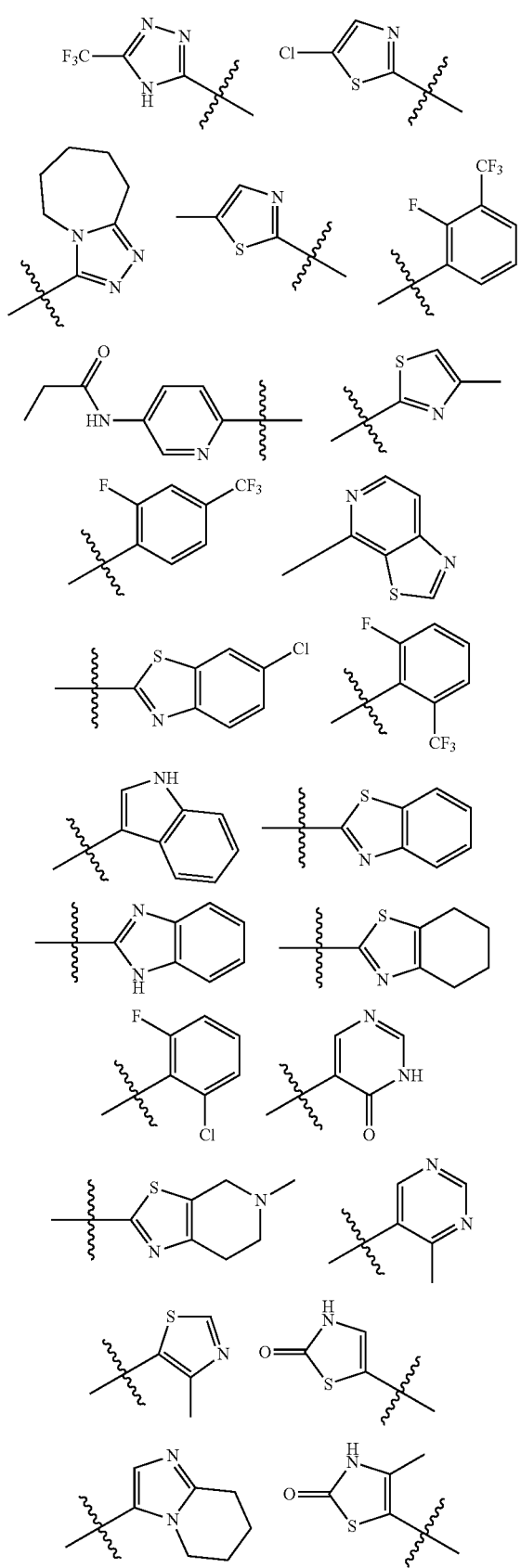
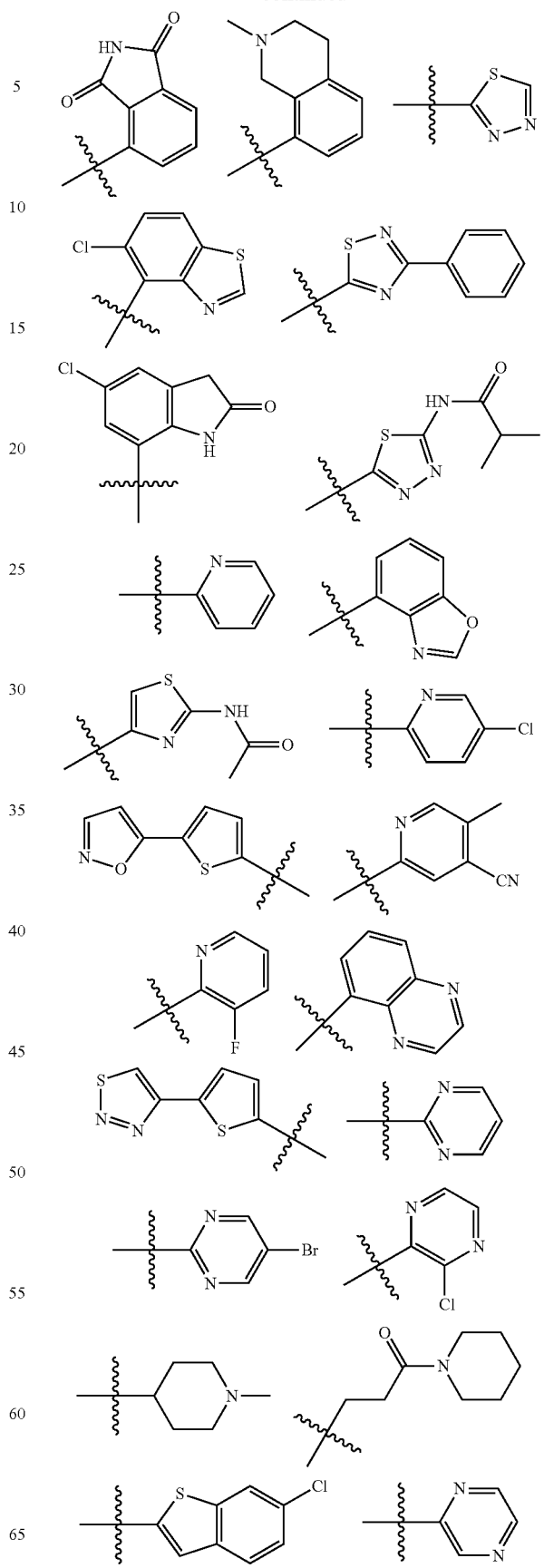

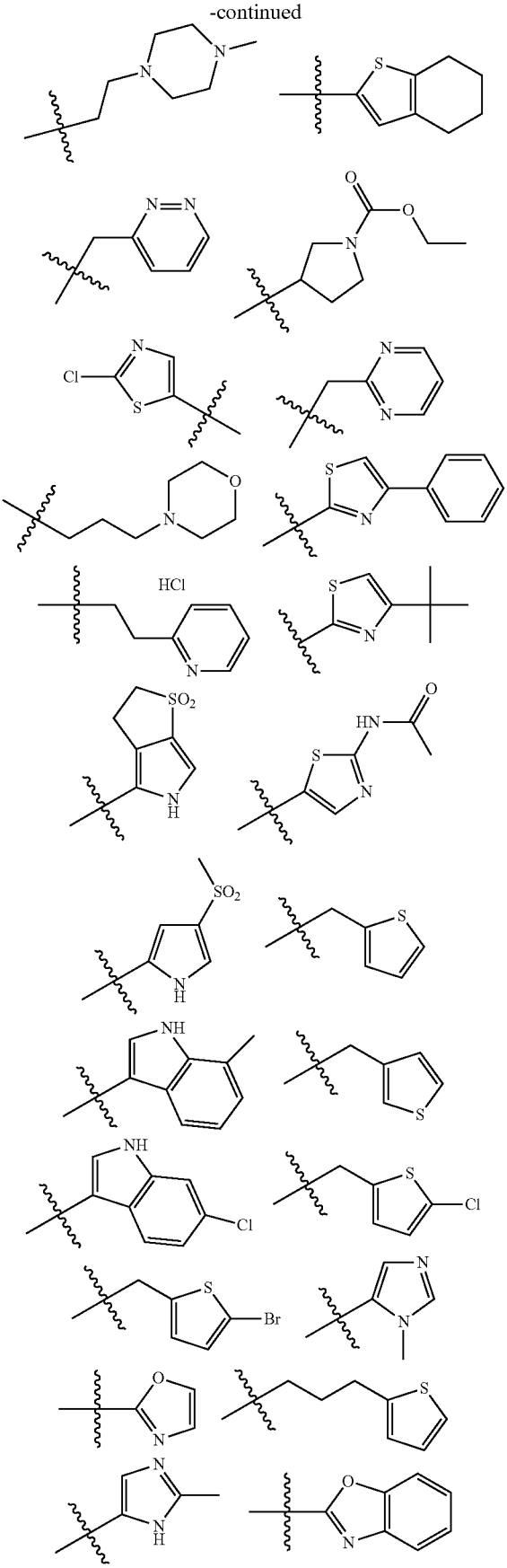
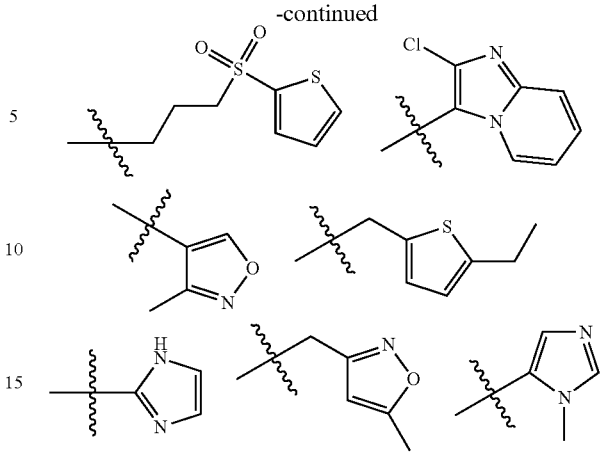

Another aspect of the present invention is a compound of Formula (I), or a tautomer, salt, solvate or prodrug thereof, for use as a medicament.

A further aspect of the present invention refers to a compound of Formula (I), or a tautomer, salt, solvate or prodrug thereof, for use as a medicament for the treatment and/or prophylaxis of a cognitive, neurodegenerative or neuronal disease or disorder, a cardiovascular disease, diabetes or a diabetic complication, a pathology involving ischemia, inflammation or organ transplantation complications due to oxidative stress.

Said cognitive, neurodegenerative or neuronal disease or disorder is preferably selected from Alzheimer's disease, memory loss, attention deficit symptoms associated with Alzheimer's disease, diffuse Lewy body type Alzheimer's disease, disorders associated with cognitive impairment, such as, but not limited to, mild cognitive impairment, Hereditary Cerebral Haemorrhage with Amyloidosis of the Dutch-Type, β-amyloid angiopathy and cerebral bleeding such as cerebral bleeding due to solitary cerebral amyloid angiopathy, vascular cognitive impairment, cerebrovascular dysfunction, prion infections, degenerative dementias, including dementias of mixed vascular and degenerative origin, frontotemporal dementia, pre-senile dementia, senile dementia, AIDS associated dementia, parkinsonian disorders such as Parkinson's disease (PD), subacute sclerosing panencephalis, postencephalitic parkinsonism, dementia pugilistica, guam parkinsonism-dementia complex, Pick's disease, multiple system atrophy (MSA), progressive supranuclear palsy (PSP), and corticobasal degeneration (CBD), Lewy body disease, Huntington's Disease, amyotrophic lateral sclerosis (ALS), multiple sclerosis, neurotraumatic diseases, acute stroke, epilepsy, mood disorders such as depression, schizophrenia and bipolar disorders, promotion of functional recovery post stroke, brain injury, especially traumatic brain injury, stroke and ischemia, Friedreich's Ataxia, Down Syndrome, cognitive loss, pain sensation and trauma.

According to a further preferred embodiment, the cardiovascular disease is selected from hypertension, atherosclerosis, heart failure, angina, myocardial infarction and ischemic heart disease.

According to a further preferred embodiment, the pathology involving ischemia is selected from hepatic ischemia/reperfusion injury, renovascular disease, ischemic nephropathy and retinal diseases.

According to a further preferred embodiment, the retinal disease is selected from diabetic retinopathy, glaucoma, anterior ischemic optic neuropathy, age-related macular degeneration, retinopathy of prematurity.

Inflammation is meant to include chronic inflammatory diseases.

According to a further preferred embodiment, diabetic complication is selected from microvascular and macrovascular changes leading to retinopathy, nephropathy, neuropathy and damage to critical blood vessels, such as the coronary arteries, and the peripheral arterial disease.

The present invention is further related to a pharmaceutical composition comprising at least one of the compounds of Formula (I), or tautomers, salts, solvates or prodrugs thereof, and at least one pharmaceutically acceptable carrier, adjuvant and/or vehicle.

A further aspect of the present invention is a method for the preparation of a compound of Formula (I) as defined above, or a tautomer, salt, solvate or prodrug thereof, comprising mixing a compound of formula:

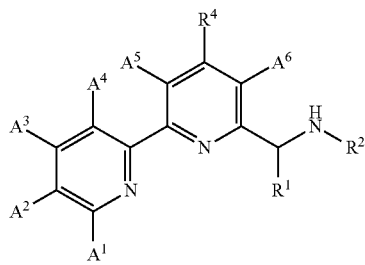

with a sulfonyl chloride of formula $ClSO_2R^3$ in an aprotic or protic solvent wherein $R^1$-$R^4$ and $A^1$-$A^6$ are as defined above.

According to a preferred embodiment, said solvent is an aprotic solvent. Even more preferably, said aprotic solvent is dichloromethane or acetonitrile.

According to an alternative embodiment, said solvent is a protic solvent. Even more preferably, said protic solvent is water or an organic alcohol, e.g. isopropanol.

In a further aspect, the present invention is related to a method of treating and/or preventing a cognitive, neurodegenerative or neuronal disease or disorder, a cardiovascular disease, diabetes or a diabetic complication, a pathology involving ischemia, inflammation or organ transplantation complications due to oxidative stress, which method comprises administering to a patient in need of such a treatment a therapeutically effective amount of at least one compound of Formula (I) or a pharmaceutical composition thereof.

Another aspect of the present invention relates to the use of a compound of formula (I), or a tautomer, salt, solvate or prodrug thereof, in the manufacture of a medicament.

A further aspect of the present invention relates to the use of a compound fo formula (I), or a tautomer, salt, solvate or prodrug thereof, in the manufacture of a medicament for the treatment and/or prophylaxis of a cognitive, neurodegenerative or neuronal disease or disorder, a cardiovascular disease, diabetes or a diabetic complication, a pathology involving ischemia, inflammation or organ transplantation complications due to oxidative stress.

In another aspect, the present invention is related to the use of a compound of Formula (I), or tautomers, salts, solvates or prodrugs thereof, as a reagent in an in vivo biological assay, wherein oxidative stress in cells needs to be inhibited.

In another aspect, the present invention is related to the use of a compound of Formula (I), or tautomers, salts, solvates or prodrugs thereof, as a reagent in an in vivo biological assay, wherein the secretion of soluble amyloid precursor protein-α-secretase needs to be activated.

In another aspect, the present invention is related to the use of a compound of Formula (I), or tautomers, salts, solvates or prodrugs thereof, as a reagent in an in vivo biological assay, wherein beta-amyloid secretion needs to be inhibited.

The compounds of the invention may comprise asymmetric substituents, which may give raise to the presence of different stereoisomers (enantiomer, stereoisomers, etc). Also different isomers may arise depending on the presence of multiple bonds (e.g. Z, E). The single isomers, enantiomers or diastereoisomers and mixtures thereof fall within the scope of the present invention.

The compounds of the invention may be in the form of tautomers, in the form of salts, preferably pharmaceutically acceptable salts, in the form of solvates or in the form of prodrugs.

The term "pharmaceutically acceptable salts" refers to salts which, upon administration to the recipient are capable of providing (directly or indirectly) a compound as described herein. The preparation of salts can be carried out by methods known in the art. Preferably, "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulfonate and p-toluenesulfonate. Examples of the alkali addition salts include inorganic salts such as, for example, sodium, potassium, calcium, ammonium, magnesium, aluminium and lithium salts, and organic alkali salts such as, for example, ethylenediamine, ethanolamine, N,N-dialkylenethanolamine, triethanolamine, glucamine and basic aminoacids salts.

The term "prodrug" as used in this application is defined here as meaning a chemical compound having undergone a chemical derivation such as substitution or addition of a further chemical group to change (for pharmaceutical use) any of its physico-chemical properties, such as solubility or bioavailability, e.g. ester and ether derivatives of an active compound that yield the active compound per se after administration to a subject. Examples of well known methods of producing a prodrug of a given acting compound are known to those skilled in the art and can be found e.g. in Krogsgaard-Larsen et al., Textbook of Drug design and Discovery, Taylor & Francis (April 2002).

Particularly favoured prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

The term "solvate" according to this invention is to be understood as meaning any form of the active compound according to the invention which has another molecule (most likely a polar solvent) attached to it via a non-covalent bonding. Examples of such solvates include hydrates and alcoholates, e.g. methanolates.

The preparation of salts, solvates and prodrugs can be carried out by methods known in the art. It will be appreciated that non-pharmaceutically acceptable salts, solvates or prodrugs also fall within the scope of the invention since those may be useful in the preparation of pharmaceutically acceptable salts, solvates or prodrugs.

The compounds of the invention may be in crystalline form either as free compounds or as solvates (e.g. hydrates) and it is intended that both forms are within the scope of the present invention. Methods of solvation are generally known within the art. Suitable solvates are pharmaceutically acceptable solvates. In a particular embodiment the solvate is a hydrate.

The compounds of the present invention may exhibit tautomerism. Tautomers are one of two or more structural isomers of a compound that exist in equilibrium and are readily converted from one isomeric form to another. Common tautomeric pairs are amine-imine, amide-imidic acid, keto-enol, lactam-lactim, etc. For example, the compounds of the present invention may be equally represented as an Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by a 13C- or 14C-enriched carbon or 15N-enriched nitrogen are within the scope of this invention.

Generally a "therapeutically effective amount" of the compound of the invention or a pharmaceutical composition thereof will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The term "treatment" or "to treat" in the context of this specification means administration of a compound or formulation according to the invention to prevent, ameliorate or eliminate the disease or one or more symptoms associated with said disease. "Treatment" also encompasses preventing, ameliorating or eliminating the physiological sequalae of the disease.

The term "ameliorate" in the context of this invention is understood as meaning any improvement on the situation of the patient treated—either subjectively (feeling of or on the patient) or objectively (measured parameters).

The compounds used in the present invention may be used with at least one other drug to provide a combination therapy. The at least other drug may be part of the composition, or be provided as a separate composition for administration at the same time or at different time. According to one embodiment, the at least other drug is a compound useful for the treatment and/or prophylaxis of cognitive, neurodegenerative or neuronal diseases or disorders. According to another embodiment, the at least other drug is selected from the group comprising beta secretase inhibitors or modulators including BACE1 protein inhibitors, amyloid beta-protein inhibitors, including immunoglobulins, anti-amyloid monoclonal antibodies and vaccines, amyloid beta-protein precursor inhibitors, gamma secretase inhibitors or modulators, muscarinic receptor modulators, acetylcholinesterase inhibitors, butyrilcholinesterase inhibitors, Choline acetyltransferase stimulants, HMG-CoA reductase inhibitors, non-steroidal anti-inflammatory agents, cyclo-oxygenase 2 inhibitors, N-methyl-D-aspartate receptor antagonists, vitamin E, nicotinic acetylcholine receptor modulators, serotonin receptor modulators, cannabinoid receptor agonists, CB1 receptor inverse agonists or CB1 receptor antagonists, AMPA receptor modulators, GABA receptor modulators, inhibitors of amyloid aggregation, glycogen synthase kinase beta inhibitors, promoters of alpha secretase activity, phosphodiesterase 9A and 10 inhibitors, type 4 cyclic nucleotide phosphodiesterase inhibitors, estrogen and cholesterol absorption inhibitors, 11-beta hydroxysteroid dehydrogenase type 1 inhibitors, adenosine receptor antagonists, adrenergic receptor modulators, advanced glycosylation end-product receptor antagonists, alpha-synuclein inhibitors, antioxidants, free radical scavengers, apolipoprotein A stimulants, apolipoprotein E agonists, apoptosis inhibitors, calcium channel modulators, Sodium channel modulators, calpain inhibitors, cathepsin B inhibitors, cell-replacements including stem-cell-therapies, glial cell line-derived neurotrophic factor agonists, nerve growth factor stimulants, chelating agents, complement factor D inhibitors, cyclic AMP response element-binding protein stimulants, D amino acid oxidase inhibitors, dopamine receptor agonists and dopamine uptake inhibitors, endopeptidase inhibitors, fibroblast growth factor stimulants, G protein-coupled receptor antagonists, gene expression stimulants, glucose stimulants, metabotropic glutamate receptor modulators, histamine H3 receptor antagonists or inverse agonists, histone deacetylase inhibitors, mitochondrial-permeability-transition-pore-modulators, monoamine oxidase B inhibitors, neuropeptide stimulants, neurotransmitter modulators, plasminogen activator inhibitor-1 inhibitors, protein kinase C stimulants, rho-associated kinase inhibitors, ribonucleotide reductase inhibitors, signal transduction pathway inhibitors, superoxide dismutase stimulants, tau protein modulators, tubulin polymerisation promoters, toll-like receptor agonists, transglutaminase inhibitors and Wnt protein modulators.

Pharmaceutical Compositions

The term "carrier, adjuvant and/or vehicle" in the pharmaceutical compositions according to the present invention, refers to molecular entities or substances with which the active ingredient is administered. Such pharmaceutical carriers, adjuvants or vehicles can be sterile liquids, such as water and oils, including those of petroleum, animal, vegetable or synthetic origin, such as peanut oil, soybean oil, mineral oil, sesame oil and the like, excipients, disgregants, wetting agents or diluents. Suitable pharmaceutical carriers are described in "Remington's Pharmaceutical Sciences" by E. W. Martin.

According to one embodiment, the pharmaceutical composition may further contain a therapeutically effective amount of one or more compounds useful for the treatment and/or prophylaxis of cognitive, neurodegenerative or neuronal diseases or disorders. According to another embodiment, the pharmaceutical composition may further contain a therapeutically effective amount of one or more compounds selected from the group defined above for combination therapy. Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form because of the convenience for the patient and the chronic character of many of the diseases to be treated. Suitable dosage forms for oral administration may be tablets or capsules and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

EXAMPLES

Synthesis of the Compounds

Compounds of Formula (I) according to the present invention were prepared following the general strategy detailed below.

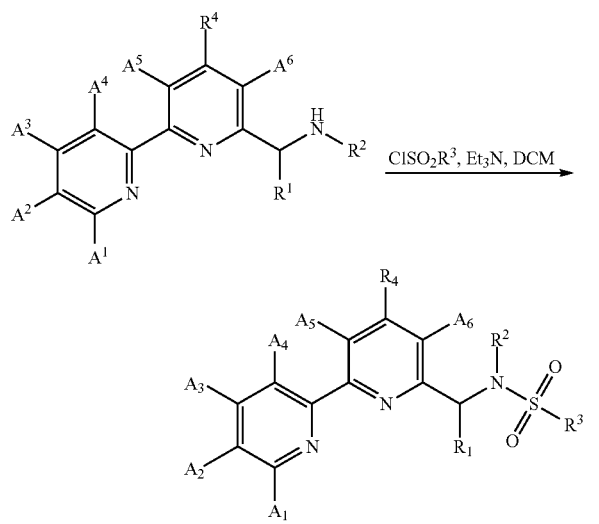

Substituents $A^1$-$A^6$ and $R^1$, $R^2$, $R^3$ are as defined above. They are generally introduced into the compound before transforming the amine —NH—$R^2$ to the final sulfonamide compound. A chemist could design the necessary reactions to introduce such substituents.

For example, substituent $R^4$ is introduced into the compound before such transformation into the sulfonamide. In the following, a few particular preparations, for different meanings of $R^4$, are detailed:

$R^4$=OMe:

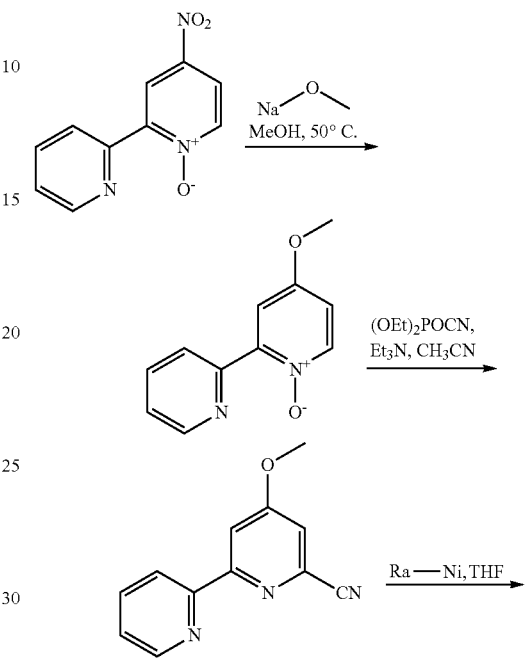

$R^4$=—O—(CH$_2$)$_2$—N—(CH$_2$CH$_3$)$_2$

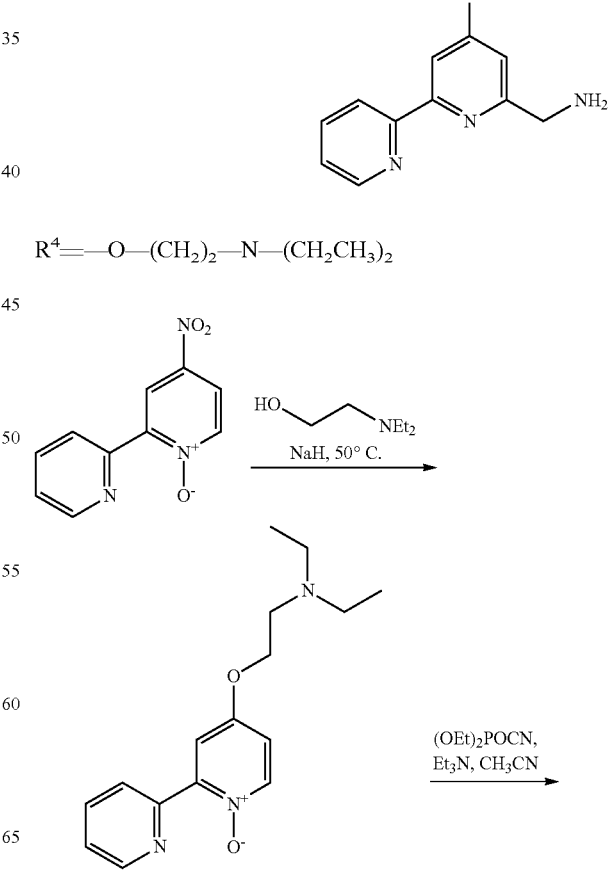

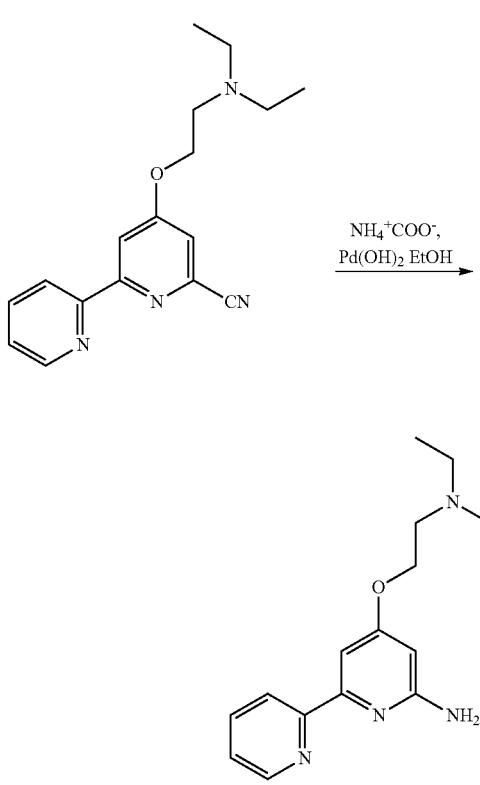

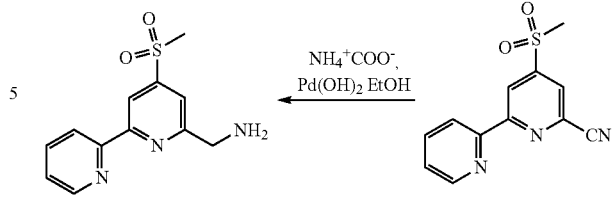

The starting compound in the above preparations, i.e. 4-Nitro-[2,2']bipyridinyl 1-oxide, may be obtained from commercial products following the disclosures, for example, of the following publications:

Acta Chemica Scandinavica 1998, 52, 77-85: Norrby, T. et al, "*Regioselective Functionalization of 2,2'-Bipyridine and Transformations into Unsymmetric Ligands for Coordination Chemistry*"

Journal of Organic Chemistry 1965, 30, 288-290: Corey, E. J. et al, "*Transformations in the 1,10-Phenanthroline Series*".

Said publications are herewith incorporated by reference into the present patent.

In the following, the particular syntheses of compounds of Formula (I) are described. All the reagents used, unless otherwise indicated, are commercially available.

Example 1

Synthesis of Compound 11

4-Fluoro-N-(4-methoxy-[2,2']bipyridinyl-6-ylmethyl)-benzenesulfonamide

Step 1:

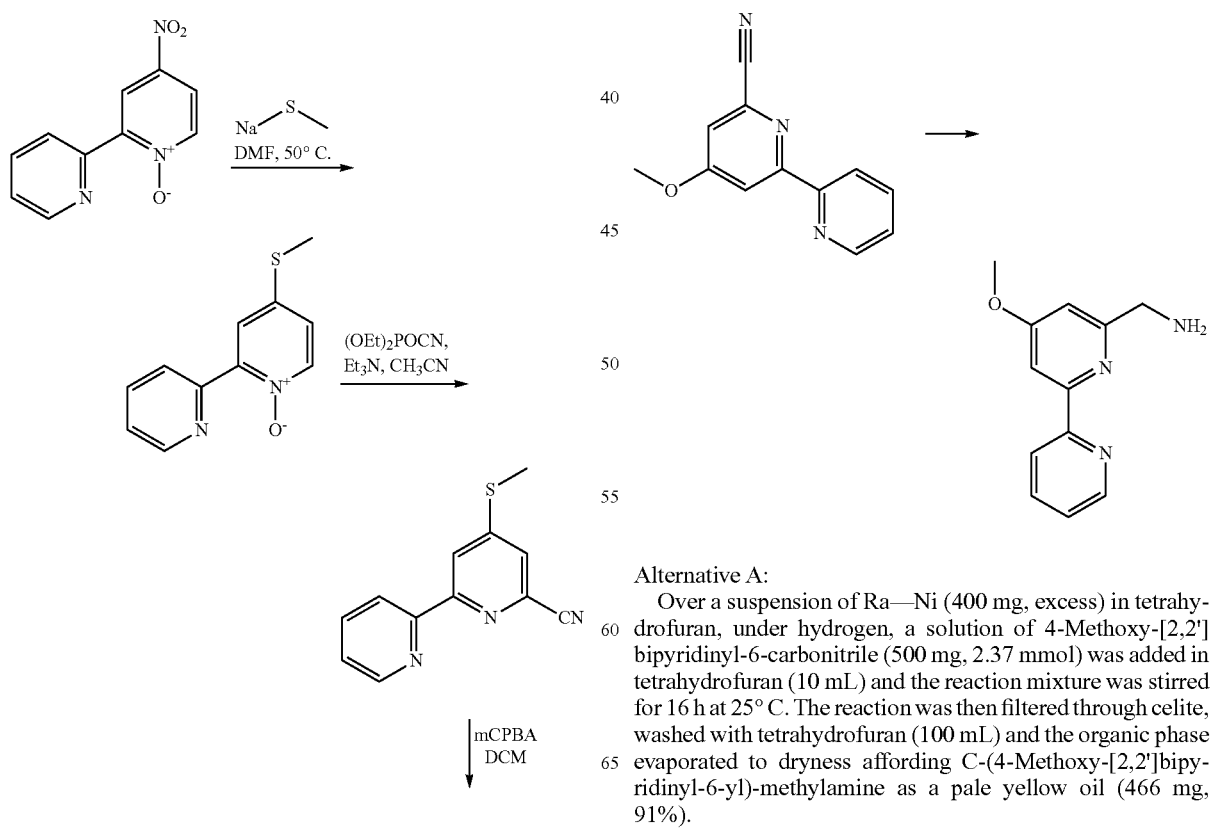

Alternative A:

Over a suspension of Ra—Ni (400 mg, excess) in tetrahydrofuran, under hydrogen, a solution of 4-Methoxy-[2,2']bipyridinyl-6-carbonitrile (500 mg, 2.37 mmol) was added in tetrahydrofuran (10 mL) and the reaction mixture was stirred for 16 h at 25° C. The reaction was then filtered through celite, washed with tetrahydrofuran (100 mL) and the organic phase evaporated to dryness affording C-(4-Methoxy-[2,2']bipyridinyl-6-yl)-methylamine as a pale yellow oil (466 mg, 91%).

Alternative B:

Over a solution of 4-Methoxy-[2,2']bipyridinyl-6-carbonitrile (5.0 g, 23.7 mmol) in tetrahydrofuran (25 mL), a 1.0 M solution of LiAlH$_4$ in tetrahydrofuran (75 mL, 75.0 mmol) was slowly added and the reaction mixture was stirred for 2 h at 25° C. The reaction was then cooled to 0° C., water (2.5 mL) followed by a 15% aqueous solution of NaOH (2.5 mL) were slowly added and stirred at 25° C. for 16 hours. The reaction mixture was filtered through celite, washed with tetrahydrofuran and the organic solvent removed under reduced pressure. The aqueous residue was extracted with dichloromethane, the organic solvent dried with sodium sulphate anhydrous, filtered and removed under reduced pressure to afford C-(4-Methoxy-[2,2']bipyridinyl-6-yl)-methylamine as an orange oil (3.5 g, aprox 68%) that was used in the next step without purification.

Alternative C:

A mixture of 4-Methoxy-[2,2']bipyridinyl-6-carbonitrile (1.0 g, 4.73 mmol), Palladium hydroxide-Pd 20%-50% in water (0.66 g, excess), ammonium formate (1.5 g, excess) and ethanol (60 mL) was stirred at 27° C. for 2 hours. The reaction was then filtered thorough celite, washed with methanol (150 mL) and dichloromethane (150 mL) and the organic phase evaporated to dryness affording C-(4-Methoxy-[2,2']bipyridinyl-6-yl)-methylamine as an orange oil (0.80 g, 45%, in a ratio 72 to 28 product vs. byproduct).

m/z: [ES+] 215 [M+1]

1H NMR: (400 MHz, CDCl$_3$) 3.78 (3H, s, CH$_3$), 3.85 (2H, s, CH$_2$), 6.66 (1H, d, ArH), 7.15 (1H, ddd, ArH), 7.66 (1H, dt, ArH), 8.31 (1H, d, ArH), 8.53 (1H, d, ArH), NH$_2$ missing.

Step 2:

A mixture of C-(4-Methoxy-[2,2']bipyridinyl-6-yl)-methylamine (62.0 mg, 0.29 mmol), triethylamine (55.1 µL, 0.43 mmol), 4-Fluoro-benzenesulfonyl chloride (72.0 mg, 0.371 mmol) and dichloromethane (3 mL) was stirred at 25° C. for 2 hours. The reaction mixture was concentrated under reduced pressure and the crude purified by column chromatography on silica gel (0-100% Ethyl acetate in Hexane) to afford 4-Fluoro-N-(4-methoxy-[2,2']bipyridinyl-6-ylmethyl)-benzenesulfonamide as a white solid (48.1 mg, 38%).

m/z: [ES+] 374 [M+1]

1H NMR: (400 MHz, CDCl$_3$) 3.89 (3H, s, CH$_3$), 4.28 (2H, d, CH$_2$), 6.24 (1H, br s, NH), 6.64 (1H, s, ArH), 7.01-7.07 (2H, m, ArH), 7.34 (1H, ddd, ArH), 7.79-7.89 (4H, m, ArH), 8.28 (1H, d, ArH), 8.66 (1H, d, ArH).

Example 2

Synthesis of Compound 12

3-Fluoro-N-(4-methoxy-[2,2']bipyridinyl-6-ylmethyl)-benzenesulfonamide

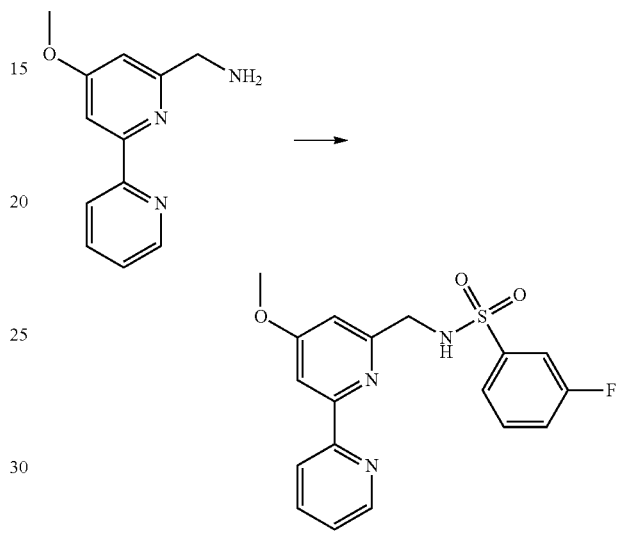

The title compound was prepared following the procedure described for the synthesis of Compound 11 (Example 1), but using 3-fluoro-benzenesulfonyl chloride in the last step. 3-Fluoro-N-(4-methoxy-[2,2']bipyridinyl-6-ylmethyl)-benzenesulfonamide was obtained as a white solid (60.8 mg, 48%).

m/z: [ES+] 374 [M+1]

1H NMR: (400 MHz, CDCl$_3$) 3.85 (3H, s, CH$_3$), 4.28 (2H, d, CH$_2$), 6.31 (1H, m, NH), 6.63 (1H, s, ArH), 7.12 (1H, t, ArH), 7.28-7.36 (2H, m, ArH), 7.56 (1H, d, ArH), 7.63 (1H, d, ArH), 7.75-7.80 (2H, m, ArH), 8.24 (1H, d, ArH), 8.63 (1H, d, ArH).

Example 3

Synthesis of Compound 13

4-Cyano-N-(4-methoxy-[2,2']bipyridinyl-6-ylmethyl)-benzenesulfonamide

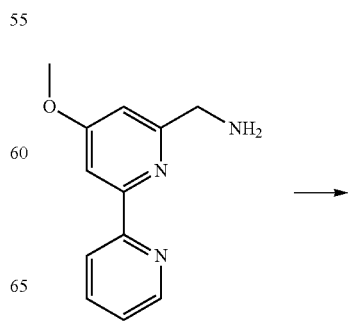

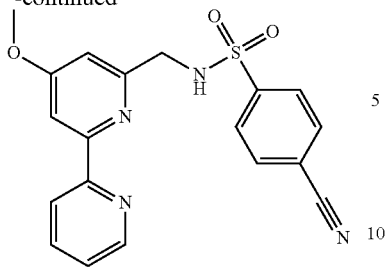

The title compound was prepared following the procedure described for the synthesis of Compound 11 (Example 1), but using 4-cyano-benzenesulfonyl chloride in the last step. 4-Cyano-N-(4-methoxy-[2,2']bipyridinyl-6-ylmethyl)-benzenesulfonamide was obtained as a white solid (63.0 mg, 49%).

m/z: [ES+] 381 [M+1]

1H NMR: (400 MHz, CDCl$_3$) 3.81 (3H, s, CH$_3$), 4.21 (2H, s, CH$_2$), 6.67 (1H, s, ArH), 7.32 (1H, dd, ArH), 7.49-7.54 (3H, m, ArH), 7.78-7.83 (3H, m, ArH), 8.03 (1H, d, ArH), 8.58 (1H, d, ArH), NH missing.

Example 4

Synthesis of Compound 14

3-Cyano-4-fluoro-N-(4-methoxy-[2,2']bipyridinyl-6-ylmethyl)-benzenesulfonamide

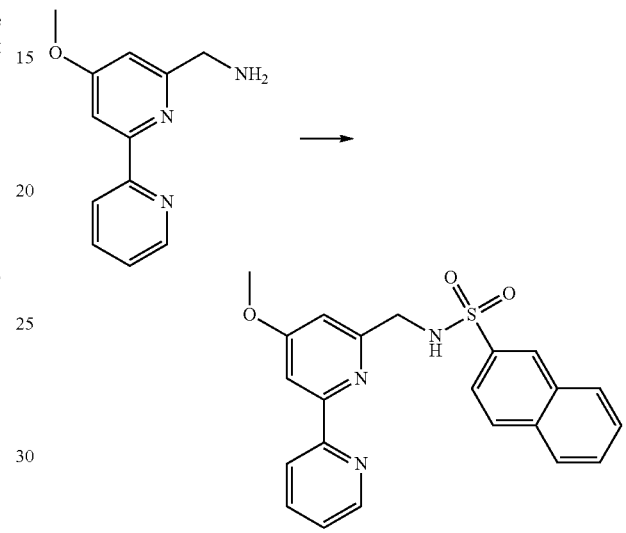

The title compound was prepared following the procedure described for the synthesis of Compound 11 (Example 1), but using 3-Cyano-4-fluoro-benzenesulfonyl chloride in the last step. 3-Cyano-4-fluoro-N-(4-methoxy-[2,2']bipyridinyl-6-ylmethyl)-benzenesulfonamide was obtained as a white solid (75.8 mg, 56%).

m/z: [ES+] 399 [M+1]

1H NMR: (400 MHz, CDCl$_3$) 3.88 (3H, s, CH$_3$), 4.29 (2H, s, CH$_2$), 6.68 (1H, s, ArH), 7.06 (1H, t, ArH), 7.36 (1H, dd, ArH), 7.56 (1H, s, ArH), 7.84 (1H, t, ArH), 7.98 (1H, m, ArH), 8.03-8.06 (2H, m, ArH), 8.65 (1H, d, ArH), NH missing.

Example 5

Synthesis of Compound 15

Naphthalene-2-sulfonic acid (4-methoxy-[2,2']bipyridinyl-6-ylmethyl)-amide

The title compound was prepared following the procedure described for the synthesis of Compound 11 (Example 1), but using naphthalene-2-sulfonyl chloride in the last step. Naphthalene-2-sulfonic acid (4-methoxy-[2,2']bipyridinyl-6-ylmethyl)-amide was obtained as a white solid (46.3 mg, 34%).

m/z: [ES+] 406 [M+1]

1H NMR: (400 MHz, CDCl$_3$) 3.78 (3H, s, CH$_3$), 4.36 (2H, d, CH$_2$), 6.66 (1H, s, ArH), 6.96 (1H, br s, NH), 7.41 (1H, dd, ArH), 7.48-7.56 (2H, m, ArH), 7.59 (1H, s, ArH), 7.72 (2H, t, ArH), 7.82 (2H, t, ArH), 7.90 (1H, t, ArH), 8.30 (1H, d, ArH), 8.40 (1H, s, ArH), 8.69 (1H, d, ArH).

Example 6

Synthesis of Compound 16

4-Bromo-N-(4-methoxy-[2,2']bipyridinyl-6-ylmethyl)-benzenesulfonamide

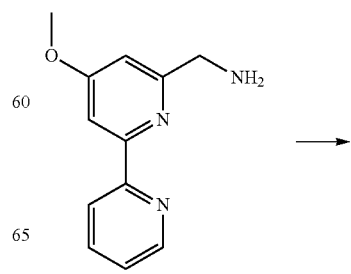

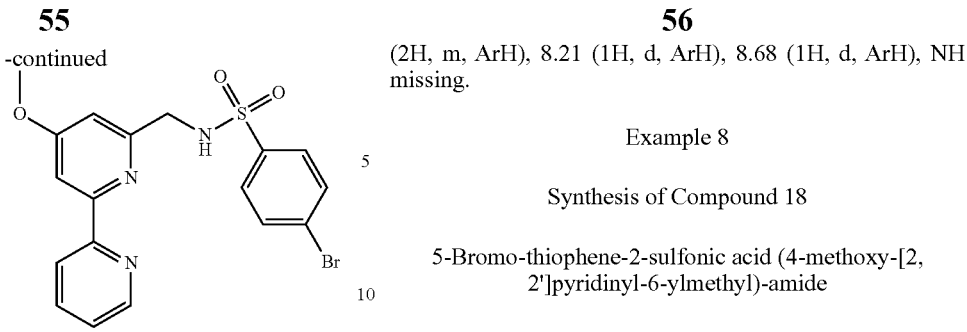

The title compound was prepared following the procedure described for the synthesis of Compound 11 (Example 1), but using 4-bromo-benzenesulfonyl chloride in the last step. 4-Bromo-N-(4-methoxy-[2,2']bipyridinyl-6-ylmethyl)-benzenesulfonamide was obtained as a white solid (92.1 mg, 63%).

m/z: [ES+] 433, 435 [M+1]

1H NMR: (400 MHz, CDCl$_3$) 3.90 (3H, s, CH$_3$), 4.27 (2H, d, CH$_2$), 6.14 (1H, br s, NH), 6.61 (1H, s, ArH), 7.34 (1H, dd, ArH), 7.50 (2H, d, ArH), 7.70 (2H, d, ArH), 7.82 (2H, t, ArH), 8.25 (1H, d, ArH), 8.66 (1H, d, ArH).

Example 7

Synthesis of Compound 17

C,C,C-Trifluoro-N-(4-methoxy-[2,2']bipyridinyl-6-ylmethyl)-methanesulfonamide

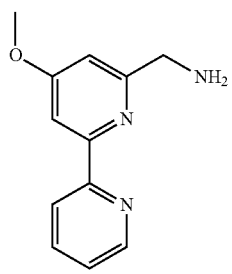  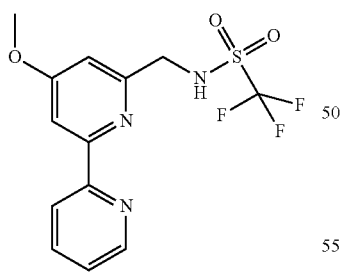

The title compound was prepared following the procedure described for the synthesis of Compound 11 (Example 1), but using trifluoro-methanesulfonyl chloride in the last step. C,C,C-Trifluoro-N-(4-methoxy-[2,2']bipyridinyl-6-ylmethyl)-methanesulfonamide was obtained as a white solid (59.0 mg, 47%).

m/z: [ES+] 348 [M+1]

1H NMR: (400 MHz, CDCl$_3$) 3.92 (3H, s, CH$_3$), 4.53 (2H, s, CH$_2$), 6.70 (1H, s, ArH), 7.35 (1H, dd, ArH), 7.78-7.82 (2H, m, ArH), 8.21 (1H, d, ArH), 8.68 (1H, d, ArH), NH missing.

Example 8

Synthesis of Compound 18

5-Bromo-thiophene-2-sulfonic acid (4-methoxy-[2,2']pyridinyl-6-ylmethyl)-amide

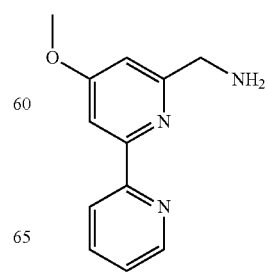 

The title compound was prepared following the procedure described for the synthesis of Compound 11 (Example 1), but using 5-bromo-thiophene-2-sulfonyl chloride in the last step. 5-Bromo-thiophene-2-sulfonic acid (4-methoxy-[2,2']bipyridinyl-6-ylmethyl)-amide was obtained as a white solid (96.2 mg, 61%).

m/z: [ES+] 440, 442 [M+1]

1H NMR: (400 MHz, CDCl$_3$) 3.93 (3H, s, CH$_3$), 4.38 (2H, d, CH$_2$), 6.74 (1H, s, ArH), 6.77 (1H, br s, NH), 6.89 (1H, d, NH), 7.32 (1H, d, ArH), 7.41 (1H, dd, ArH), 7.81 (1H, s, ArH), 7.92 (1H, t, ArH), 8.34 (1H, d, ArH), 8.71 (1H, d, ArH).

Example 9

Synthesis of Compound 19

2,5-Dichloro-thiophene-3-sulfonic acid (4-methoxy-[2,2']pyridinyl-6-ylmethyl)-amide -continued

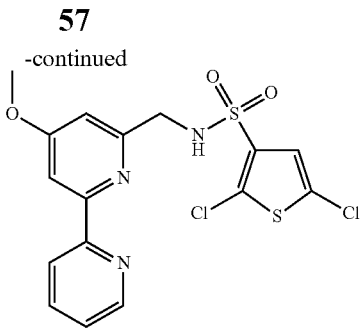

The title compound was prepared following the procedure described for the synthesis of Compound 11 (Example 1), but using 2,5-dichloro-thiophene-3-sulfonyl chloride in the last step. 2,5-Dichloro-thiophene-3-sulfonic acid (4-methoxy-[2,2']bipyridinyl-6-ylmethyl)-amide was obtained as a colourless oil (46.9 mg, 38%).

m/z: [ES+] 430, 432 [M+1]

1H NMR: (400 MHz, CDCl$_3$) 3.93 (3H, s, CH$_3$), 4.37 (2H, d, CH$_2$), 6.36 (1H, br s, NH), 6.68 (1H, s, ArH), 7.07 (1H, s, ArH), 7.34 (1H, dd, ArH), 7.83 (1H, t, ArH), 7.86 (1H, s, ArH), 8.34 (1H, d, ArH), 8.67 (1H, d, ArH).

Example 10

Synthesis of Compound 20

Morpholine-4-sulfonic acid (4-methoxy-[2,2']bipyridinyl-6-ylmethyl)-amide

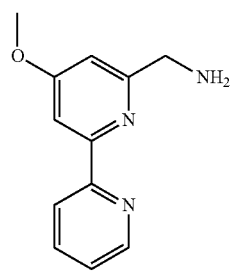
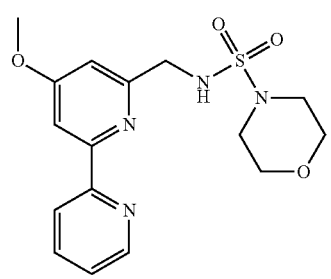

The title compound was prepared following the procedure described for the synthesis of Compound 11 (Example 1), but using morpholine-4-sulfonyl chloride in the last step. Morpholine-4-sulfonic acid (4-methoxy-[2,2']bipyridinyl-6-ylmethyl)-amide was obtained as a white solid (23.8 mg, 23%).

m/z: [ES+] 365 [M+1]

1H NMR: (400 MHz, CDCl$_3$) 3.21 (4H, m, CH$_2$), 3.64 (4H, m, CH$_2$), 3.96 (3H, s, CH$_3$), 4.37 (2H, d, CH$_2$), 5.86 (1H, br s, NH), 6.78 (1H, s, ArH), 7.33 (1H, dd, ArH), 7.83 (1H, t, ArH), 7.92 (1H, s, ArH), 8.37 (1H, d, ArH), 8.67 (1H, d, ArH).

Example 11

Synthesis of Compound 21

Pyridine-3-sulfonic acid (4-methoxy-[2,2']bipyridinyl-6-ylmethyl)-amide

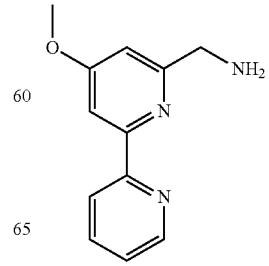

The title compound was prepared following the procedure described for the synthesis of Compound 11 (Example 1), but using pyridine-3-sulfonyl chloride in the last step. Pyridine-3-sulfonic acid (4-methoxy-[2,2']bipyridinyl-6-ylmethyl)-amide was obtained as a yellow solid (18.4 mg, 18%).

m/z: [ES+] 357 [M+1]

1H NMR: (400 MHz, CDCl$_3$) 3.86 (3H, s, CH$_3$), 4.29 (2H, s, CH$_2$), 6.36 (1H, br s, NH), 6.73 (1H, s, ArH), 7.26 (1H, dd, ArH), 7.36 (1H, dd, ArH), 7.58 (1H, s, ArH), 7.07-8.13 (2H, m, ArH), 8.55 (1H, d, ArH), 8.63 (1H, d, ArH), 8.97 (1H, s, ArH), NH missing.

Example 12

Synthesis of Compound 22

4-Methanesulfonyl-N-(4-methoxy-[2,2']bipyridinyl-6-ylmethyl)-benzenesulfonamide

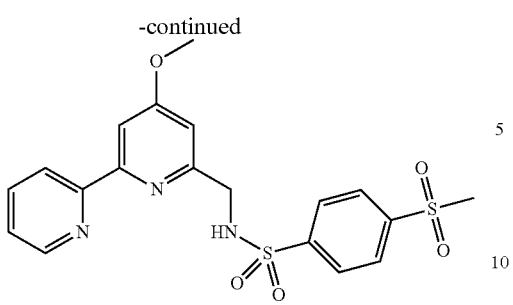

The title compound was prepared following the procedure described for the synthesis of Compound 11 (Example 1), but using 4-methanesulfonyl-benzenesulfonyl chloride in the last step. 4-Methanesulfonyl-N-(4-methoxy-[2,2']bipyridinyl-6-ylmethyl)-benzenesulfonamide was obtained as a white solid (62.6 mg, 50%).

m/z: [ES+] 434 [M+1]

1H NMR: (400 MHz, CDCl$_3$) 2.95 (3H, s, CH$_3$), 3.88 (3H, s, CH$_3$), 4.34 (2H, s, CH$_2$), 6.67 (1H, s, ArH), 7.41 (1H, dd, ArH), 7.58 (1H, s, ArH), 7.80 (2H, d, ArH), 7.90 (1H, t, ArH), 7.98 (2H, d, ArH), 8.14 (1H, d, ArH), 8.69 (1H, d, ArH), NH missing.

Example 13

Synthesis of Compound 23

N-(4-Methoxy-[2,2']bipyridinyl-6-ylmethyl)-C-(4-trifluoromethyl-phenyl)-methanesulfonamide

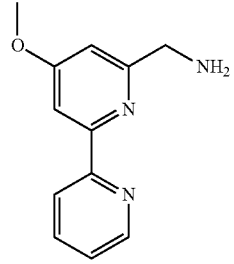

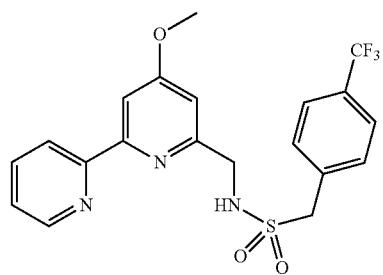

The title compound was prepared following the procedure described for the synthesis of Compound 11 (Example 1), but using (4-trifluoromethyl-phenyl)-methanesulfonyl chloride in the last step. N-(4-Methoxy-[2,2']bipyridinyl-6-ylmethyl)-C-(4-trifluoromethyl-phenyl)-methanesulfonamide was obtained as a white solid (67.3 mg, 53%).

m/z: [ES+] 438 [M+1]

1H NMR: (400 MHz, CDCl$_3$) 3.94 (3H, s, CH$_3$), 4.30-4.32 (4H, m, CH$_2$), 5.90 (1H, br s, NH), 6.70 (1H, s, ArH), 7.33 (1H, dd, ArH), 7.41 (2H, d, ArH), 7.49 (2H, d, ArH), 7.77 (1H, t, ArH), 7.91 (1H, s, ArH), 8.21 (1H, d, ArH), 8.66 (1H, d, ArH).

Example 14

Synthesis of Compound 24

5-Methyl-thiophene-2-sulfonic acid (4-methoxy-[2,2']bipyridinyl-6-ylmethyl)-amide The title compound was prepared following the procedure described for the synthesis of Compound 11 (Example 1), but using 5-methyl-thiophene-2-sulfonyl chloride in the last step. 5-Methyl-thiophene-2-sulfonic acid (4-methoxy-[2,2']bipyridinyl-6-ylmethyl)-amide was obtained as a light yellow solid (45.0 mg, 37%).

m/z: [ES+] 376 [M+1]

1H NMR: (400 MHz, CDCl$_3$) 2.41 (3H, s, CH$_3$), 3.93 (3H, s, CH$_3$), 4.36 (2H, d, CH$_2$), 6.22 (1H, br s, NH), 6.62 (1H, s, CH$_3$), 7.34-7.39 (2H, m, ArH), 7.86 (2H, m, ArH), 8.37 (1H, d, ArH), 8.68 (1H, d, ArH).

Example 15

Synthesis of Compound 1

2,5-Dimethoxy-N-(4-methoxy-[2,2']bipyridinyl-6-ylmethyl)-benzenesulfonamide

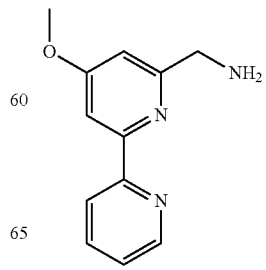

-continued

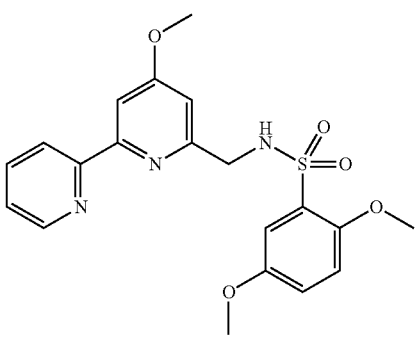

The title compound was prepared following the procedure described for the synthesis of Compound 11 (Example 1), but using 2,5-dimethoxy-benzenesulfonyl chloride in the last step. 2,5-Dimethoxy-N-(4-methoxy-[2,2']bipyridinyl-6-ylmethyl)-benzenesulfonamide was obtained as a white solid (53.0 mg, 14%).

m/z: [ES+] 416 [M+1]

1H NMR: (400 MHz, DMSO-$d_6$) 3.65 (3H, s, $CH_3$), 3.70 (3H, s, $CH_3$), 3.84 (3H, s, $CH_3$), 4.21 (2H, d, $CH_2$), 6.92 (1H, d, ArH), 6.96 (1H, d, ArH), 7.02 (1H, dd, ArH), 7.20 (1H, d, ArH), 7.42-7.45 (1H, m, ArH), 7.71 (1H, d, ArH), 7.83 (1H, t, NH), 7.91 (1H, td, ArH), 8.29 (1H, d, ArH), 8.65 (1H, d, ArH).

Example 16

Synthesis of Compound 2

5-Chloro-thiophene-2-sulfonic acid (4-methoxy-[2,2']pyridinyl-6-ylmethyl)-amide

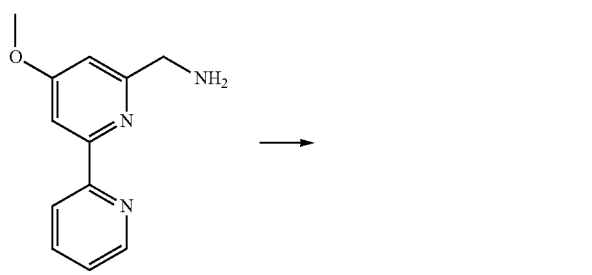

The title compound was prepared following the procedure described for the synthesis of Compound 11 (Example 1), but using 5-chloro-thiophene-2-sulfonyl chloride in the last step. 5-Chloro-thiophene-2-sulfonic acid (4-methoxy-[2,2']bipyridinyl-6-ylmethyl)-amide was obtained as a yellow oil (56.0 mg, 15%).

m/z: [ES+] 396, 398 [M+1]

1H NMR: (400 MHz, DMSO-$d_6$) 3.88 (3H, s, $CH_3$), 4.28 (2H, d, J=6.22 Hz, $CH_2$), 6.95 (1H, d, J=2.13 Hz, ArH), 7.09 (1H, d, J=3.64 Hz, ArH), 7.39 (1H, d, J=3.82 Hz, ArH), 7.45 (1H, dd, J=7.32, 4.84 Hz, ArH), 7.78 (1H, d, J=2.20 Hz, ArH), 7.93 (1H, td, J=7.73, 1.21 Hz, ArH), 8.37 (1H, d, J=7.95 Hz, ArH), 8.66 (1H, d, J=4.71 Hz, ArH), 8.69 (1H, t, J=6.25 Hz, NH).

Example 17

Synthesis of Compound 3

N-(4-Methoxy-[2,2']bipyridinyl-6-ylmethyl)-4-methyl-benzenesulfonamide

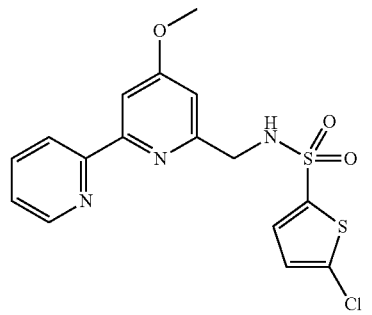

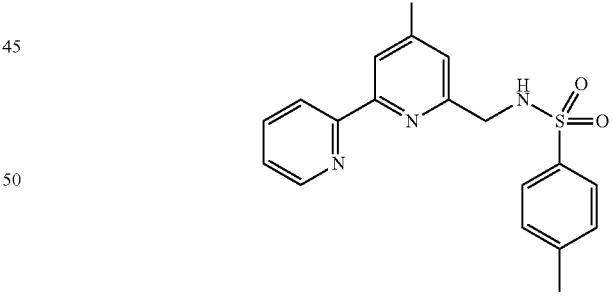

The title compound was prepared following the procedure described for the synthesis of Compound 11 (Example 1), but using 4-methyl-benzenesulfonyl chloride in the last step. N-(4-Methoxy-[2,2']bipyridinyl-6-ylmethyl)-4-methyl-benzenesulfonamide was obtained as a white solid (59.0 mg, 17%).

m/z: [ES+] 370 [M+1]

1H NMR: (400 MHz, DMSO-$d_6$) 2.31 (3H, s, $CH_3$), 3.85 (3H, s, $CH_3$), 4.14 (2H, d, $CH_2$), 6.90 (1H, d, ArH), 7.29 (2H, d, ArH), 7.44 (1H, dd, ArH), 7.67 (2H, d, ArH), 7.75 (1H, d, ArH), 7.91 (1H, td, ArH), 8.21 (1H, t, NH), 8.31 (1H, d, ArH), 8.66 (1H, d, ArH).

Example 18

Synthesis of Compound 4

N-(4-Methoxy-[2,2']bipyridinyl-6-ylmethyl)-4-trifluoromethyl-benzenesulfonamide

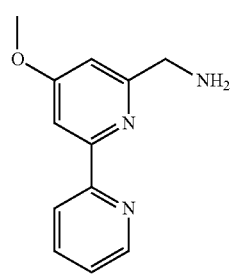

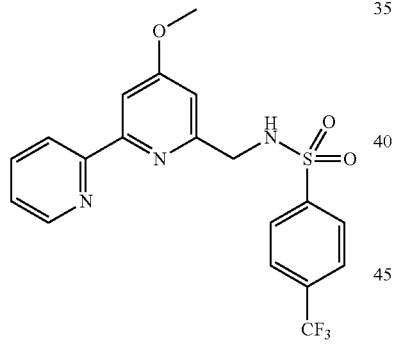

The title compound was prepared following the procedure described for the synthesis of Compound 11 (Example 1), but using 4-trifluoromethyl-benzenesulfonyl chloride in the last step. N-(4-Methoxy-[2,2']bipyridinyl-6-ylmethyl)-4-trifluoromethyl-benzenesulfonamide was obtained as a yellow oil (76.0 mg, 19%).

m/z: [ES+] 424 [M+1]

1H NMR: (400 MHz, DMSO-$d_6$) 3.83 (3H, s, CH$_3$), 4.26 (2H, d, CH$_2$), 6.86 (1H, d, ArH), 7.44 (1H, ddd, ArH), 7.70 (1H, d, ArH), 7.77 (2H, d, ArH), 7.87-7.95 (1H, m, ArH), 7.92 (2H, d, ArH), 8.27 (1H, d, ArH), 8.60 (1H, t, NH), 8.64 (1H, ddd, ArH).

Example 19

Synthesis of Compound 5

N-(4-Methoxy-[2,2']bipyridinyl-6-ylmethyl)-methanesulfonamide

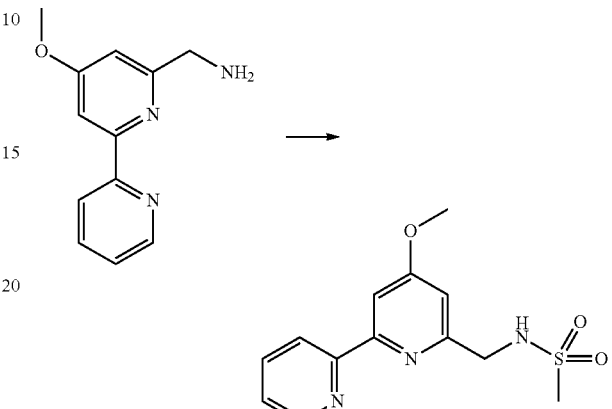

The title compound was prepared following the procedure described for the synthesis of Compound 11 (Example 1), but using methanesulfonyl chloride in the last step. N-(4-Methoxy-[2,2']bipyridinyl-6-ylmethyl)-methanesulfonamide was obtained as a yellow oil (10.0 mg, 4%).

$^1$H NMR: (400 MHz, DMSO-$d_6$) 2.95 (3H, s, CH$_3$), 3.93 (3H, s, CH$_3$), 4.32 (2H, d, CH$_2$), 7.07 (1H, d, ArH), 7.46 (1H, dd, ArH), 7.70 (1H, t, NH), 7.84 (1H, d, ArH), 7.95 (1H, td, ArH), 8.44 (1H, d, ArH), 8.68 (1H, dd, ArH).

Example 20

Synthesis of Compound 6

N-(4-Methoxy-[2,2']bipyridinyl-6-ylmethyl)-benzenesulfonamide

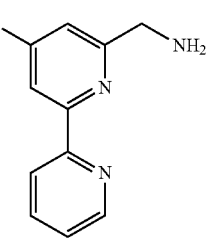

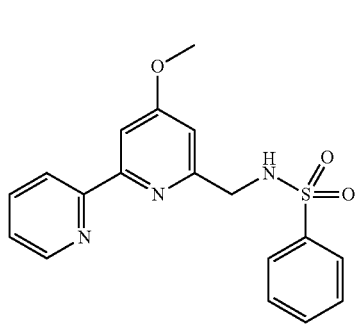

The title compound was prepared following the procedure described for the synthesis of Compound 11 (Example 1), but using benzenesulfonyl chloride in the last step. N-(4-Methoxy-[2,2']bipyridinyl-6-ylmethyl)-benzenesulfonamide was obtained as a yellow oil (8.0 mg, 2%).

m/z: [ES+] 356 [M+1]

1H NMR: (400 MHz, DMSO-d$_6$) 3.85 (3H, s, CH$_3$), 4.18 (2H, d, CH$_2$), 6.91 (1H, d, ArH), 7.44 (1H, dd, ArH), 7.51 (2H, t, ArH), 7.54-7.60 (1H, m, ArH), 7.74 (1H, d, ArH), 7.80 (2H, d, ArH), 7.91 (1H, t, ArH), 8.28-8.35 (2H, m, ArH and NH), 8.65 (1H, d, ArH).

Example 21

Synthesis of Compound 7

Cyclohexanesulfonic acid (4-methoxy-[2,2']bipyridinyl-6-ylmethyl)-amide

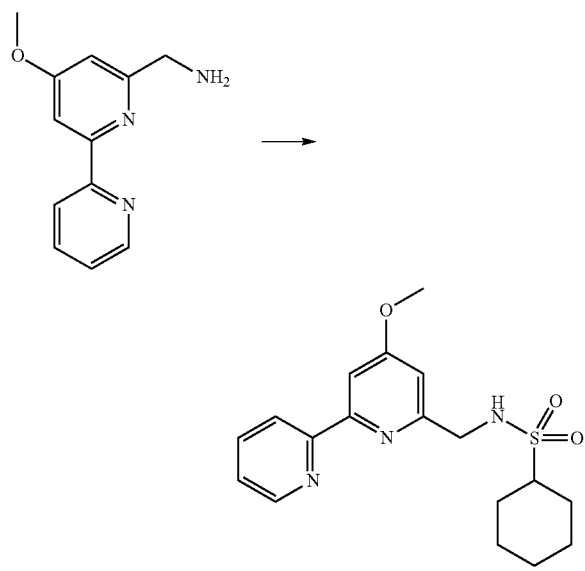

The title compound was prepared following the procedure described for the synthesis of Compound 11 (Example 1), but using cyclohexanesulfonyl chloride in the last step. Cyclohexanesulfonic acid (4-methoxy-[2,2']bipyridinyl-6-ylmethyl)-amide was obtained as a yellow oil (9.0 mg, 3%).

m/z: [ES+] 362 [M+1]

1H NMR: (400 MHz, DMSO-d$_6$) 1.00-1.15 (3H, m, CH$_2$), 1.26-1.39 (2H, m, CH$_2$), 1.49-1.56 (1H, m, CH$_2$), 1.65-1.74 (2H, m, CH$_2$), 2.02 (2H, d, CH$_2$), 2.88 (1H, tt, CH), 3.92 (3H, s, CH$_3$), 4.30 (2H, d, CH$_2$), 7.07 (1H, d, ArH), 7.46 (1H, dd, ArH), 7.69 (1H, t, NH), 7.84 (1H, d, ArH), 7.95 (1H, t, ArH), 8.43 (1H, d, ArH), 8.68 (1H, d, ArH).

Examples 22 and 23

Synthesis of Compounds 28 and 29

Thiophene-2-sulfonic acid [4-(2-diethylamino-ethoxy)-[2,2']bipyridinyl-6-ylmethyl]-amide and Thiophene-2-sulfonic acid bis-[4-(2-diethylamino-ethoxy)-[2,2']pyridinyl-6-ylmethyl]-amide Step 1:

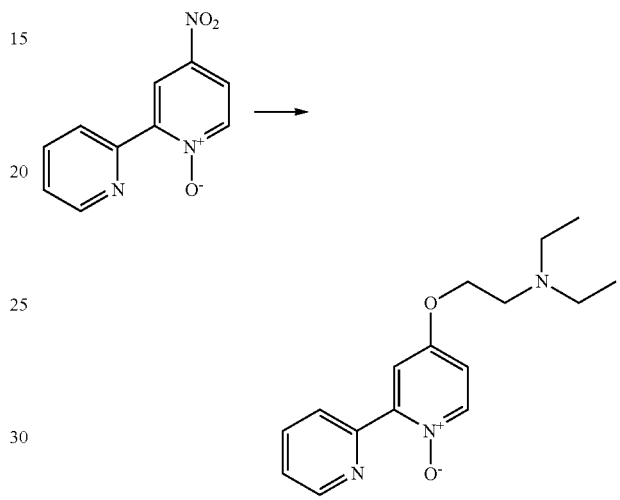

Sodium hydride 60% (3.68 g, 92.0 mmol) was slowly added at 25° C. to 2-Diethylamino-ethanol (50 mL, excess) and stirred for 15 minutes, then 4-Nitro-[2,2']bipyridinyl 1-oxide (10.0 g, 46.0 mmol) was added and the reaction mixture stirred for 2 hours at 50° C. The reaction mixture was concentrated under reduced pressure and the crude was diluted with water (50 mL) and dichloromethane (1 L), washed with a saturated aqueous solution of sodium bicarbonate (3×250 mL), dried with sodium sulphate anhydrous, filtered and concentrated under reduced pressure. The crude was purified by column chromatography on silica gel (2% Methanol in dichloromethane plus 0.2% ammonia in methanol) to afford diethyl-[2-(1-oxy-[2,2']bipyridinyl-4-yloxy)-ethyl]-amine as a dark brown oil (5.75 g, 47%).

$^1$H NMR: (400 MHz, CDCl$_3$) 1.07-1.14 (6H, m, CH$_3$), 2.65-2.75 (4H, m, CH$_2$), 2.91-2.99 (2H, m, CH$_2$), 4.17-4.25 (2H, m, CH$_2$), 6.85 (1H, m, ArH), 7.34 (1H, m, ArH), 7.75 (1H, d, ArH), 7.83 (1H, t, ArH), 8.19 (1H, d, ArH), 8.70 (1H, d, ArH), 9.04 (1H, d, ArH).

Step 2:

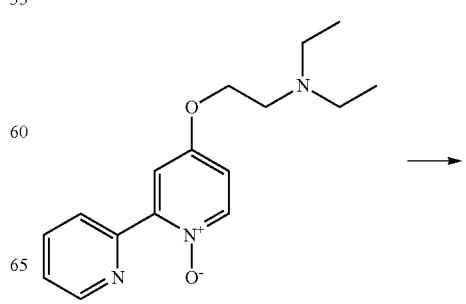

-continued

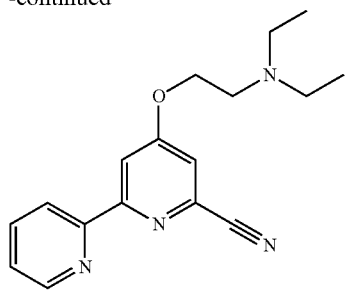

Diethyl cyanophosphonate 90% (10.11 mL, 66.6 mmol) was slowly added at 25° C. to a mixture of Diethyl-[2-(1-oxy-[2,2']bipyridinyl-4-yloxy)-ethyl]-amine (5.75 g, 22.2 mmol) and triethylamine (3.70 mL, 26.6 mmol) in acetonitrile (100 mL) and stirred for 3 hours at 90° C. The reaction mixture was concentrated under reduced pressure and the crude was purified by column chromatography on silica gel (10% Methanol in dichloromethane plus 5% ammonia in methanol) followed by purification in a PoraPak Rxn CX cartridge to afford 4-(2-diethylamino-ethoxy)-[2,2']bipyridinyl-6-carbonitrile as a dark brown oil (3.40 g, 52%).

m/z: [ES+] 297 [M+1]

1H NMR: (400 MHz, CDCl$_3$) 0.99 (6H, t, CH$_3$), 2.56 (4H, q, CH$_2$), 2.84 (2H, t, CH$_2$), 4.14 (2H, t, CH$_2$), 7.13 (1H, s, ArH), 7.26 (1H, m, ArH), 7.75 (1H, t, ArH), 8.09 (1H, s, ArH), 8.32 (1H, d, ArH), 8.57 (1H, d, ArH).

Step 3:

A mixture of 4-(2-Diethylamino-ethoxy)-[2,2']bipyridinyl-6-carbonitrile (1.4 g, 5.22 mmol), Palladium hydroxide-Pd 20%-50% in water (2.25 g, excess), ammonium formate (1.65 g, excess) and ethanol (66 mL) was stirred at 27° C. for 2 hours. The reaction was then filtered thorough celite, washed with methanol (200 mL) and dichloromethane (200 mL) and the organic phase evaporated to dryness affording [2-(6-aminomethyl-[2,2']bipyridinyl-4-yloxy)-ethyl]diethylamine as an orange oil (1.03 g, 30%, in a ratio 1 to 1 product vs. byproduct).

$^1$H NMR: (400 MHz, CDCl$_3$) 1.04 (6H, t, CH$_3$), 2.62 (4H, q, CH$_2$), 2.86 (2H, t, CH$_2$), 3.77 (2H, br s, NH2), 3.97 (2H, s, CH$_2$), 4.17 (2H, t, CH$_2$), 6.78 (1H, s, ArH), 7.23 (1H, m, ArH), 7.68 (1H, m, ArH), 7.80 (1H, m, ArH), 8.40 (1H, m, ArH), 8.61 (1H, d, ArH).

Step 4:

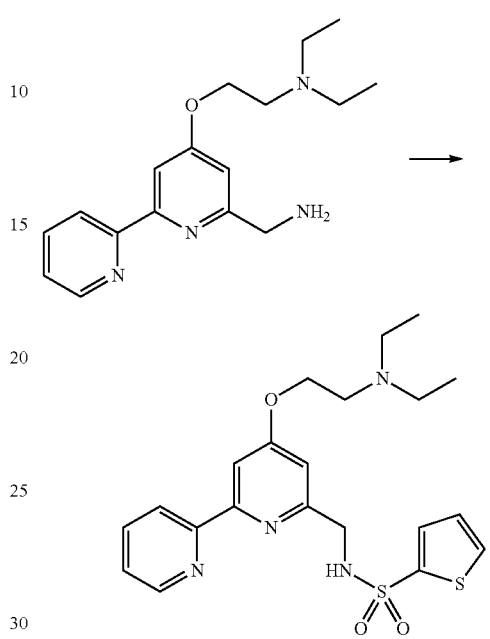

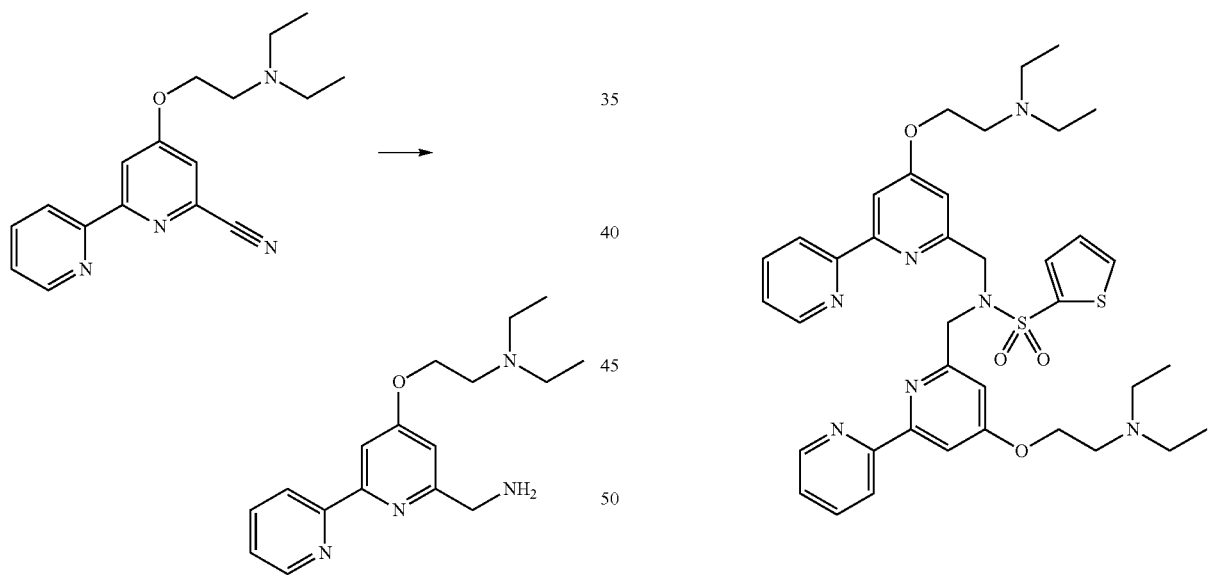

A mixture of [2-(6-Aminomethyl-[2,2']bipyridinyl-4-yloxy)-ethyl]-diethylamine (107 mg, 0.357 mmol), triethylamine (136.5 µL, 1.07 mmol), Thiophene-2-sulfonyl chloride (195.4 mg, 1.07 mmol) and dichloromethane (5 mL) was stirred at 25° C. for 2 hours. The reaction mixture was concentrated under reduced pressure and the crude purified by column chromatography on silica gel (0-10% methanol in dichloromethane) to afford thiophene-2-sulfonic acid [4-(2-diethylamino-ethoxy)-[2,2']bipyridinyl-6-ylmethyl]-amide as a yellow oil (85.0 mg, 53%) and thiophene-2-sulfonic acid bis-[4-(2-diethylamino-ethoxy)-[2,2']bipyridinyl-6-ylmethyl]-amide as a brown oil (58.7 mg, 22%).

Compound 28

Thiophene-2-sulfonic acid [4-(2-diethylamino-ethoxy)-[2,2']bipyridinyl-6-ylmethyl]-amide m/z: [ES+] 447 [M+1]
1H NMR: (400 MHz, CDCl$_3$) 1.11 (6H, t, CH$_3$), 2.72 (4H, q, CH$_2$), 2.97 (2H, t, CH$_2$), 4.22 (2H, t, CH$_2$), 4.34 (2H, s, CH$_2$), 6.36 (1H, br s, NH), 6.71 (1H, s, ArH), 6.96 (1H, m, ArH), 7.30 (1H, dd, ArH), 7.47 (1H, d, ArH), 7.57 (1H, d, ArH), 7.77-7.81 (2H, m, ArH), 8.27 (1H, d, ArH), 8.62 (1H, d, ArH).

Compound 29

Thiophene-2-sulfonic acid bis-[4-(2-diethylamino-ethoxy)-[2,2']bipyridinyl-6-ylmethyl]-amide m/z: [ES+] 730 [M+1]
1H NMR: (400 MHz, CDCl$_3$) 1.15 (12H, t, CH$_3$), 2.80 (8H, q, CH$_2$), 3.03 (4H, t, CH$_2$), 4.21 (4H, t, CH$_2$), 4.67 (4H, s, CH$_2$), 6.79 (2H, s, ArH), 6.90 (1H, m, ArH), 7.19 (2H, dd, ArH), 7.41 (1H, d, ArH), 7.45 (1H, d, ArH), 7.60 (2H, dt, ArH), 7.69 (2H, s, ArH), 8.13 (2H, d, ArH), 8.53 (2H, d, ArH).

Example 24

Synthesis of Compound 30

5-Chloro-thiophene-2-sulfonic acid [4-(2-diethyl-amino-ethoxy)-[2,2']bipyridinyl-6-ylmethyl]-amide

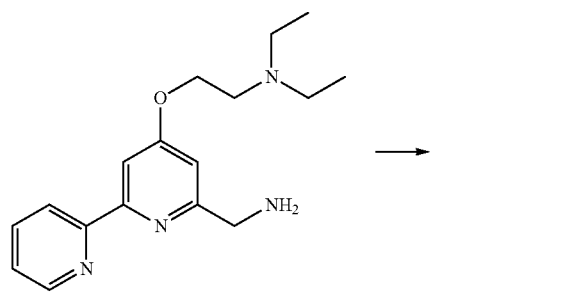

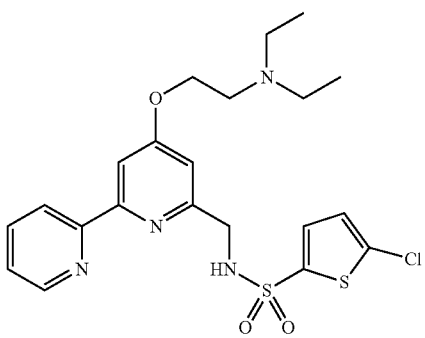

The title compound was prepared following the procedure described for the synthesis of Compound 28 (Examples 22 and 23), but using 5-chloro-thiophene-2-sulfonyl chloride in the last step. 5-Chloro-thiophene-2-sulfonic acid [4-(2-di-ethylamino-ethoxy)-[2,2']bipyridinyl-6-ylmethyl]-amide was obtained as a yellow oil (59.1 mg, 34%).

m/z: [ES+] 481,483 [M+1]
1H NMR: (400 MHz, CDCl$_3$) 1.16 (6H, t, CH$_3$), 2.80 (4H, q, CH$_2$), 3.05 (2H, t, CH$_2$), 4.29 (2H, t, CH$_2$), 4.33 (2H, s, CH$_2$), 6.76 (1H, s, ArH), 7.29 (1H, dd, ArH), 7.33 (1H, s, ArH), 7.76-7.81 (2H, m, ArH), 8.26 (1H, d, ArH), 8.62 (1H, d, ArH), NH missing.

Example 25

Synthesis of Compound 32

5-Methyl-thiophene-2-sulfonic acid [4-(2-diethy-lamino-ethoxy)-[2,2']bipyridinyl-6-ylmethyl]-amide

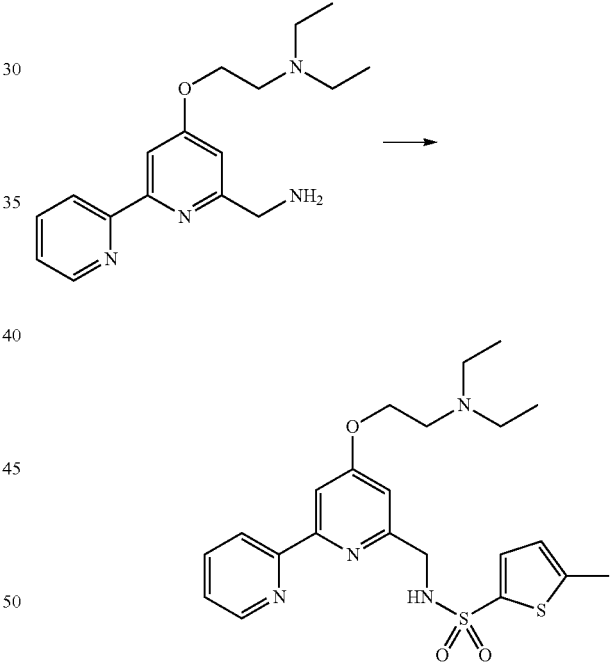

The title compound was prepared following the procedure described for the synthesis of Compound 28 (Examples 22 and 23), but using 5-methyl-thiophene-2-sulfonyl chloride in the last step. 5-Methyl-thiophene-2-sulfonic acid [4-(2-di-ethylamino-ethoxy)-[2,2']bipyridinyl-6-ylmethyl]-amide was obtained as a yellow oil (45.9 mg, 28%).

m/z: [ES+] 461 [M+1]
1H NMR: (400 MHz, CDCl$_3$) 1.11 (6H, t, CH$_3$), 2.39 (3H, s, CH$_3$), 2.73 (4H, q, CH$_2$), 2.98 (2H, t, CH$_2$), 4.23 (2H, t, CH$_2$), 4.31 (2H, s, CH$_2$), 6.20 (1H, br s, NH), 6.61 (1H, d,

ArH), 6.72 (1H, s, ArH), 7.30 (1H, dd, ArH), 7.36 (1H, d, ArH), 7.67-7.82 (2H, m, ArH), 8.29 (1H, d, ArH), 8.63 (1H, d, ArH).

Example 26

Synthesis of Compound 33

5-Chloro-thiophene-2-sulfonic acid (4-methanesulfonyl-[2,2']bipyridinyl-6-ylmethyl)-amide Step 1

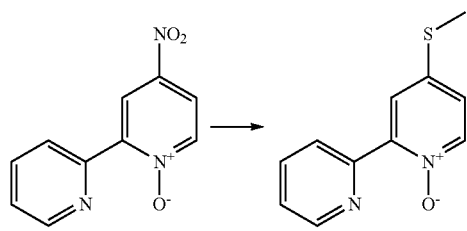 [SMILES: O=[N+]([O-])c1cc[n+]([O-])c(-c2ccccn2)c1 ; CSc1cc[n+]([O-])c(-c2ccccn2)c1]

Sodium thiomethoxide (1.06 g, 15.2 mmol) was added at 25° C. to 4-Nitro-[2,2']bipyridinyl 1-oxide (3.0 g, 13.8 mmol) in dimethyl formamide (15 mL) and stirred for 2 hours at 50° C. The reaction mixture was added into ice (200 g) under vigorous stirring, the solid formed was filtered and washed with water (100 mL) and ether (100 mL), the filtrate was concentrated, diluted with water, extracted with dichloromethane (3×100 mL), dried with anhydrous sodium sulphate, filtered and concentrated under reduced pressure. The crude was purified by column chromatography on silica gel (0-100% Ethyl acetate in Hexane) to afford 4-methylsulfanyl-[2,2']bipyridinyl 1-oxide as a white solid (650.0 mg, 22%).

m/z: [ES+] 2191 [M+1]

1H NMR: (400 MHz, CDCl$_3$) 2.30 (3H, s, CH$_3$), 6.86 (1H, d, ArH), 7.12 (1H, d, ArH), 7.60 (1H, m, ArH), 7.75 (1H, s, ArH), 7.97 (1H, d, ArH), 8.48 (1H, d, ArH), 8.72 (1H, d, ArH).

Step 2:

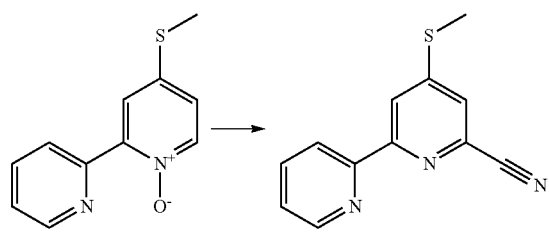 [SMILES: CSc1cc[n+]([O-])c(-c2ccccn2)c1 ; CSc1cc(C#N)nc(-c2ccccn2)c1]

Diethyl cyanophosphonate 90% (1.3 mL, 8.4 mmol) was slowly added at 25° C. to a mixture of 4-Methylsulfanyl-[2, 2']bipyridinyl 1-oxide (650.0 mg, 2.98 mmol) and triethylamine (0.50 mL, 3.58 mmol) in acetonitrile (14 mL) and stirred for 2 hours at 90° C. The reaction mixture was concentrated under reduced pressure, methanol (5 mL) added and the solid formed filtered and washed with methanol (2×5 mL), the filtrate was concentrated and purified by column chromatography on silica gel (0 to 10% Methanol in dichloromethane) to afford 4-methylsulfanyl-[2,2']bipyridinyl-6-carbonitrile as a white solid that was combined with the previous white solid obtained (500.0 mg, 74%).

m/z: [ES+] 228 [M+1]

1H NMR: (400 MHz, CDCl$_3$) 2.59 (3H, s, CH$_3$), 7.36 (1H, dd, ArH), 7.44 (1H, s, ArH), 7.84 (1H, t, ArH), 8.40-8.45 (2H, m, ArH), 8.65 (1H, m, ArH).

Step 3:

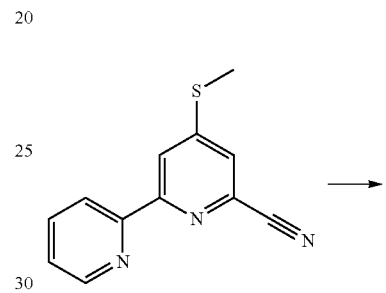

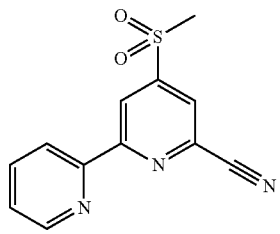

Meta-chloroperboenzoic acid (430 mg, 1.92 mmol) was added at 25° C. to a mixture of 4-Methylsulfanyl-[2,2']bipyridinyl-6-carbonitrile (217 mg, 0.96 mmol) in dichloromethane (3 mL) and stirred for 2 hours at 90° C. The reaction mixture was diluted with dichloromethane (200 mL), washed with a saturated solution of sodium bicarbonate (2×50 mL), saturated solution of sodium carbonate (2×50 mL) and water (2×50 mL), dried with anhydrous sodium sulphate, filtered and concentrated under reduced pressure, methanol (25 mL) was added and the solid formed filtered and washed with methanol (2×15 mL) to afford 4-methanesulfonyl-[2,2']bipyridinyl-6-carbonitrile as a white solid (235.1 mg, 95%).

m/z: [ES+] 260 [M+1]

1H NMR: (400 MHz, DMSO-d$_6$) 3.45 (3H, s, CH$_3$), 7.60 (1H, dd, ArH), 8.04 (1H, t, ArH), 8.40 (1H, d, ArH), 8.65 (1H, s, ArH), 8.79 (1H, d, ArH), 8.99 (1H, s, ArH).

Step 4:

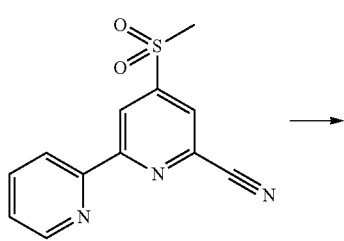

A mixture of 4-Methanesulfonyl-[2,2']bipyridinyl-6-carbonitrile (200.0 g, 0.772 mmol), Palladium hydroxide-Pd 20%-50% in water (2.25 g, excess), ammonium formate (334.0 mg, excess) and ethanol (10 mL) was stirred at 27° C. for 1 hour. The reaction was then filtered thorough celite, washed with methanol (50 mL) and dichloromethane (50 mL) and the filtrate was concentrated and purified by column chromatography on silica gel (0 to 10% Methanol in dichloromethane) to afford C-(4-methanesulfonyl-[2,2']bipyridinyl-6-A-methylamine as a yellow solid (40.0 mg, 20%) that was used in the next step without further purification.

1H NMR: (400 MHz, CDCl$_3$) 3.24 (3H, s, CH$_3$), 4.15 (2H, s, CH$_2$), 7.46 (1H, dd, ArH), 7.90 (1H, s, ArH), 7.94 (1H, t, ArH), 8.51 (1H, d, ArH), 8.66-8.68 (2H, m, ArH), NH$_2$ missing.

Step 5:

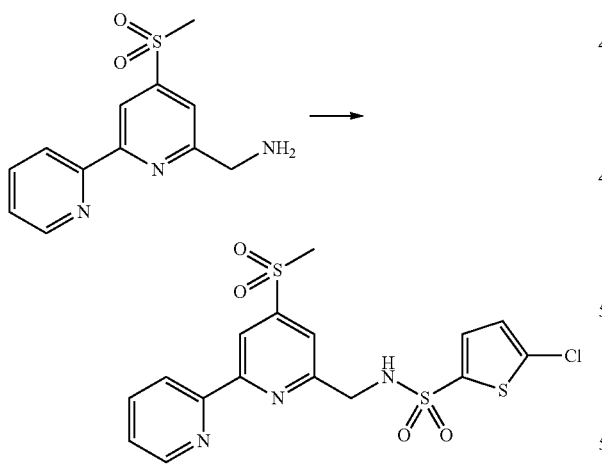

A mixture of C-(4-Methanesulfonyl-[2,2']bipyridinyl-6-yl)-methylamine (40.0 mg, 0.153 mmol), triethylamine (58.0 µL, 0.459 mmol), 5-chlorothiophene-2-sulfonyl chloride (42.0 mg, 0.184 mmol) and DCM (2 mL) was stirred at 25° C. for 2 hours. The reaction mixture was concentrated under reduced pressure and the crude purified by column chromatography on silica gel (0-10% methanol in dichloromethane) to afford 5-chloro-thiophene-2-sulfonic acid (4-methanesulfonyl-[2,2']bipyridinyl-6-ylmethyl)-amide as a white solid (20.0 mg, 30%).

m/z: [ES+] 443, 445, 446 [M+1]

1H NMR: (400 MHz, CDCl$_3$) 3.13 (3H, s, CH$_3$), 4.54 (2H, m, CH$_2$), 6.41 (1H, br s, NH), 6.78 (1H, s, ArH), 7.38 (1H, d, ArH), 7.43 (1H, m, ArH), 7.73 (1H, d, ArH), 7.90 (1H, m, ArH), 8.33 (1H, d, ArH), 8.72-8.75 (2H, m, ArH).

Example 27

Synthesis of Compound 34

2,4-Difluoro-N-(4-methoxy-[2,2']bipyridinyl-6-ylmethyl)-benzenesulfonamide

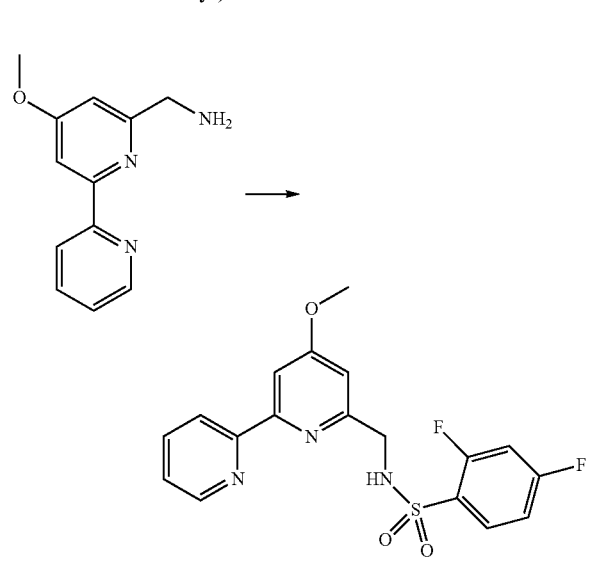

The title compound was prepared following the procedure described for the synthesis of Compound 11 (Example 1), but using 2,4-difluoro-benzenesulfonyl chloride in the last step. 2,4-Difluoro-N-(4-methoxy-[2,2']bipyridinyl-6-ylmethyl)-benzenesulfonamide was obtained as a white solid (93 mg, 80%).

m/z: [ES+] 392 [M+1]

1H NMR: (400 MHz, CDCl$_3$) 3.89 (3H, s, CH$_3$), 4.32 (2H, s, CH$_2$), 6.34 (1H, br s, NH), 6.69 (1H, ddd, ArH), 6.89 (1H, ddd, ArH), 7.34 (1H, ddd, ArH), 7.85 (3H, m, ArH), 8.33 (1H, d, ArH), 8.66 (1H, dd, ArH)

Example 28

Synthesis of Compound 35

5-Methyl-furan-2-sulfonic acid (4-methoxy-[2,2']bipyridinyl-6-ylmethyl)-amide

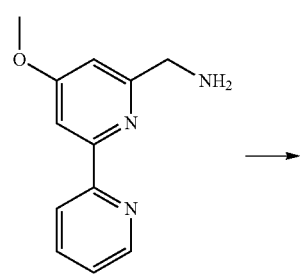

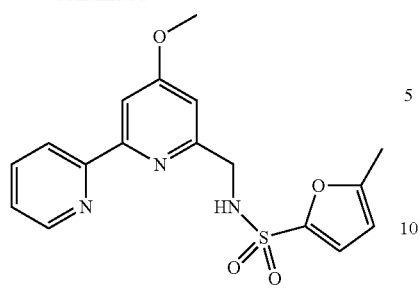

The title compound was prepared following the procedure described for the synthesis of Compound 11 (Example 1), but using 5-methyl-furan-2-sulfonyl chloride in the last step. 5-Methyl-furan-2-sulfonic acid (4-methoxy-[2,2']bipyridinyl-6-ylmethyl)-amide was obtained as a white solid (93 mg, 72%).

m/z: [ES+] 360 [M+1]

1H NMR: (400 MHz, CDCl$_3$) 2.12 (3H, s, CH$_3$), 3.89 (3H, s, CH$_3$), 4.36 (2H, s, CH$_2$), 5.94 (1H, dd, ArH), 6.12 (1H, br s, NH), 6.68 (1H, ddd, ArH), 6.89 (1H, ddd, ArH), 7.33 (1H, ddd, ArH), 7.81 (1H, dd, ArH), 7.85 (1H, dd, ArH), 8.35 (1H, td, ArH), 8.66 (1H, ddd, ArH)

Example 29

Synthesis of Compound 36

4-Methyl-2-oxo-2,3-dihydro-thiazole-5-sulfonic acid (4-methoxy-[2,2']bipyridinyl-6-ylmethyl)-amide

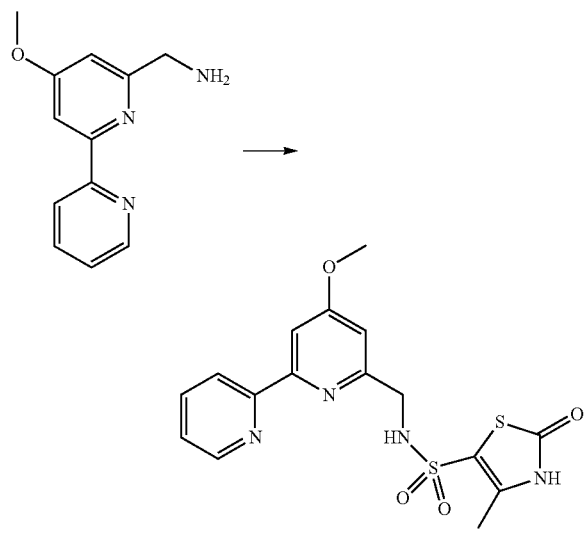

The title compound was prepared following the procedure described for the synthesis of Compound 11 (Example 1), but using 4-methyl-2-oxo-2,3-dihydro-thiazole-5-sulfonyl chloride in the last step. 4-Methyl-2-oxo-2,3-dihydro-thiazole-5-sulfonic acid (4-methoxy-[2,2']bipyridinyl-6-ylmethyl)-amide was obtained as a white solid (83 mg, 74%).

m/z: [ES+] 393 [M+1]

1H NMR: (400 MHz, CDCl$_3$) 2.30 (3H, s, CH$_3$), 3.95 (3H, s, CH$_3$), 4.38 (2H, s, CH$_2$), 6.16 (1H, br s, NH), 6.75 (1H, d, ArH), 7.35 (1H, dd, ArH), 7.84 (1H, dt, ArH), 7.89 (1H, d, ArH), 8.33 (1H, d, ArH), 8.67 (1H, d, ArH), 1 NH missing.

Example 30

Synthesis of Compound 37

2-Methyl-propane-1-sulfonic acid (4-methoxy-[2,2'] bipyridinyl-6-ylmethyl)-amide

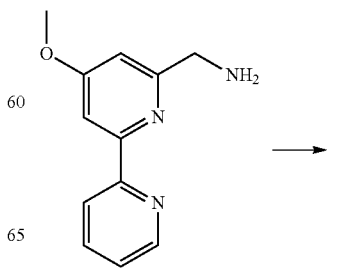

The title compound was prepared following the procedure described for the synthesis of Compound 11 (Example 1), but using 2-methyl-propane-1-sulfonyl chloride in the last step. 2-Methyl-propane-1-sulfonic acid (4-methoxy-[2,2']bipyridinyl-6-ylmethyl)-amide was obtained as a white solid (48 mg, 50%).

m/z: [ES+] 336 [M+1]

1H NMR: (400 MHz, CDCl$_3$) 1.04 (6H, d, CH$_3$), 2.27 (1H, m, CH), 2.92 (2H, d, CH$_2$), 3.95 (3H, s, CH$_3$), 4.42 (2H, s, CH$_2$), 5.68 (1H, br s, NH), 6.80 (1H, d, ArH), 7.32 (1H, ddd, ArH), 7.82 (1H, dt, ArH), 7.91 (1H, d, ArH), 8.37 (1H, d, ArH), 8.66 (1H, dd, ArH)

Example 31

Synthesis of Compound 38

4-Methoxy-N-(4-methoxy-[2,2']bipyridinyl-6-ylmethyl)-benzenesulfonamide

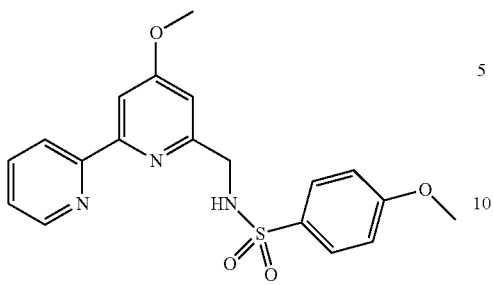

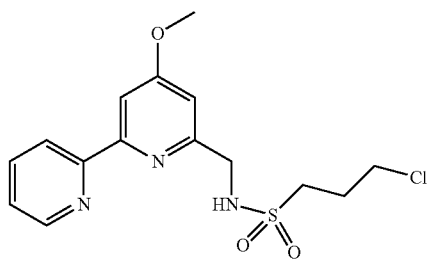

The title compound was prepared following the procedure described for the synthesis of Compound 11 (Example 1), but using 4-methoxy-benzenesulfonyl chloride in the last step. 4-Methoxy-N-(4-methoxy-[2,2']bipyridinyl-6-ylmethyl)-benzenesulfonamide was obtained as a white solid (84 mg, 76%).

m/z: [ES+] 386 [M+1]

1H NMR: (400 MHz, CDCl$_3$) 3.78 (3H, s, CH$_3$), 3.88 (3H, s, CH$_3$), 4.24 (2H, s, CH$_2$), 5.95 (1H, br s, NH), 6.62 (1H, d, ArH), 6.84 (2H, d, ArH), 7.31 (1H, ddd, ArH), 7.80 (4H, m, ArH), 8.29 (1H, d, ArH), 8.64 (1H, ddd, ArH)

The title compound was prepared following the procedure described for the synthesis of Compound 11 (Example 1), but using 3-chloro-propane-1-sulfonyl chloride in the last step. 3-Chloro-propane-1-sulfonic acid (4-methoxy-[2,2']bipyridinyl-6-ylmethyl)-amide was obtained as a white solid (73 mg, 71%).

m/z: [ES+] 356 [M+1]

1H NMR: (400 MHz, CDCl$_3$) 2.28 (2H, td, CH$_2$), 3.18 (2H, t, CH$_2$), 3.58 (2H, t, CH$_2$), 3.96 (3H, s, CH$_3$), 4.44 (2H, d, CH$_2$), 5.72 (1H, t, NH), 6.80 (1H, d, ArH), 7.34 (1H, ddd, ArH), 7.83 (1H, dt, ArH), 7.93 (1H, d, ArH), 8.37 (1H, td, ArH), 8.68 (1H, ddd, ArH)

Example 32

Synthesis of Compound 39

3-Chloro-propane-1-sulfonic acid (4-methoxy-[2,2'] bipyridinyl-6-ylmethyl)-amide

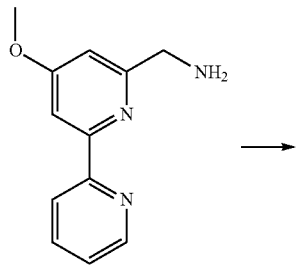

Examples 33 to 101

Further compounds were also prepared following the procedure described for the synthesis of Compound 11 (Example 1) using the appropriate sulfonyl chloride, except for Compound 105, where 2-chloroethanesulfonyl chloride was employed.

In the following table, the yield and the mass spectra data of each of the obtained compounds are indicated:

| | | Structure | Yield (%) | m/z [ES+] |
|---|---|---|---|---|
| Example 33 | Compound 40 | 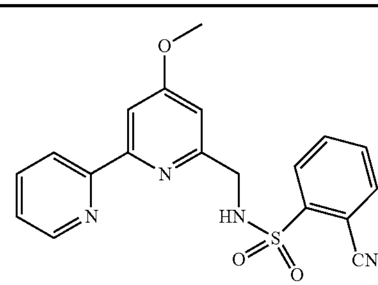 | 61 | 381 |

-continued

| | | Structure | Yield (%) | m/z [ES+] |
|---|---|---|---|---|
| Example 34 | Compound 41 | 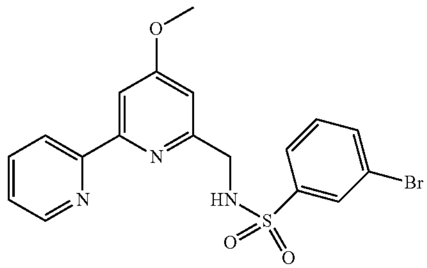 [SMILES: COc1cc(CNS(=O)(=O)c2cccc(Br)c2)nc(-c2ccccn2)c1] | 98 | 436 |
| Example 35 | Compound 42 | 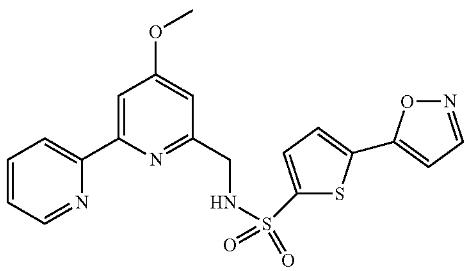 [SMILES: COc1cc(CNS(=O)(=O)c2ccc(-c3ccno3)s2)nc(-c2ccccn2)c1] | 70 | 429 |
| Example 36 | Compound 43 | 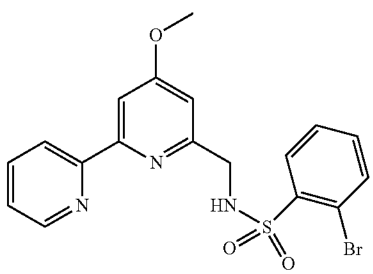 | 78 | 436 |
| Example 37 | Compound 44 | 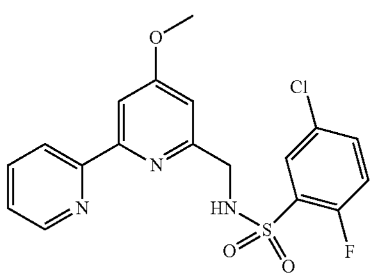 [SMILES: COc1cc(CNS(=O)(=O)c2cc(Cl)ccc2F)nc(-c2ccccn2)c1] | 71 | 408 |
| Example 38 | Compound 45 | 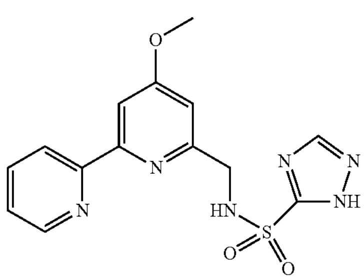 [SMILES: COc1cc(CNS(=O)(=O)c2ncn[nH]2)nc(-c2ccccn2)c1] | 70 | 347 |

-continued

| | | Structure | Yield (%) | m/z [ES+] |
|---|---|---|---|---|
| Example 39 | Compound 46 | 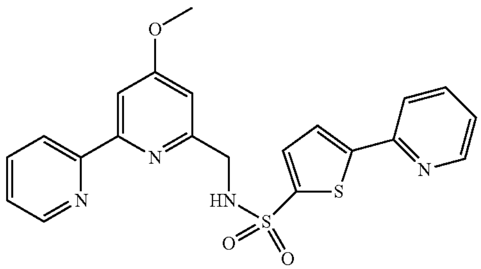 [SMILES: COc1cc(CNS(=O)(=O)c2ccc(-c3ccccn3)s2)nc(-c2ccccn2)c1] | 50 | 439 |
| Example 40 | Compound 47 | 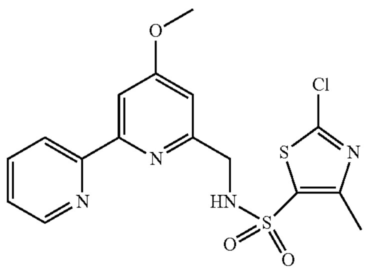 [SMILES: COc1cc(CNS(=O)(=O)c2sc(Cl)nc2C)nc(-c2ccccn2)c1] | 66 | 411 |
| Example 41 | Compound 48 | 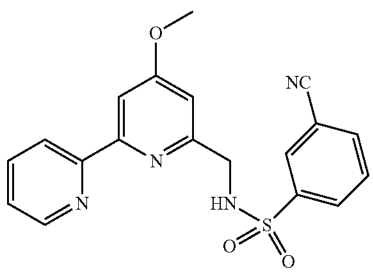 [SMILES: COc1cc(CNS(=O)(=O)c2cccc(C#N)c2)nc(-c2ccccn2)c1] | 86 | 381 |
| Example 42 | Compound 49 | 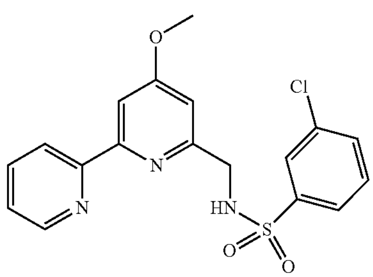 | 83 | 390 |
| Example 43 | Compound 50 | 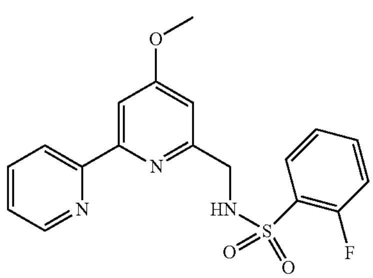 [SMILES: COc1cc(CNS(=O)(=O)c2ccccc2F)nc(-c2ccccn2)c1] | 81 | 374 |

-continued

| | | Structure | Yield (%) | m/z [ES+] |
|---|---|---|---|---|
| Example 44 | Compound 51 | 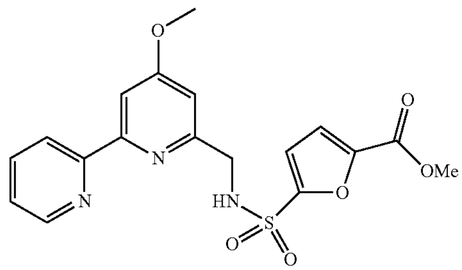 [SMILES: COC(=O)c1ccc(S(=O)(=O)NCc2cc(OC)cc(-c3ccccn3)n2)o1] | 67 | 404 |
| Example 45 | Compound 52 | 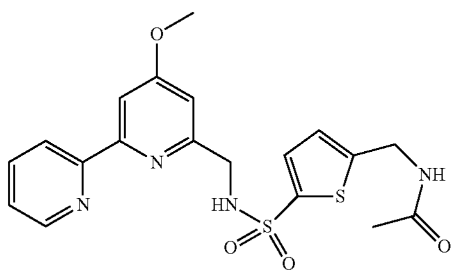 [SMILES: COc1cc(CNS(=O)(=O)c2ccc(CNC(C)=O)s2)nc(-c2ccccn2)c1] | 65 | 433 |
| Example 46 | Compound 53 | 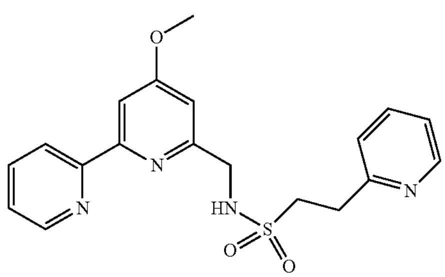 [SMILES: COc1cc(CNS(=O)(=O)CCc2ccccn2)nc(-c2ccccn2)c1] | 42 | 385 |
| Example 47 | Compound 54 | 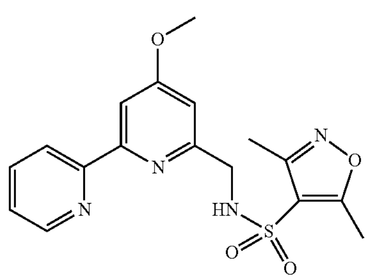 [SMILES: COc1cc(CNS(=O)(=O)c2c(C)noc2C)nc(-c2ccccn2)c1] | 81 | 375 |
| Example 48 | Compound 55 | 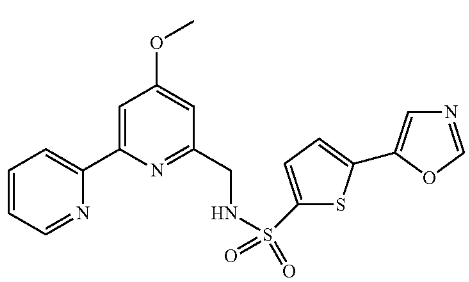 [SMILES: COc1cc(CNS(=O)(=O)c2ccc(-c3cnco3)s2)nc(-c2ccccn2)c1] | 98 | 429 |

-continued
| | | Structure | Yield (%) | m/z [ES+] |
|---|---|---|---|---|
| Example 49 | Compound 56 | 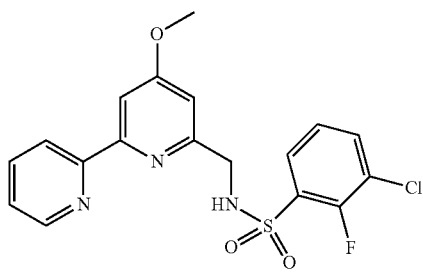 | 86 | 408 |
| Example 50 | Compound 57 | 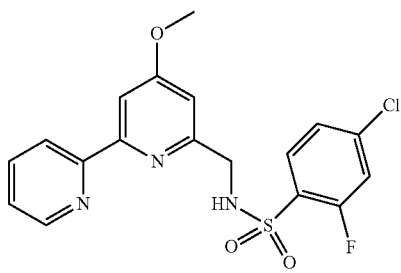 [SMILES: COc1cc(CNS(=O)(=O)c2ccc(Cl)cc2F)nc(-c2ccccn2)c1] | 62 | 408 |
| Example 51 | Compound 58 | 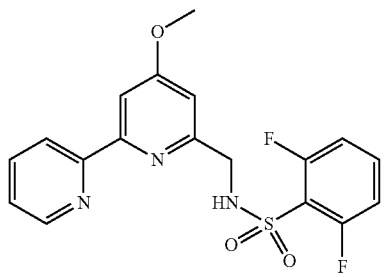 [SMILES: COc1cc(CNS(=O)(=O)c2c(F)cccc2F)nc(-c2ccccn2)c1] | 92 | 392 |
| Example 52 | Compound 59 | 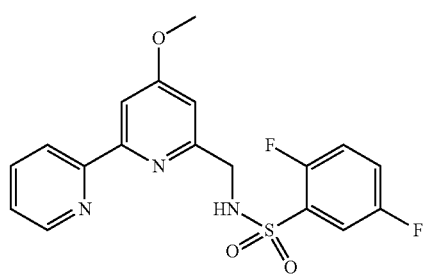 [SMILES: COc1cc(CNS(=O)(=O)c2cc(F)ccc2F)nc(-c2ccccn2)c1] | 81 | 392 |
| Example 53 | Compound 60 | 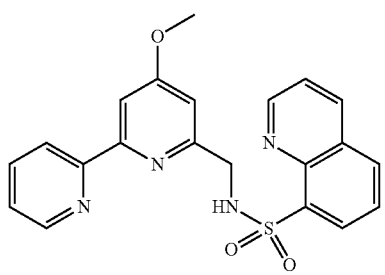 [SMILES: COc1cc(CNS(=O)(=O)c2cccc3cccnc23)nc(-c2ccccn2)c1] | 93 | 407 |

-continued

| | | Structure | Yield (%) | m/z [ES+] |
|---|---|---|---|---|
| Example 54 | Compound 61 | 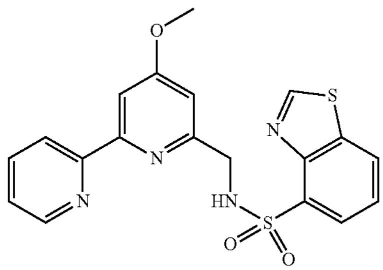 [SMILES: COc1cc(CNS(=O)(=O)c2cccc3scnc23)nc(-c2ccccn2)c1] | 100 | 413 |
| Example 55 | Compound 62 | 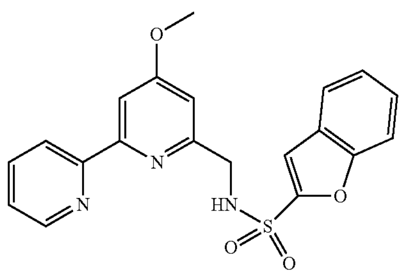 [SMILES: COc1cc(CNS(=O)(=O)c2cc3ccccc3o2)nc(-c2ccccn2)c1] | 99 | 396 |
| Example 56 | Compound 63 | 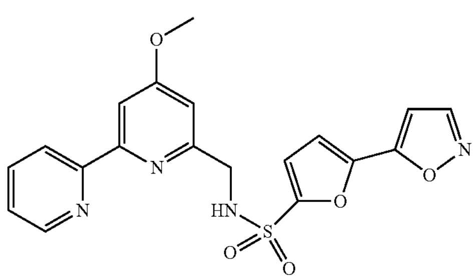 [SMILES: COc1cc(CNS(=O)(=O)c2ccc(-c3ccno3)o2)nc(-c2ccccn2)c1] | 49 | 413 |
| Example 57 | Compound 64 | 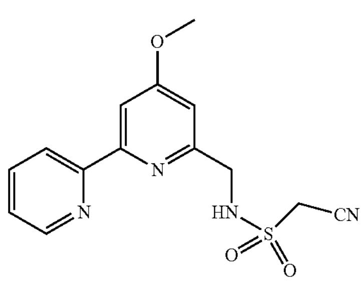 [SMILES: COc1cc(CNS(=O)(=O)CC#N)nc(-c2ccccn2)c1] | 66 | 319 |
| Example 58 | Compound 65 | 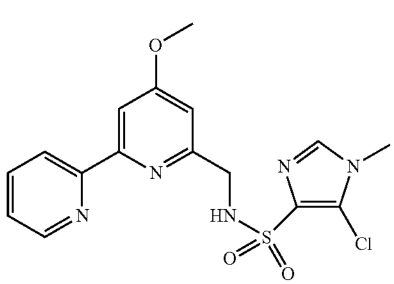 [SMILES: COc1cc(CNS(=O)(=O)c2ncn(C)c2Cl)nc(-c2ccccn2)c1] | 73 | 394 |

-continued

|  |  | Structure | Yield (%) | m/z [ES+] |
|---|---|---|---|---|
| Example 59 | Compound 66 | 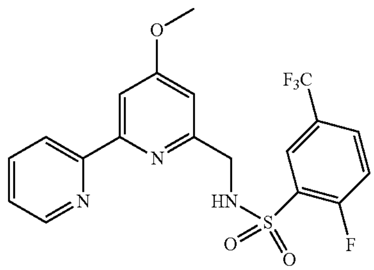 | 77 | 442 |
| Example 60 | Compound 67 | 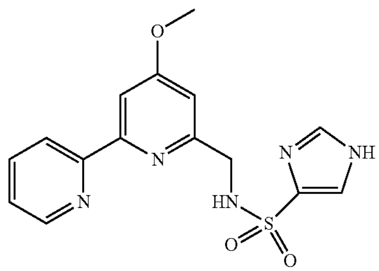 [SMILES: COc1cc(CNS(=O)(=O)c2c[nH]cn2)nc(-c2ccccn2)c1] | 60 | 346 |
| Example 61 | Compound 68 | 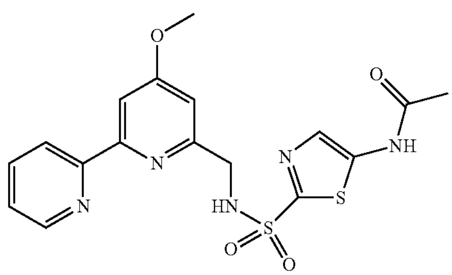 [SMILES: COc1cc(CNS(=O)(=O)c2ncc(NC(C)=O)s2)nc(-c2ccccn2)c1] | 42 | 420 |
| Example 62 | Compound 69 | 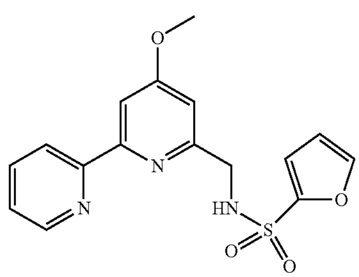 [SMILES: COc1cc(CNS(=O)(=O)c2ccco2)nc(-c2ccccn2)c1] | 88 | 346 |
| Example 63 | Compound 70 | 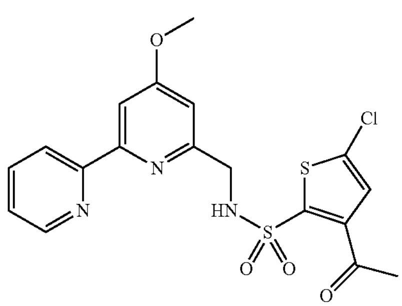 [SMILES: COc1cc(CNS(=O)(=O)c2sc(Cl)cc2C(C)=O)nc(-c2ccccn2)c1] | 36 | 438 |

-continued

| | Structure | Yield (%) | m/z [ES+] |
|---|---|---|---|
| Example 64 Compound 71 | | 64 | 350 |
| Example 65 Compound 72 | | 78 | 434 |
| Example 66 Compound 73 | | 93 | 412 |
| Example 67 Compound 74 | | 59 | 401 |
| Example 68 Compound 75 | | 89 | 398 |

-continued

|  | Structure | Yield (%) | m/z [ES+] |
|---|---|---|---|
| Example 69 Compound 76 | | 59 | 375 |
| Example 70 Compound 77 | | 72 | 392 |
| Example 71 Compound 78 | | 36 | 346 |
| Example 72 Compound 79 | | 33 | 427 |
| Example 73 Compound 80 | | 24 | 400 |

-continued

| | Structure | Yield (%) | m/z [ES+] |
|---|---|---|---|
| Example 74 Compound 81 | | 91 | 322 |
| Example 75 Compound 82 | | 77 | 362 |
| Example 76 Compound 83 | | 44 | 322 |
| Example 77 Compound 84 | | 92 | 404 |
| Example 78 Compound 85 | | 65 | 422 |

-continued

| | Structure | Yield (%) | m/z [ES+] |
|---|---|---|---|
| Example 79 Compound 86 | | 69 | 376 |
| Example 80 Compound 87 | | 97 | 414 |
| Example 81 Compound 88 | | 98 | 412 |
| Example 82 Compound 89 | | 78 | 432 |
| Example 83 Compound 90 | | 83 | 444 |

-continued

| | | Structure | Yield (%) | m/z [ES+] |
|---|---|---|---|---|
| Example 84 | Compound 91 | 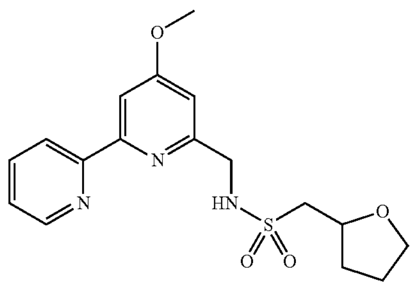 [SMILES: COc1cc(CNS(=O)(=O)CC2CCCO2)nc(-c2ccccn2)c1] | 77 | 364 |
| Example 85 | Compound 92 | 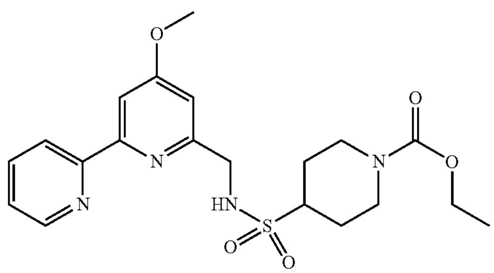 [SMILES: CCOC(=O)N1CCC(S(=O)(=O)NCc2cc(OC)cc(-c3ccccn3)n2)CC1] | 82 | 435 |
| Example 86 | Compound 93 | 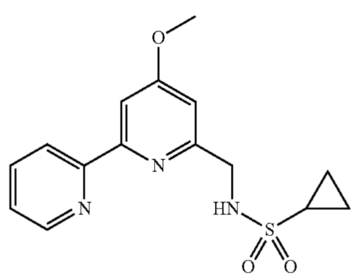 [SMILES: COc1cc(CNS(=O)(=O)C2CC2)nc(-c2ccccn2)c1] | 84 | 320 |
| Example 87 | Compound 94 | 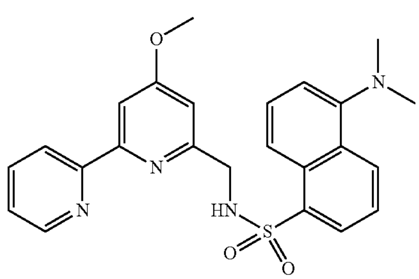 [SMILES: COc1cc(CNS(=O)(=O)c2cccc3c(N(C)C)cccc23)nc(-c2ccccn2)c1] | 76 | 449 |
| Example 88 | Compound 95 | 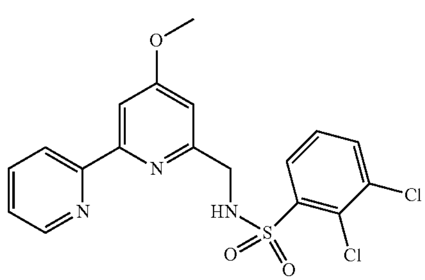 | 70 | 425 |

-continued

| | Structure | Yield (%) | m/z [ES+] |
|---|---|---|---|
| Example 89 Compound 96 | | 65 | 360 |
| Example 90 Compound 97 | | 75 | 425 |
| Example 91 Compound 98 | | 77 | 386 |
| Example 92 Compound 99 | | 87 | 370 |
| Example 93 Compound 100 | | 72 | 425 |

-continued

| | | Structure | Yield (%) | m/z [ES+] |
|---|---|---|---|---|
| Example 94 | Compound 101 | 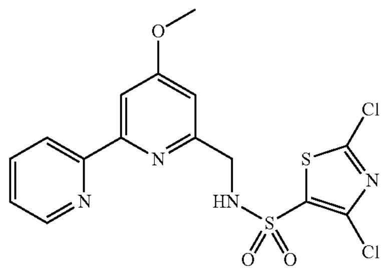 [SMILES: COc1cc(CNS(=O)(=O)c2sc(Cl)nc2Cl)nc(-c2ccccn2)c1] | 40 | 432 |
| Example 95 | Compound 102 | 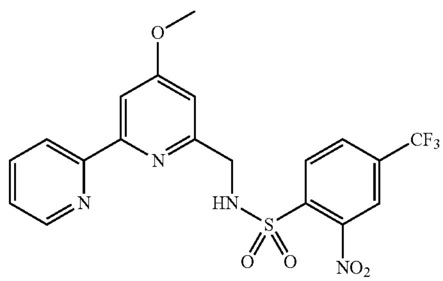 [SMILES: COc1cc(CNS(=O)(=O)c2ccc(C(F)(F)F)cc2[N+](=O)[O-])nc(-c2ccccn2)c1] | 74 | 469 |
| Example 96 | Compound 103 | 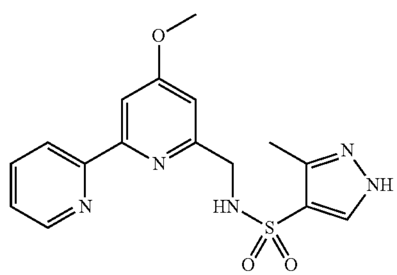 [SMILES: COc1cc(CNS(=O)(=O)c2c[nH]nc2C)nc(-c2ccccn2)c1] | 53 | 360 |
| Example 97 | Compound 104 | 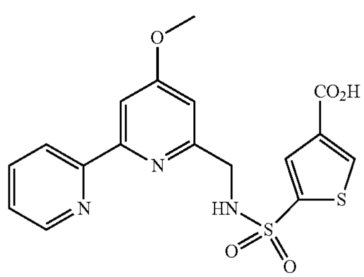 [SMILES: COc1cc(CNS(=O)(=O)c2cc(C(=O)O)cs2)nc(-c2ccccn2)c1] | 22 | 406 |
| Example 98 | Compound 105 | 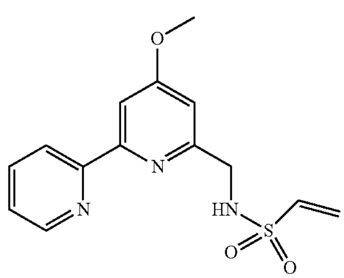 [SMILES: C=CS(=O)(=O)NCc1cc(OC)cc(-c2ccccn2)n1] | 52 | 306 |

-continued

| | | Structure | Yield (%) | m/z [ES+] |
|---|---|---|---|---|
| Example 99 | Compound 106 | 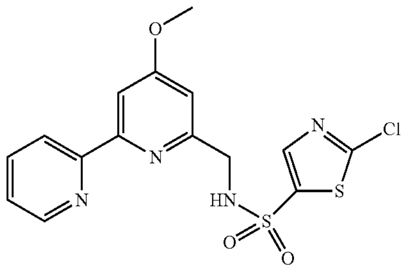 [SMILES: COc1cc(CNS(=O)(=O)c2cnc(Cl)s2)nc(-c2ccccn2)c1] | 32 | 397 |
| Example 100 | Compound 107 | 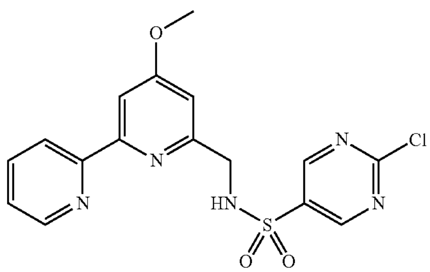 [SMILES: COc1cc(CNS(=O)(=O)c2cnc(Cl)nc2)nc(-c2ccccn2)c1] | 10 | 392 |
| Example 101 | Compound 108 | 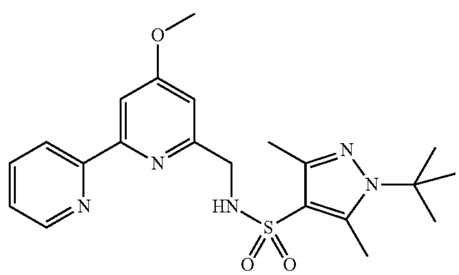 [SMILES: COc1cc(CNS(=O)(=O)c2c(C)nn(C(C)(C)C)c2C)nc(-c2ccccn2)c1] | 57 | 430 |

Example 102

Synthesis of Compound 109

Thiophene-2-sulfonic acid (4-methanesulfonyl-[2,2']bipyridinyl-6-ylmethyl)-amide

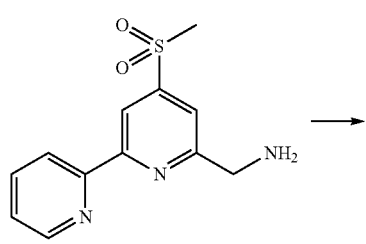

→

-continued

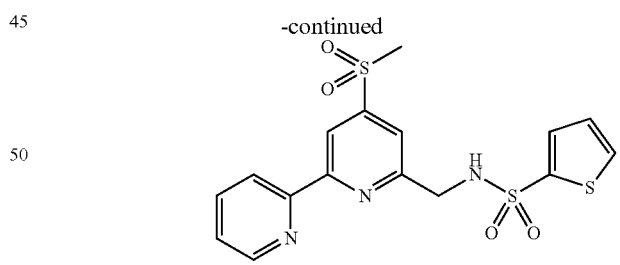

The title compound was prepared following the procedure described for the synthesis of Compound 33 (Example 26), but using thiophene-2-sulfonyl chloride in the last step. Thiophene-2-sulfonic acid (4-methanesulfonyl-[2,2']bipyridinyl-6-ylmethyl)-amide was obtained as a colorless oil (85 mg, 81%).

m/z: [ES+] 410 [M+1]

1H NMR: (400 MHz, CDCl$_3$) 3.11 (3H, s, CH$_3$), 4.53 (2H, d, CH$_2$), 6.31 (1H, t, NH), 6.96 (1H, dd, ArH), 7.36 (1H, ddd, ArH), 7.48 (1H, dd, ArH), 7.59 (1H, dd, ArH), 7.70 (1H, d, ArH), 7.82 (1H, dt, ArH), 8.32 (1H, td, ArH), 8.66 (1H, ddd, ArH), 8.71 (1H, d, ArH)

Example 103

Synthesis of Compound 110

5-Methyl-thiophene-2-sulfonic acid (4-methane-sulfonyl-[2,2']pyridinyl-6-ylmethyl)-amide

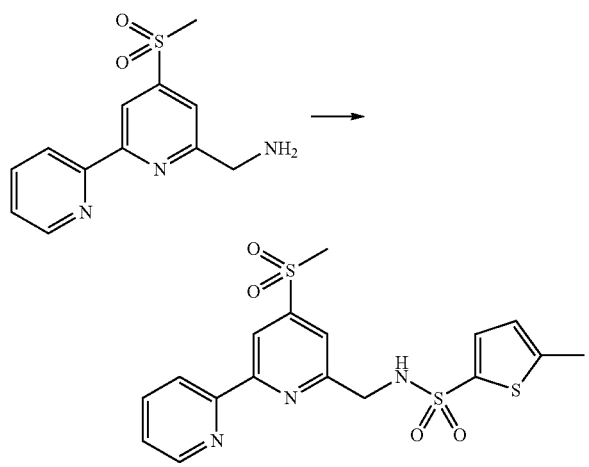

The title compound was prepared following the procedure described for the synthesis of Compound 33 (Example 26), but using 5-methyl-thiophene-2-sulfonyl chloride in the last step. 5-Methyl-thiophene-2-sulfonic acid (4-methanesulfonyl-[2,2']bipyridinyl-6-ylmethyl)-amide was obtained as a white solid (79 mg, 77%).

m/z: [ES+] 424 [M+1]

1H NMR: (400 MHz, CDCl$_3$) 2.37 (3H, s, CH$_3$), 3.11 (3H, s, CH$_3$), 4.51 (2H, d, CH$_2$), 6.26 (1H, t, NH), 7.35 (1H, d, ArH), 7.37 (1H, dd, ArH), 7.69 (1H, d, ArH), 7.82 (1H, dt, ArH), 8.33 (1H, d, ArH), 8.66 (1H, ddd, ArH), 8.71 (1H, d, ArH)

Example 104

Synthesis of Compound 111

3-Chloro-2-fluoro-N-(4-methanesulfonyl-[2,2']pyridinyl-6-ylmethyl)-benzenesulfonamide

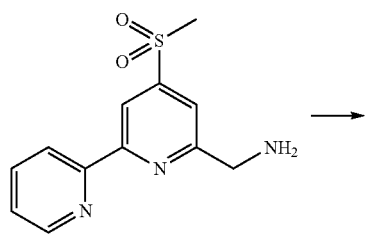

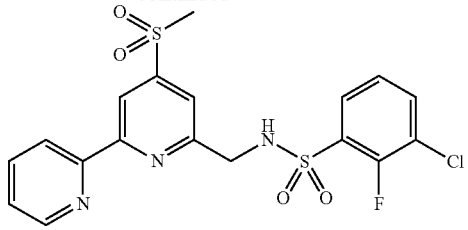

The title compound was prepared following the procedure described for the synthesis of Compound 33 (Example 26), but using 3-chloro-2-fluoro-benzenesulfonyl chloride in the last step. 3-Chloro-2-fluoro-N-(4-methanesulfonyl-[2,2']bipyridinyl-6-ylmethyl)-benzenesulfonamide was obtained as a white solid (98 mg, 88%).

m/z: [ES+] 456 [M+1]

1H NMR: (400 MHz, CDCl$_3$) 3.10 (3H, s, CH$_3$), 4.54 (2H, d, CH$_2$), 6.46 (1H, t, NH), 7.10 (1H, dt, ArH), 7.37 (1H, ddd, ArH), 7.45 (1H, ddd, ArH), 7.63 (1H, d, ArH), 7.72 (1H, ddd, ArH), 7.83 (1H, dt, ArH), 8.30 (1H, d, ArH), 8.67 (1H, ddd, ArH), 8.69 (1H, d, ArH)

Example 105

Synthesis of Further Compounds of Formula (I)

Analogous procedures as those described in Examples 1, 22/23 and 26 may be used to obtain the corresponding further compounds by reacting the respective amine with one of the following reagents in the last step:

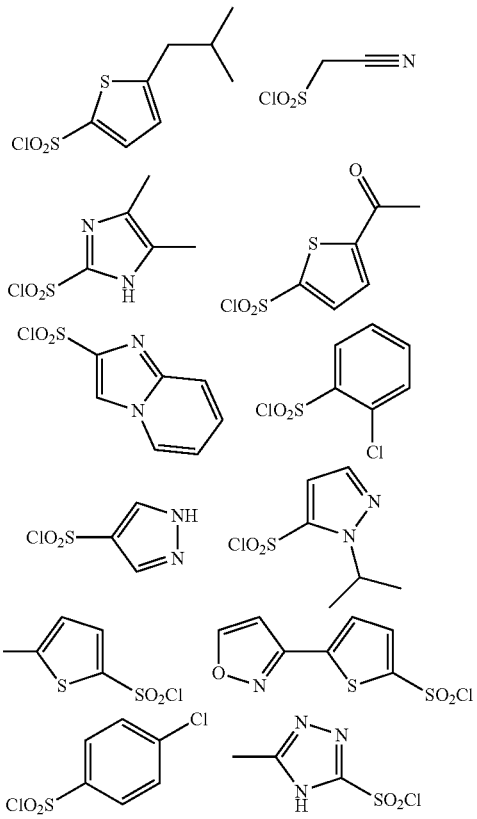

109
-continued
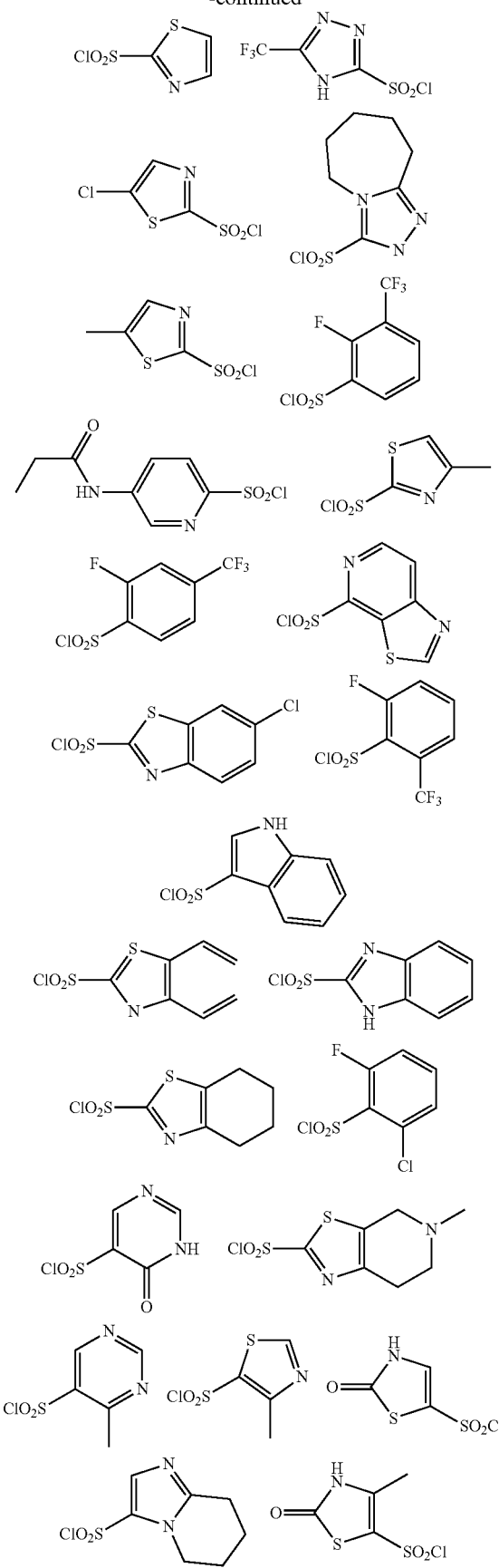
110
-continued
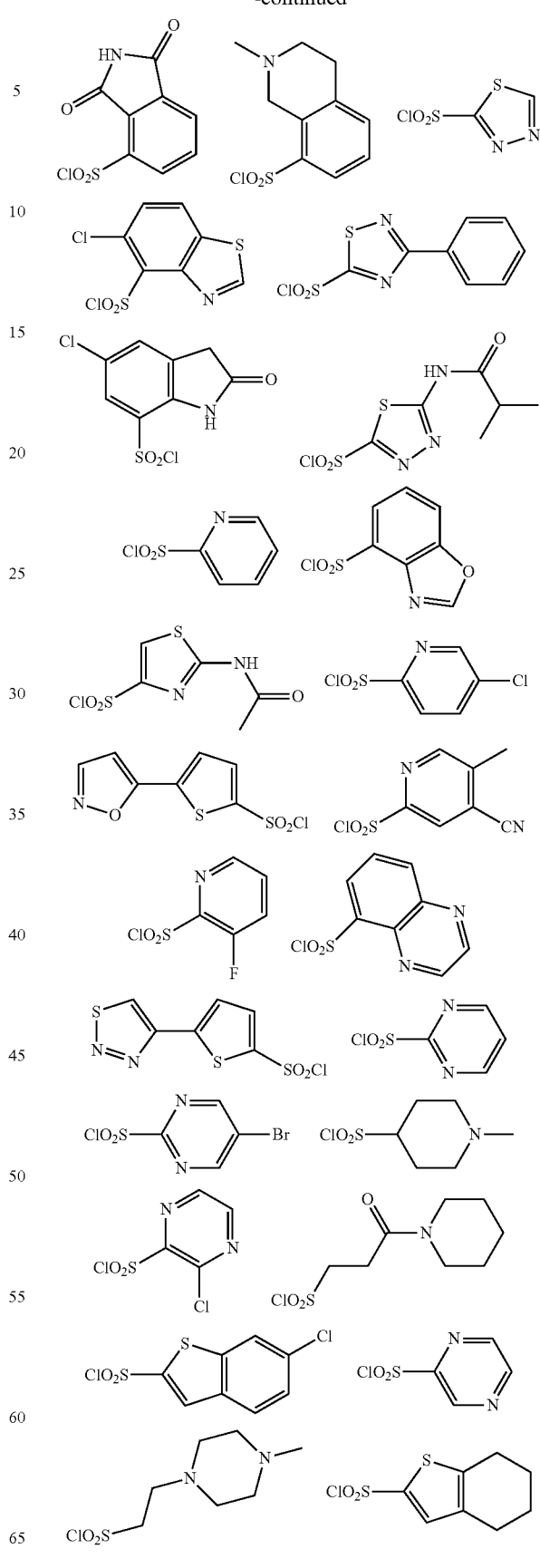

-continued

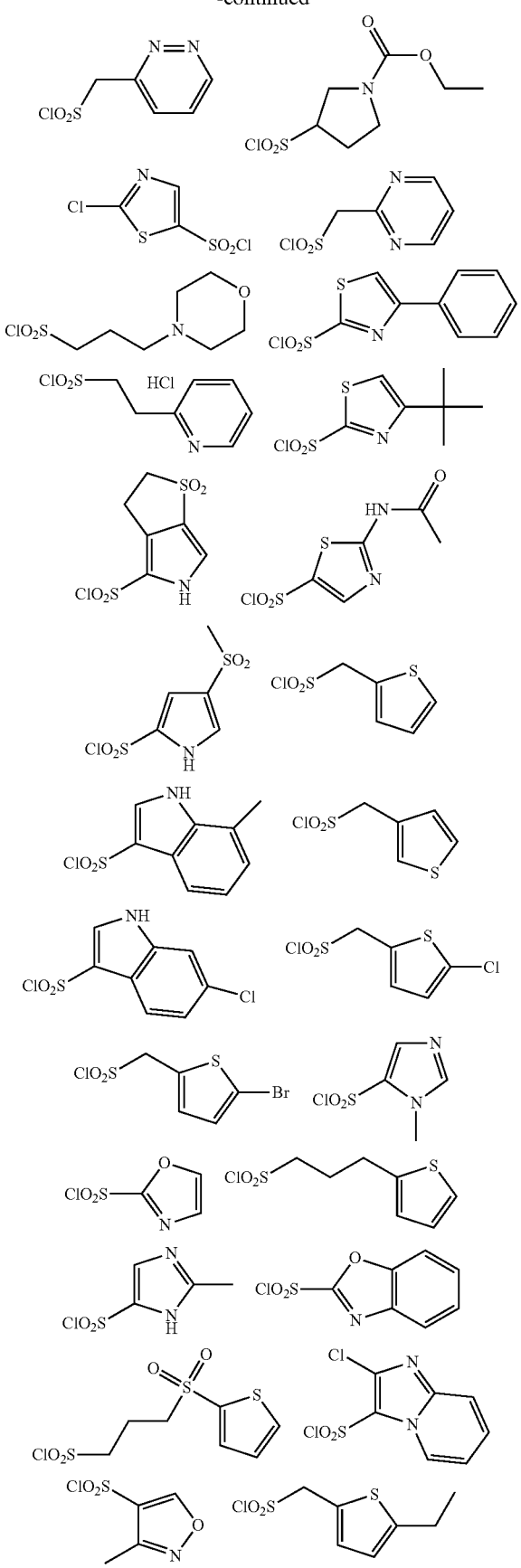

-continued

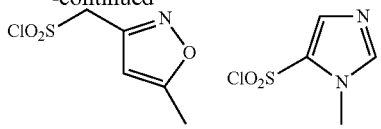

Biological Activity

Example 106

Protection Against Hydrogen Peroxide-Induced Cell Death

The aim of this assay is to determine the neuroprotective effect of the compounds when human neuroblastoma cells are exposed to the oxidative stress induced by hydrogen peroxide, which leads to cell death. Therefore the protective effect of the compounds was measured by monitoring cell survival using a suitable commercial kit (Cytotoxicity Detection Kit, Roche Diagnostics GmbH, Mannheim, Germany) based on the quantification of the lactate dehydrogenase activity obtained from lysates of the remaining live cells with a colorimetric assay yielding absorbance at 492 nm as the final readout.

SH-SY5Y human neuroblastoma cells were seeded into 96-well culture plate at a density of 10,000 cells/well. Cells were preincubated for one hour with different concentrations of the compound at a 1% (v/v) DMSO concentration in an equivolumetric mixture of Minimum Essential Medium (MEM) and Nutrient Mixture HAM F12 supplemented with 10% foetal bovine serum, 100 U/ml penicillin, 100 µg/ml streptomycin, 1 mM each of non-essential aminoacids (commercial preparation from GIBCO, Paisley, UK) and 2 mM L-glutamine. Hydrogen peroxide was then added to reach 100 µM and the incubation was extended for 24 h. Then the medium was removed and live cells, which remained attached to the bottom of the plate, were lysed by incubating them during 5 min with 50 µl of 1% (v/v) Triton X-100 in Krebs-Hepes buffer (10 mM Hepes pH7.3 with 145 mM NaCl, 5.5 mM KCl, 1 mM $MgCl_2$, 2 mM $CaCl_2$ and 1 mM glucose). This lysate was used to measure LDH activity using the commercial kit according to the manufacturer's instructions. In the culture plate several wells were included as a control of cell death, in these wells the cells were preincubated with 1% (v/v) DMSO before hydrogen peroxide addition. Likewise, several wells were included as control for full cell survival, in these wells the addition of $H_2O_2$ was omitted. The absorbance of each tested sample was normalized to that of the control wells, so that for every compound concentration the percentage of protective effect was calculated with the following equation:

$$\% \text{ Effect} = 100 \cdot \frac{E-S}{E-B}$$

where "S" is the absorbance of the sample being considered, "E" is the average absorbance of wells used as control of full cell survival and "B" is the average absorbance of wells used as control of cell death. The values obtained at every compound concentration were finally used to calculate the EC50 (i.e., the concentration causing 50% of protective effect) of the tested compound. For that purpose the data were fitted to a classical 4-parameters isotherm equation using the nonlinear regression function of GraphPad™ Prism 5.0 (GraphPad Software Inc.), such equation is described below:

$$\% \text{ Inhibition} = L + \frac{H - L}{1 + \left(\frac{EC50}{C}\right)^n}$$

where "L" is the lower asymptote of the theoretical sigmoidal curve, "H" is the higher asymptote, "C" is the concentration of compound and "n" is the Hill coefficient.

In Table 2 as follows, the average EC50 values (in μM) of the tested compounds are shown.

TABLE 2

| Compound No. | Average EC50 (μM) |
|---|---|
| Compound 1 | 36.0 |
| Compound 2 | 0.80 |
| Compound 3 | 23.0 |
| Compound 4 | 2.60 |
| Compound 5 | 39.8 |
| Compound 6 | 1.58 |
| Compound 7 | 11.2 |
| Compound 8 | 0.09 |
| Compound 9 | 6.10 |
| Compound 10 | 1.17 |
| Compound 11 | 1.30 |
| Compound 12 | 1.06 |
| Compound 13 | 1.50 |
| Compound 14 | 1.60 |
| Compound 15 | 4.80 |
| Compound 16 | 3.20 |
| Compound 17 | 0.82 |
| Compound 18 | 1.88 |
| Compound 19 | 1.30 |
| Compound 20 | 5.10 |
| Compound 21 | 5.19 |
| Compound 22 | 0.88 |
| Compound 23 | 2.91 |
| Compound 24 | 3.46 |
| Compound 25 | 4.95 |
| Compound 26 | 4.60 |
| Compound 27 | 3.52 |
| Compound 28 | 1.16 |
| Compound 30 | 0.29 |
| Compound 32 | 0.55 |
| Compound 33 | 1.02 |
| Compound 54 | 23.10 |
| Compound 55 | 1.30 |
| Compound 56 | 1.06 |
| Compound 57 | 1.50 |
| Compound 58 | 1.60 |
| Compound 59 | 4.80 |
| Compound 60 | 3.20 |
| Compound 61 | 0.82 |
| Compound 62 | 1.88 |
| Compound 79 | 0.72 |
| Compound 82 | 0.50 |
| Compound 95 | 1.09 |
| Compound 100 | 1.04 |
| Compound 101 | 0.23 |
| Compound 106 | 0.63 |

As may be observed, Compound 8 was the most active compound of those assayed.

Example 107

Inhibition of β-Amyloid Secretion

The inhibition caused by the compounds on the secretion of amyloid peptide β1-40 (Aβ1-40) was determined by measuring the levels of this peptide in cell supernatants after incubating the cells with several concentrations of the tested compound. A CHO7w cell line, stably transfected with human amyloid precursor protein (APP), was used. Cells were dispensed in 96-well culture plates (5,000 cells/well) and grown in DMEM supplemented with 2% (v/v) foetal bovine serum, 100 U/ml penicillin, 100 μg/ml streptomycin, 2 mM L-glutamine and 200 μg/ml G418 in the presence of several concentrations of the tested compound which had been previously dissolved in DMSO (1% (v/v) DMSO final concentration). After a 24 h incubation the amount of Aβ1-40 secreted to the medium was measured with an ELISA-based commercial kit (Human Amyloid β-40 ELISA High Sensitivity Kit, Millipore, Billerica, Mass., USA) using absorbance at 450 nm as the final readout. In the culture plate several wells were included as a control for lack of Aβ1-40 secretion, in these wells the cells were incubated in the presence of 16% (v/v) DMSO to inhibit cell growth therefore abolishing Aβ1-40 secretion. Likewise, several wells were also included as a control for full Aβ1-40 secretion, in these wells the cells were grown in the presence of 1% (v/v) DMSO. The absorbance of each tested sample was normalized to that of the control wells, so that for every compound concentration the percentage of inhibition was calculated with the following equation:

$$\% \text{ Inhibition} = 100 \cdot \frac{E - S}{E - B}$$

where "S" is the absorbance of the sample being considered, "E" is the average absorbance of wells lacking Aβ1-40 secretion and "B" is the average absorbance of wells with full Aβ1-40 secretion. The inhibition values obtained at every compound concentration were fitted to a 4-parameters isotherm equation, as described above, to calculate the 1050 (i.e., the concentration causing 50% of inhibition of Ab1-40 secretion).

Compounds 2, 4, 10, 19, 24, 26, 27, 29, 30, 33, 38, 40, 42, 44, 46, 47, 51, 52, 55, 56, 66, 73, 74, 75, 82, 84, 85, 86, 87, 88, 89, 97, 100, 101, 102, 106 and 107, when tested in this assay, provided average IC50 values ranging between 0.3 and 42 μM. The compound with the lowest IC50 value was Compound 85.

Example 108

Stimulation of sAPPα Secretion

The effect of the compounds on the stimulation of the secretion of soluble amyloid precursor protein-α (sAPPα) was determined by measuring the levels of this protein in cell supernatants after incubating the cells with several concentrations of the tested compound. A CHO7w cell line, stably transfected with human APP, was used. Cells were dispensed in 96-well culture plates (5,000 cells/well) and grown in DMEM supplemented with 2% (v/v) foetal bovine serum, 100 U/ml penicillin, 100 μg/ml streptomycin, 2 mM L-glutamine and 200 μg/ml G418 in the presence of several concentrations of the tested compound which had been previously dissolved in DMSO (1% (v/v) DMSO final concentration). After 24 h of incubation 5 μl of the culture supernatants were withdrawn and their sAPPα concentration was measured with a commercial kit (AlphaLISA® Amyloid Precursor Protein-α Secreted Research kit, PerkinElmer, Waltham, Mass., USA) following manufacturer's instructions. In the culture plate several wells were included as a control for background sAPPα secretion, in these wells the cells were incubated with 1% (v/v) DMSO. The results obtained for each tested sample were normalized by using the following equation:

$$\% \text{ Secretion} = 100 \cdot \frac{S-B}{M-B}$$

where "S" is the sAPPα concentration of the sample being considered, "B" is the average sAPPα concentration of wells used for background secretion and "M" is the sAPPα concentration of wells yielding the highest value. These normalized values obtained at every compound concentration were finally used to calculate the EC50 of the tested compound fitting them to a 4-parameters isotherm equation as already described. The average EC50s ranges are reported in Table 4 together with the maximum observed effect (and the concentration at which this effect was reached), this latter value was calculated for each compound according to the following equation:

$$\% \text{ Maximum effect} = 100 \cdot \frac{M}{B}$$

with "M" and "B" as defined above.

Compounds 2, 6, 8, 9, 10, 11, 12, 13, 14, 16, 18, 19, 28, 30, 32 and 33 were tested in this assay; average EC50 values were obtained ranging between 0.5 and 11 μM, and maximum effects between 250% and 500% were observed. The maximum effect was obtained with Compound 2, and Compound 8 reached the maximum effect at the lowest concentration.

The invention claimed is:
1. A compound of Formula (I):

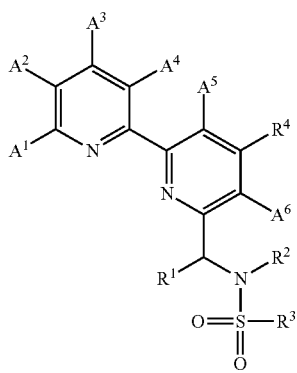

(I)

wherein
$R^1$ is selected from hydrogen, optionally substituted $C_1$-$C_6$ alkyl, halogen, nitro and amino;
$R^2$ is selected from hydrogen, optionally substituted heterocycloalkylalkyl, optionally substituted heteroarylalkyl, optionally substituted —($SO_2$)-thiophene and optionally substituted $C_1$-$C_6$ alkyl;
$R^3$ is selected from optionally substituted aryl, optionally substituted arylalkyl, optionally substituted heteroaryl, optionally substituted heterocycloalkyl, optionally substituted $C_1$-$C_6$ alkyl, optionally substituted cycloalkyl, optionally substituted heterocycloalkylalkyl, optionally substituted heteroarylalkyl, cyano, ethenyl and —N($R^7$)($R^8$), wherein $R^7$ and $R^8$ are independently selected from hydrogen or substituted or unsubstituted alkyl, and when $R^7$ and $R^8$ are substituted or unsubstituted alkyl, they may together form a heterocycloalkyl, containing five to seven members with the nitrogen atom and may intracyclically contain one or more further heteroatoms selected from nitrogen, oxygen and sulphur;
$R^4$ is selected from —O—$R^5$, wherein $R^5$ is optionally substituted $C_1$-$C_6$ alkyl, or —$SO_2$—$R^6$, wherein $R^6$ is $C_1$-$C_6$ alkyl;
$A^1$, $A^2$, $A^3$, $A^4$, $A^5$, $A^6$ are independently selected from hydrogen and $C_1$-$C_6$ alkyl; or a tautomer, salt, solvate or prodrug thereof.

2. A compound according to claim 1, wherein:
$R^1$ is hydrogen;
$R^2$ is selected from hydrogen, optionally substituted heteroarylalkyl and optionally substituted —($SO_2$)-thiophene;
$R^3$ is selected from optionally substituted aryl, optionally substituted arylalkyl, optionally substituted heteroaryl, optionally substituted heteroarylalkyl, optionally substituted heterocycloalkyl, optionally substituted heterocycloalkylalkyl, optionally substituted $C_1$-$C_6$ alkyl and optionally substituted cycloalkyl and ethenyl.

3. A compound according to claim 1, wherein $R^2$ is selected from hydrogen; pyridinemethyl optionally substituted with one or more substituents selected from alkoxyl, pyridine and O-alkylaminoalkyl; and —($SO_2$)-thiophene optionally substituted with halogen.

4. A compound according to claim 1, wherein $R^3$ is selected from optionally substituted phenyl, optionally substituted naphthyl, optionally substituted thiophene, optionally substituted benzothiophene, optionally substituted pyridine, optionally substituted 1,2,4-triazole, optionally substituted thiazole, optionally substituted furane, optionally substituted isoxazole, optionally substituted pyrazole, optionally substituted dihydro-benzo[1,4]dioxine, optionally substituted tetrahydrofurane-methyl, optionally substituted piperidine, optionally substituted pyridine-ethyl, optionally substituted quinoline, optionally substituted benzofurane, optionally substituted imidazole, optionally substituted 2,3-dihydrothiazole, optionally substituted pyrimidine, optionally substituted benzothiazole, optionally substituted cyclohexyl, optionally substituted cyclopropane, optionally substituted methyl, optionally substituted ethyl, optionally substituted propyl, optionally substituted isopropyl, optionally substituted tert-butyl, ethenyl, optionally substituted tetrahydrofurane, and optionally substituted N-morpholine.

5. A compound according to claim 1, wherein $R^2$ is selected from hydrogen; pyridinemethyl optionally substituted with one or more substituents selected from methoxyl, pyridine and —O—($CH_2$)$_2$—N—($CH_2$—$CH_3$)$_2$; and —($SO_2$)-thiophene optionally substituted with chloro.

6. A compound according to claim 1, wherein $R^3$ is selected from phenyl optionally substituted with one or more substituents selected from methoxy, methyl, methylcarbonyl, trifluoromethyl, fluor, chloro, cyano, bromo, methanesulfonyl, nitro, hydroxycarbonyl, tert-butyl and phenyl; naphthyl optionally substituted with dimethylamine; thiophene optionally substituted with one or more substituents selected from chloro, bromo, methyl, methylcarbonyl, oxazole, isoxazole, pyridine, —$CH_2$—NHCO—$CH_3$, hydroxycarbonyl; benzothiophene optionally substituted with one or more substituents selected from methyl, fluor, chloro; pyridine; 1,2,4-triazole; thiazole optionally substituted with one or more substituents selected from methyl, chloro, N-acetamide; furane optionally substituted with one or more substituents selected from methoxycarbonyl, isoxazole, methyl, methyl-isoxazole; isoxazole optionally substituted with one or more methyl; pyrazole optionally substituted with one or more substituents selected from methyl, tert-butyl; dihydro-benzo[1,4]dioxine; tetrahidrofurane-methyl; piperidine optionally substituted with ethoxycarbonyl; pyridine-ethyl; quinoline; benzofurane; imidazole optionally substituted with one or more substituents selected from chloro, methyl; 2,3-dihydrothiazole optionally substituted with one or more substituents selected from methyl, ketone; pyrimidine optionally substituted with chloro; benzothiazole; cyclohexyl; cyclopropane; methyl optionally substituted with one or more substituents selected from cyano and fluor; propyl optionally substituted with one or more substituents selected from fluor, chloro; isopropyl; tert-butyl; ethyl optionally substituted with one or more fluor atoms; ethenyl; tetrahydrofurane; and N-morpholine.

7. A compound according to claim 1, wherein in the compounds of Formula (I)
- $R^1$ is selected from hydrogen, optionally substituted $C_1$-$C_6$ alkyl, halogen, nitro and amino;
- $R^2$ is selected from hydrogen, optionally substituted heterocycloalkyl, optionally substituted heteroaryl, optionally substituted $C_1$-$C_6$ alkyl and optionally substituted —$SO_2$-thiophene;
- $R^3$ is selected from optionally substituted aryl, optionally substituted heteroaryl, optionally substituted heterocycloalkyl, optionally substituted $C_1$-$C_6$ alkyl, optionally substituted heterocycloalkylalkyl, optionally substituted heteroarylalkyl and cyano.

8. A compound according to claim 7, wherein $R^3$ is selected from the following:

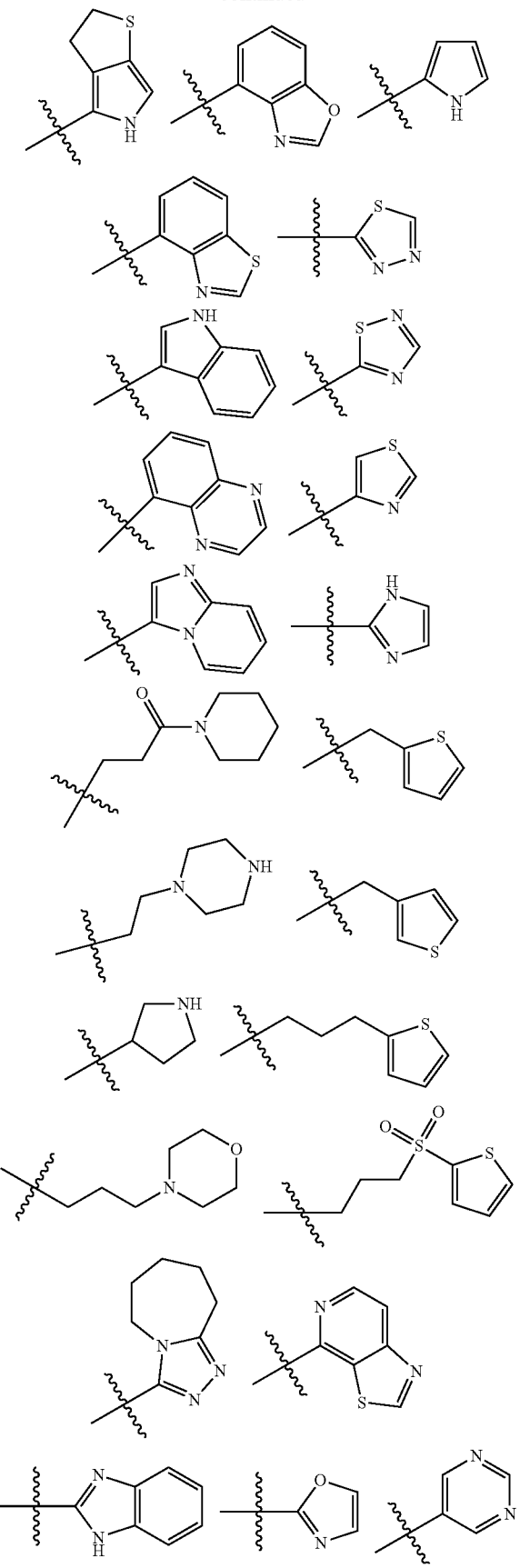

-continued

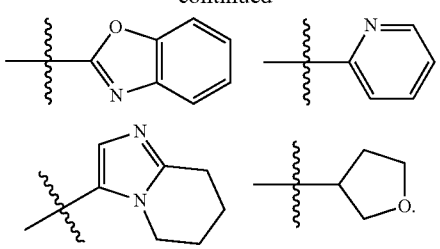

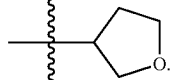

9. A compound according to claim 1, wherein $R^1$ is selected from hydrogen and methyl.

10. A compound according to claim 1, wherein $R^2$ is selected from hydrogen and optionally substituted —($SO_2$)-thiophene.

11. A compound according to claim 1, wherein $R^4$ is selected from —O—$CH_3$, —O—$(CH_2)_2$—N($CH_2$—$CH_3)_2$, and —$SO_2$—$CH_3$.

12. A compound according to claim 1, wherein $A^1, A^2, A^3, A^4, A^5, A^6$ are independently selected from hydrogen and methyl.

13. A compound according to claim 12, wherein $A^1, A^2, A^3, A^4, A^5, A^6$ are hydrogen.

14. A compound according to claim 1, selected from the following:

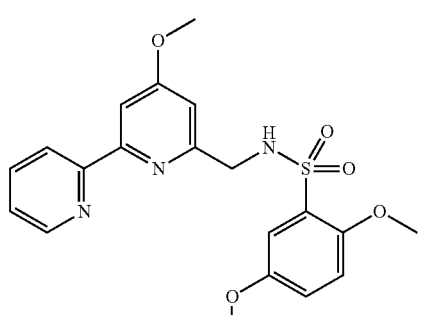

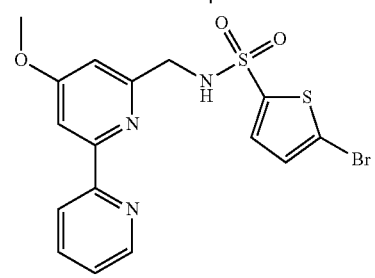

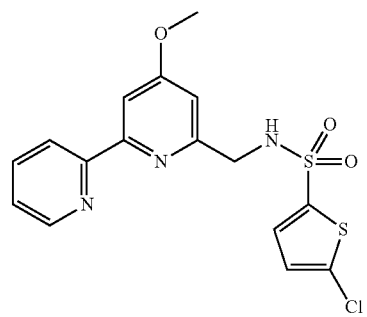

-continued

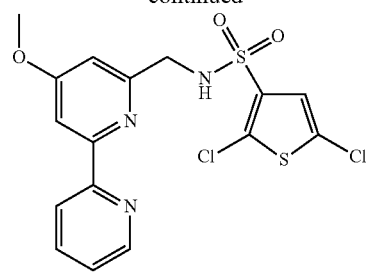

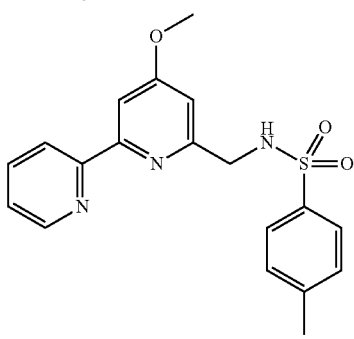

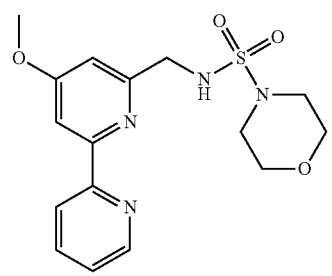

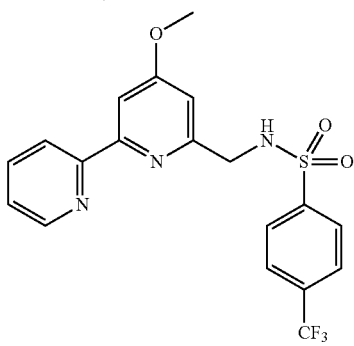

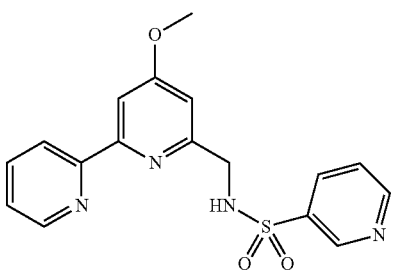

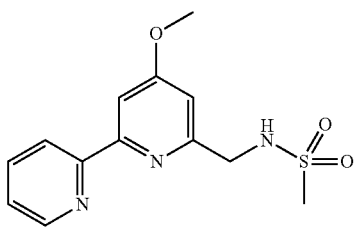

121
-continued
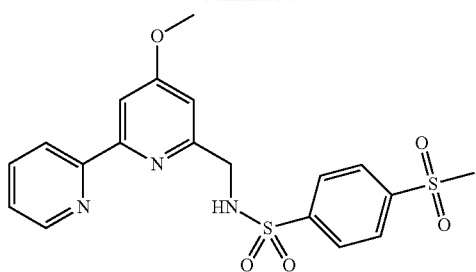
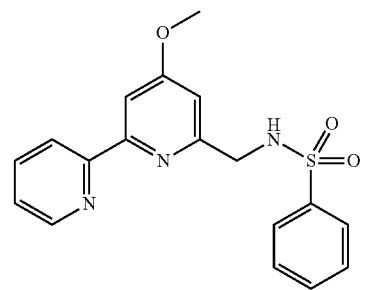
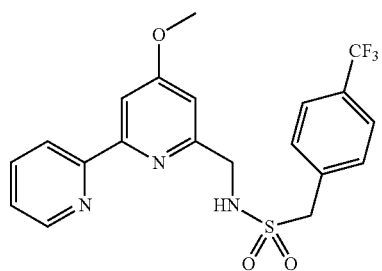
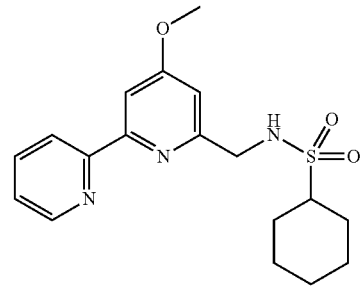
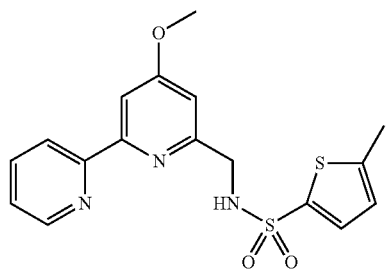
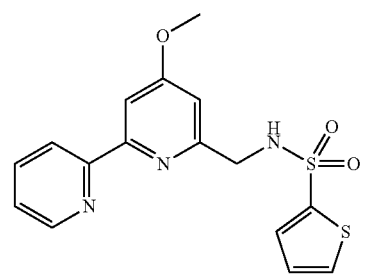
122
-continued
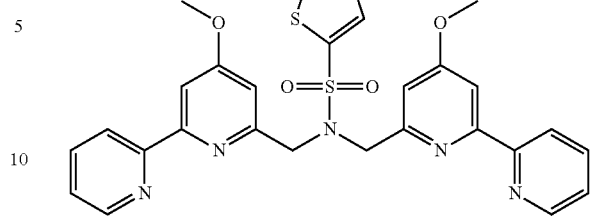
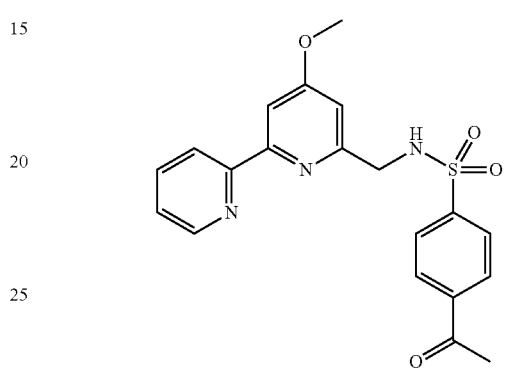
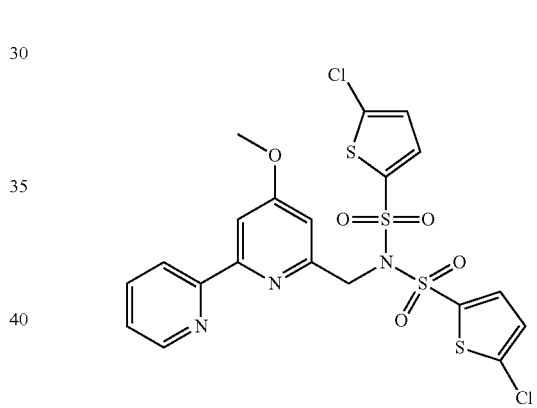
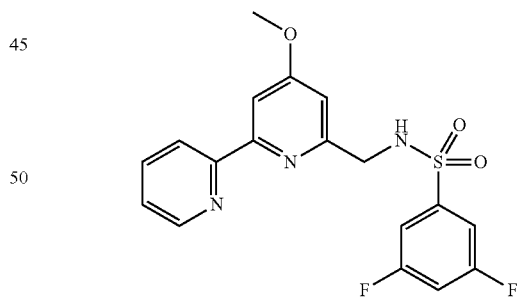
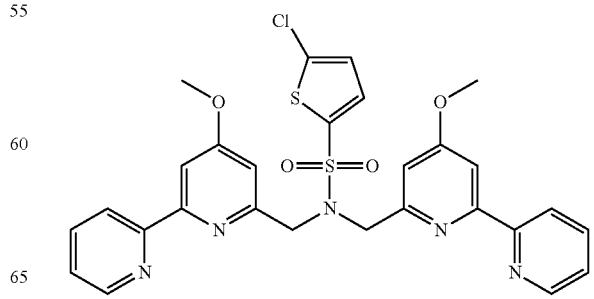

123
-continued
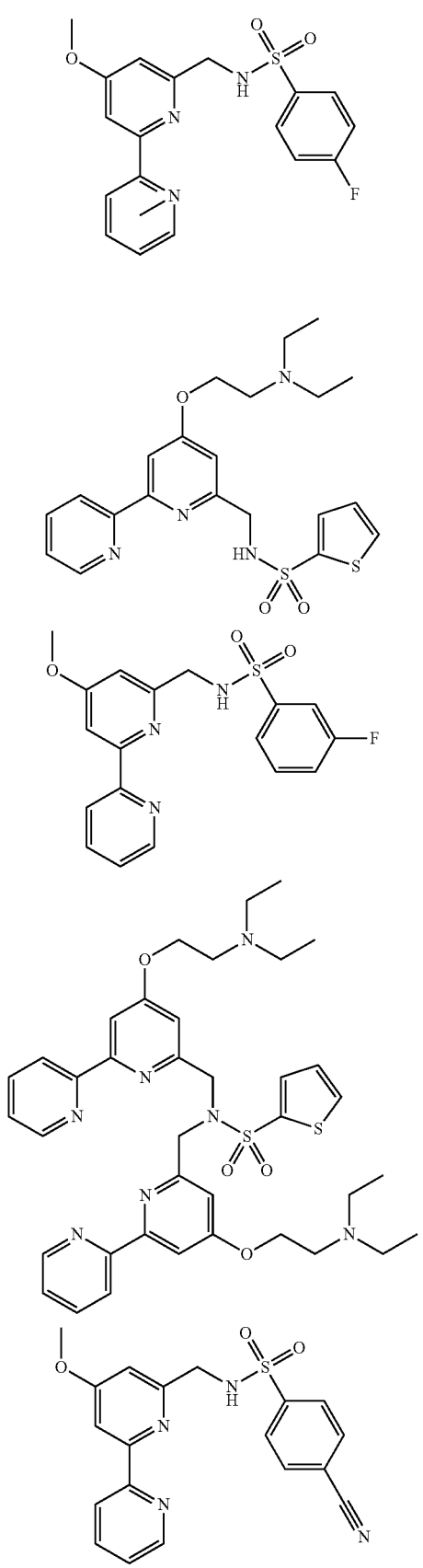
124
-continued
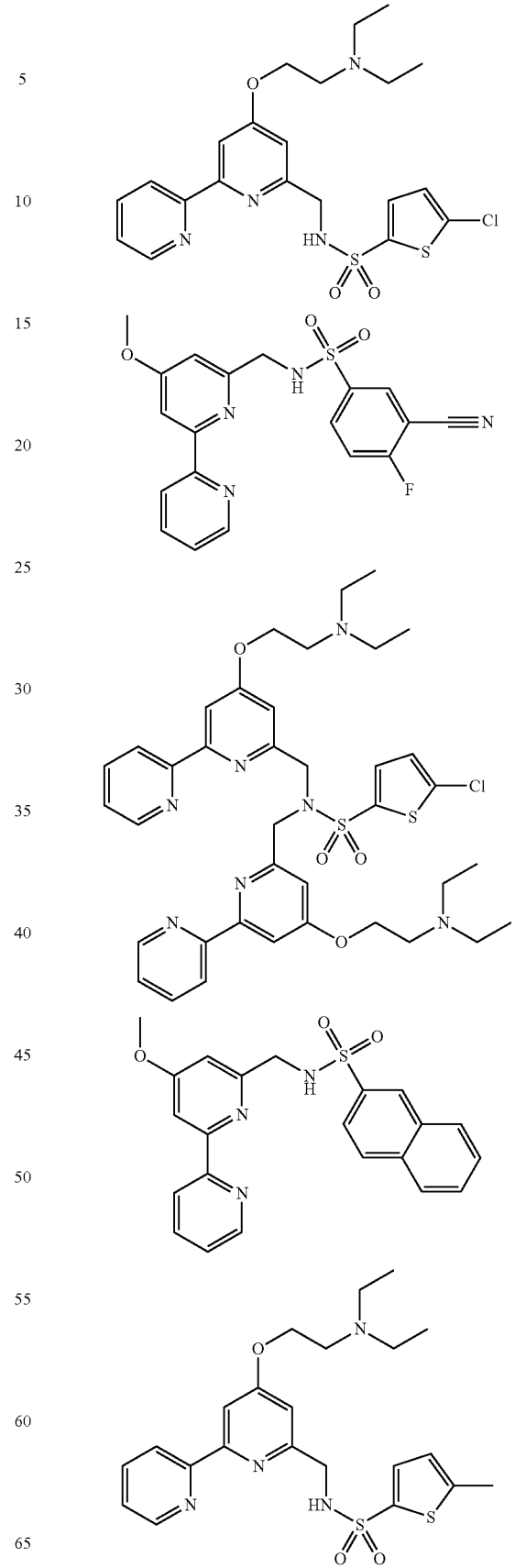

125
-continued
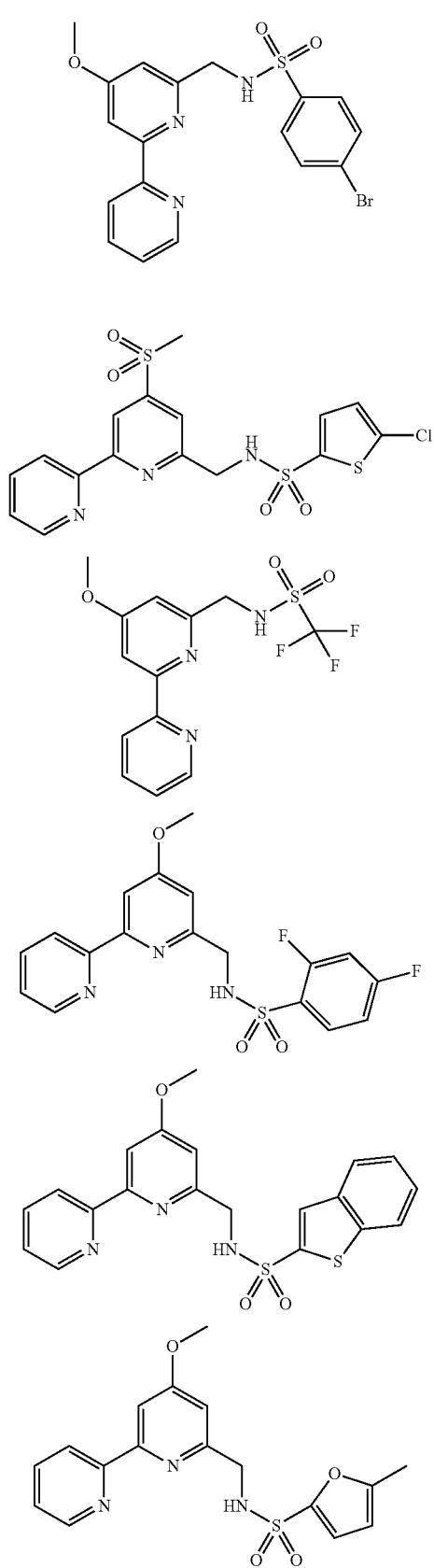
126
-continued
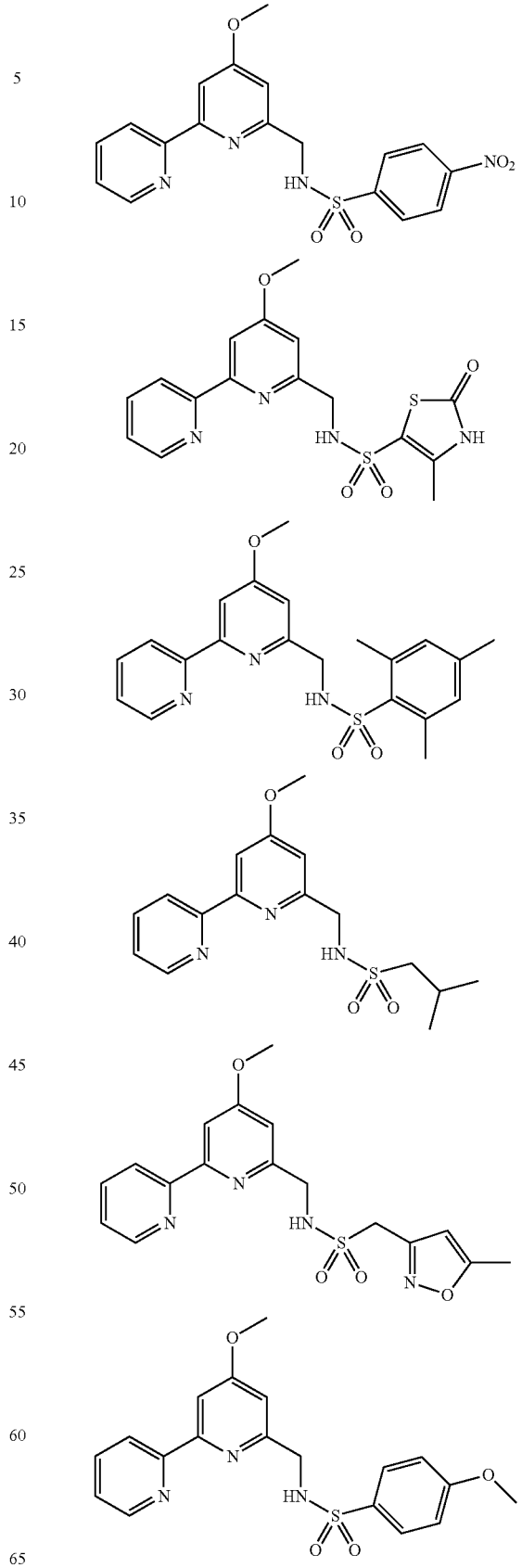

127
-continued
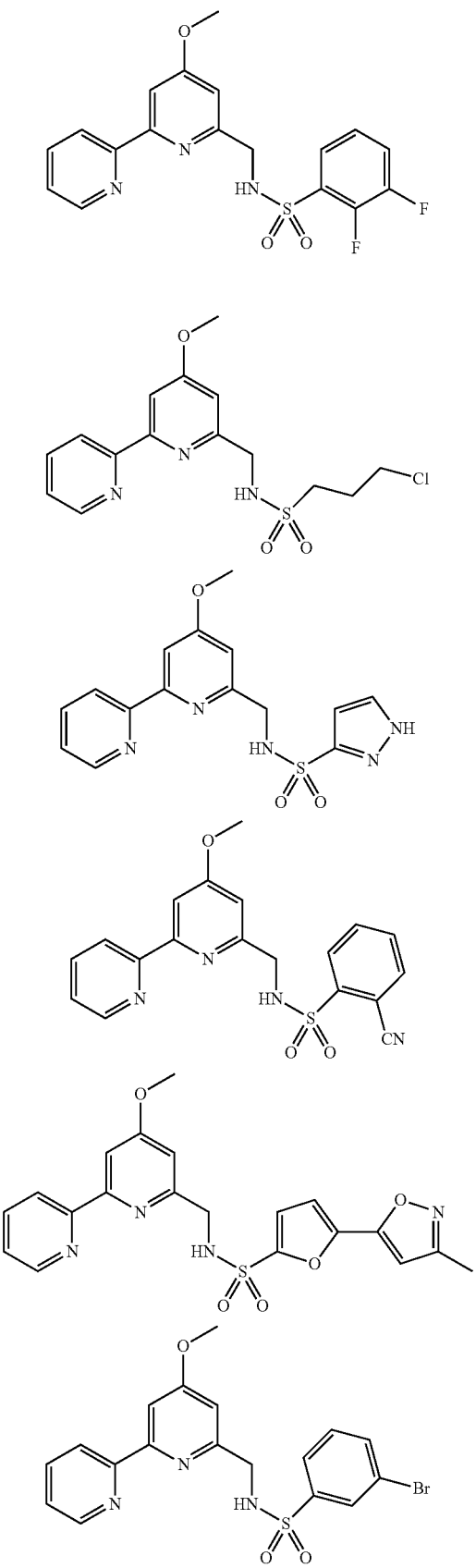
128
-continued
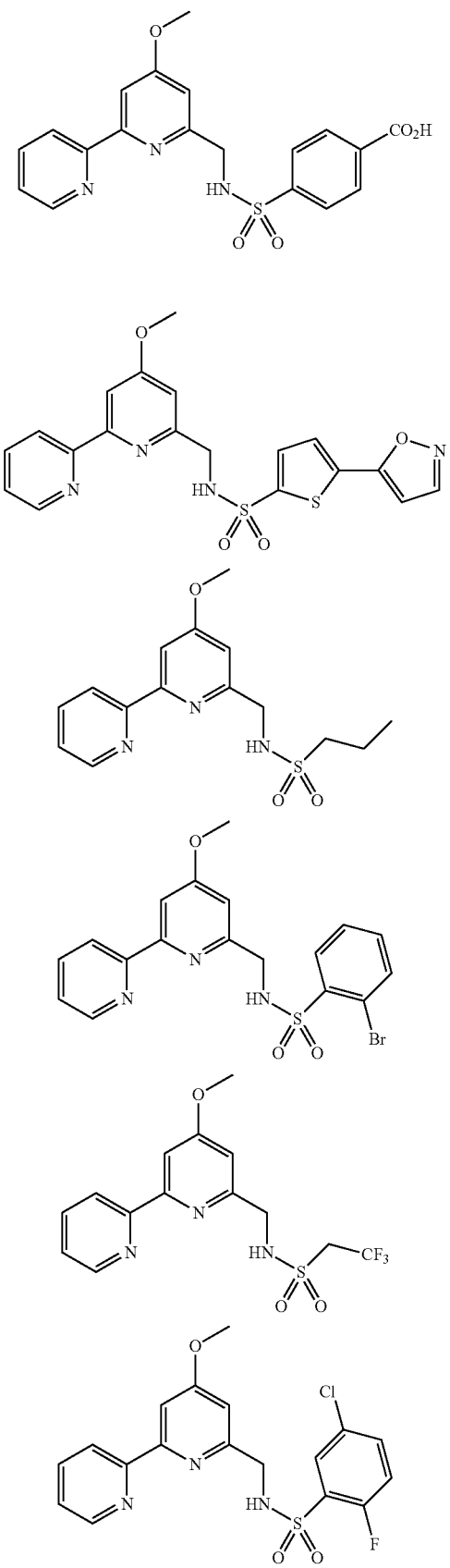

-continued
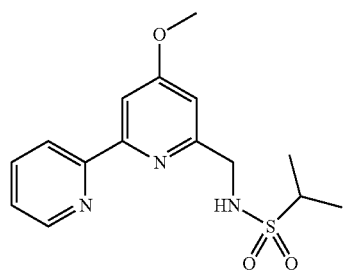
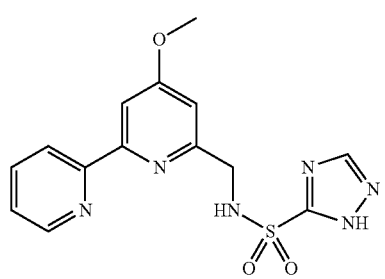
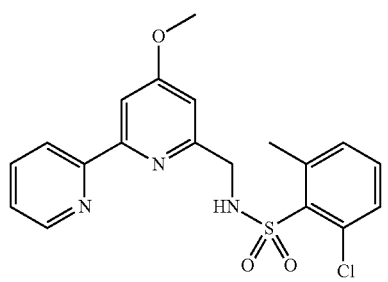
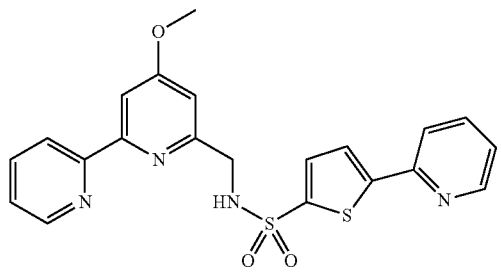
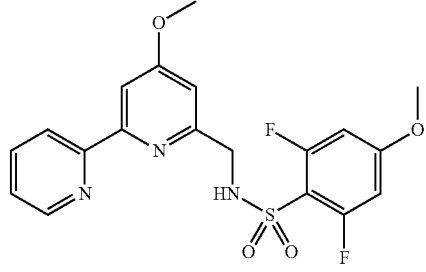
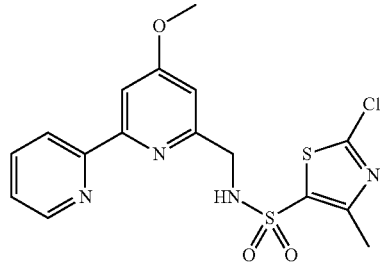
-continued
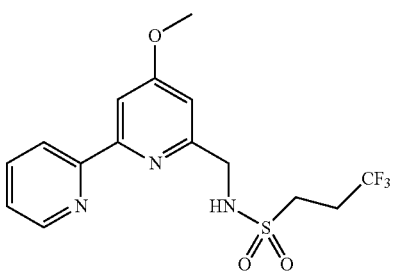
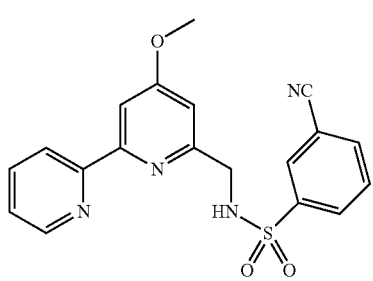
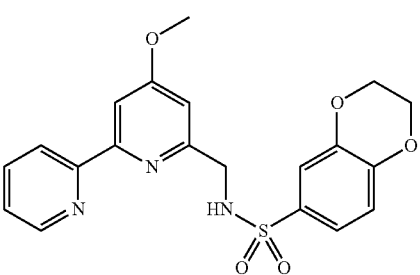
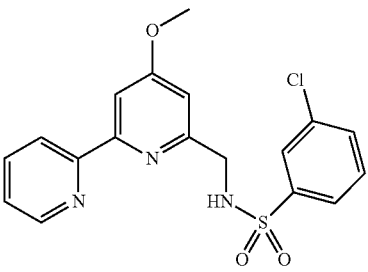
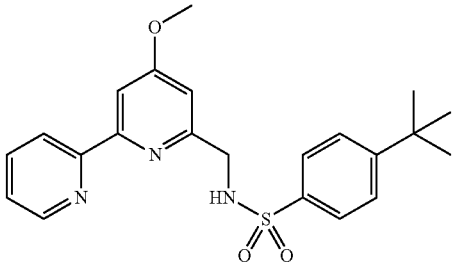
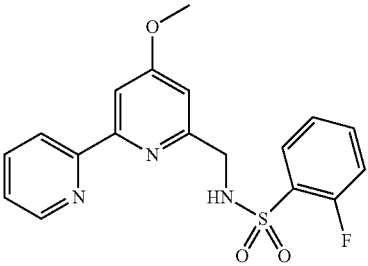

131
-continued
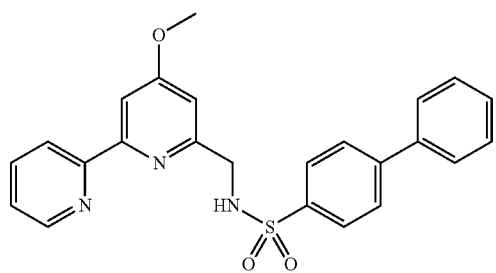
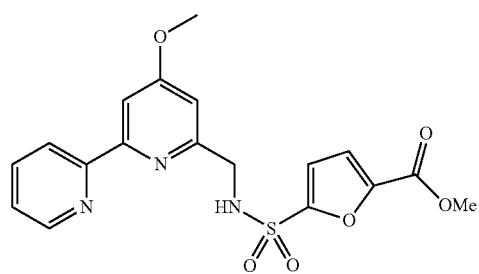
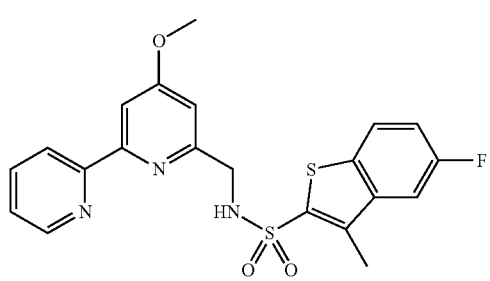
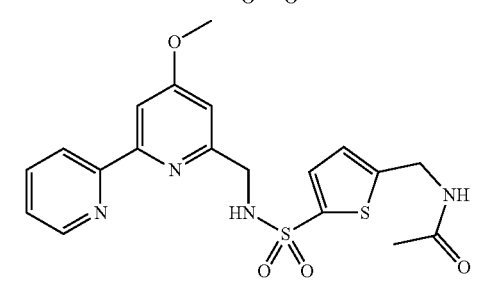
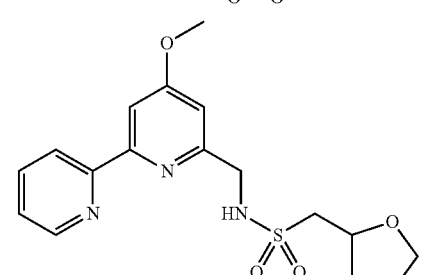
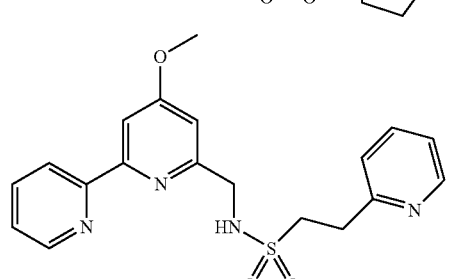
132
-continued
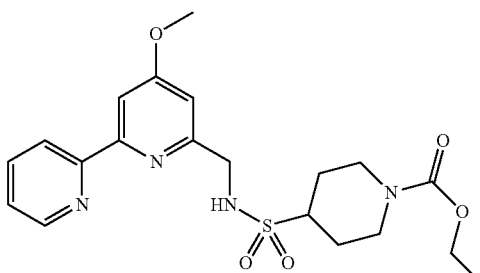
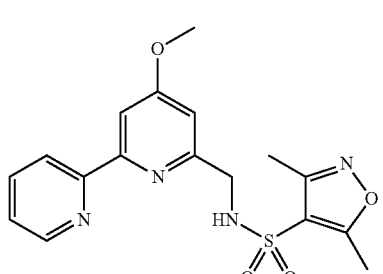
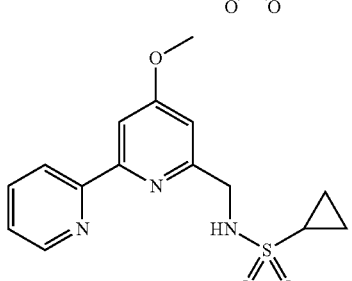
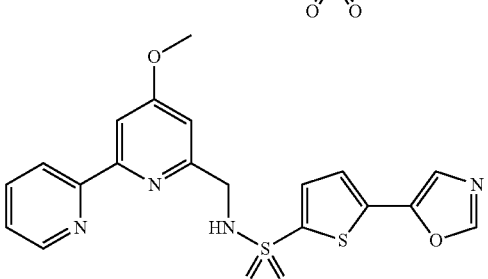
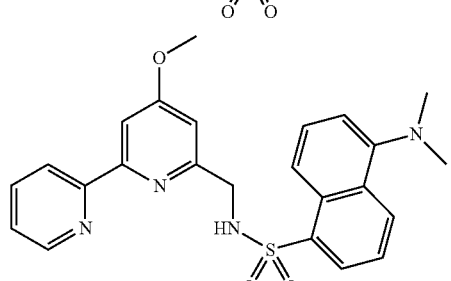
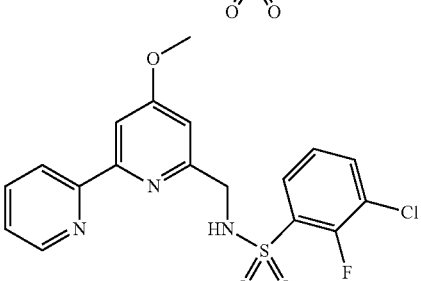

133
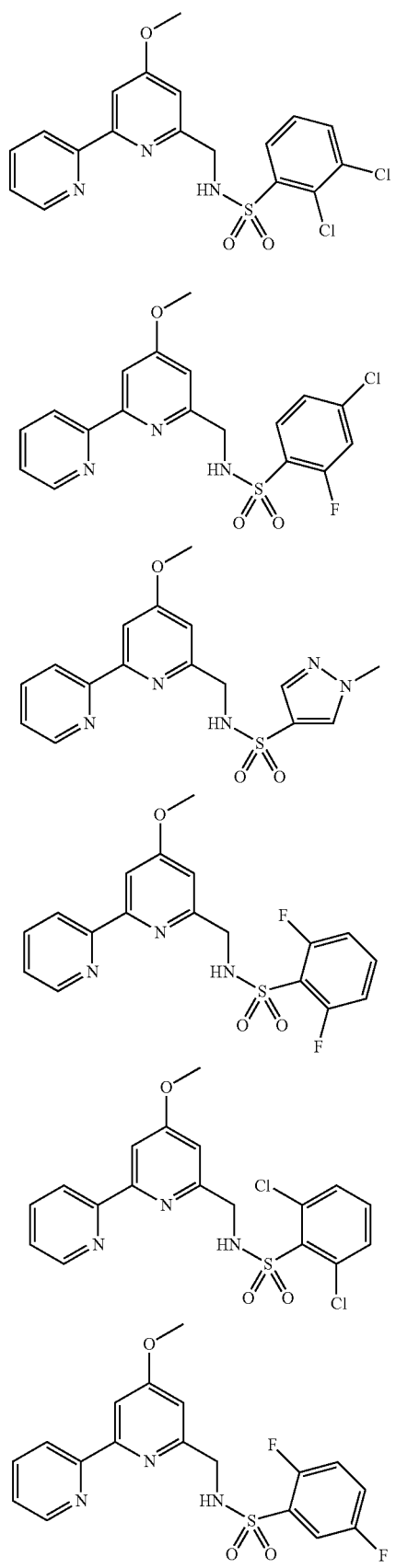
134
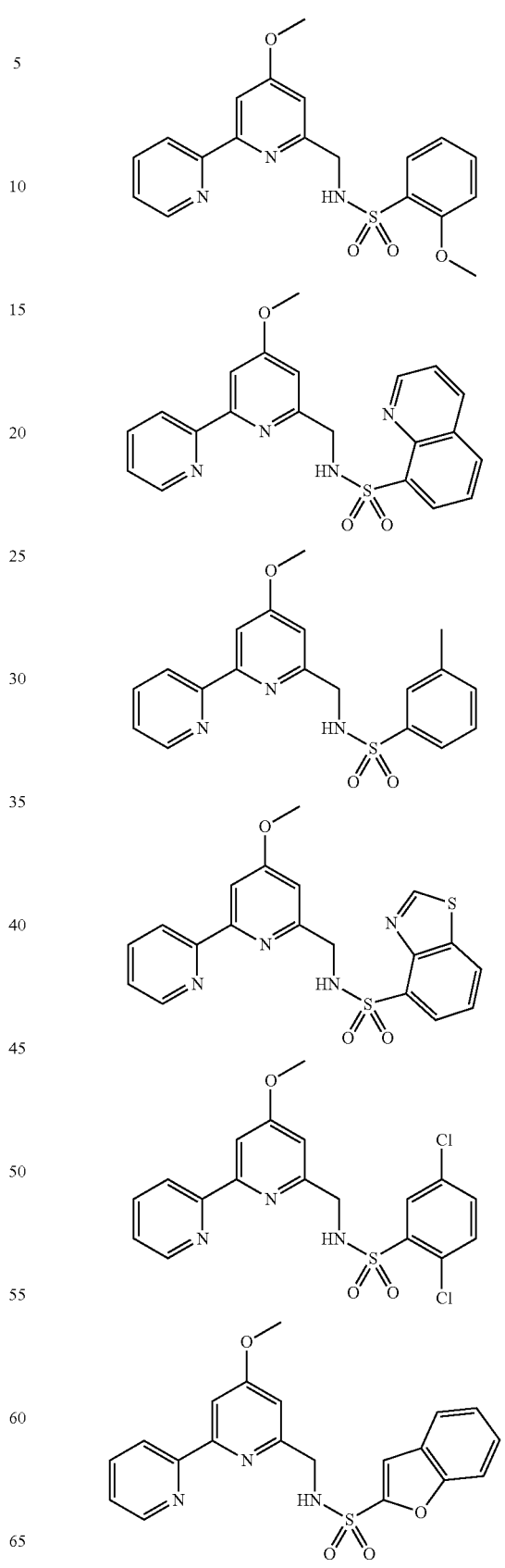

135
-continued
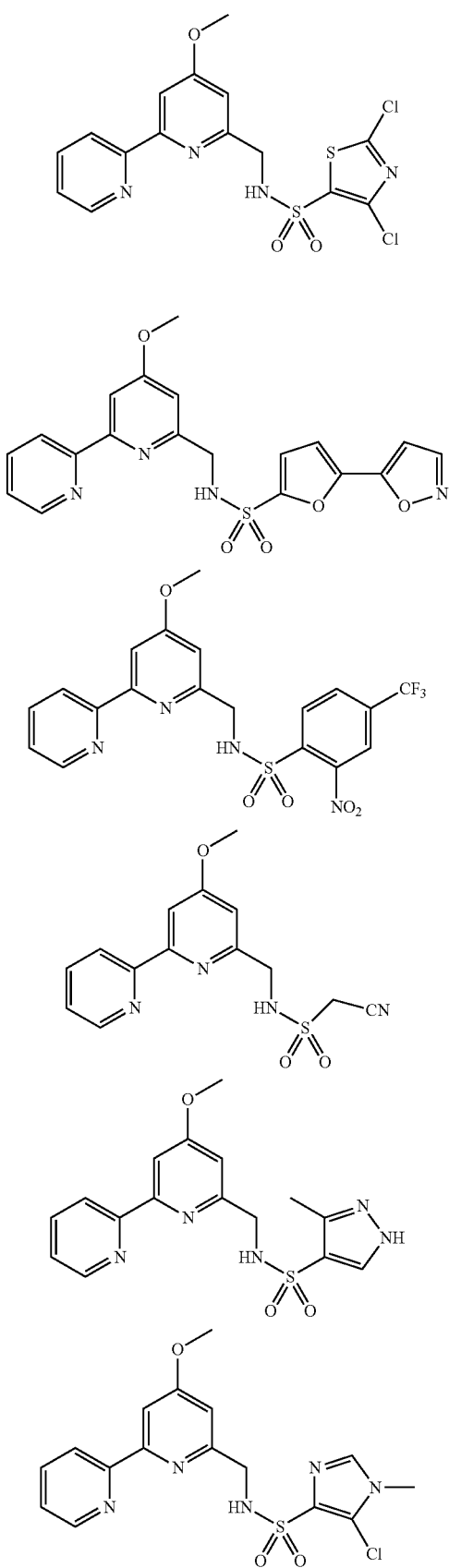
136
-continued
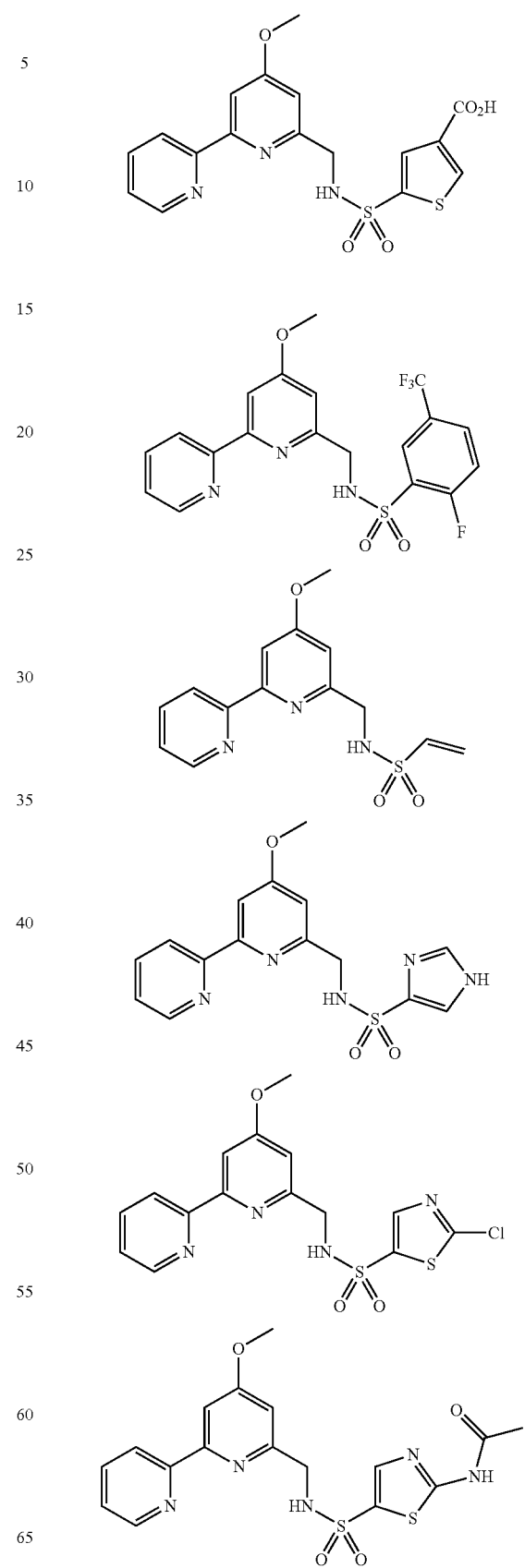

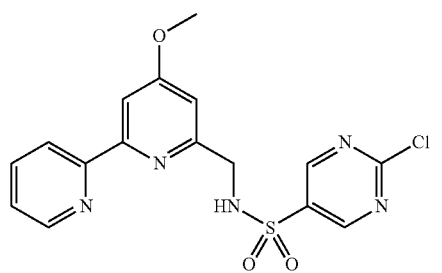
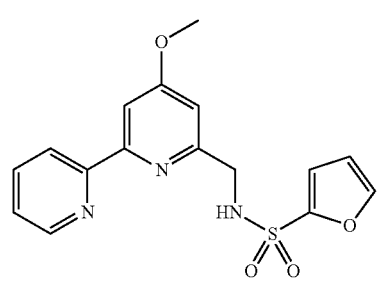
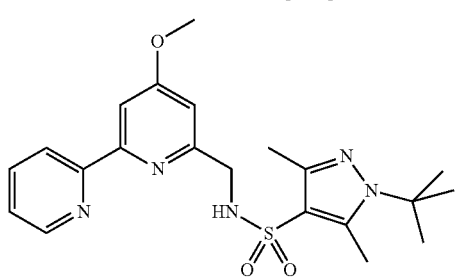
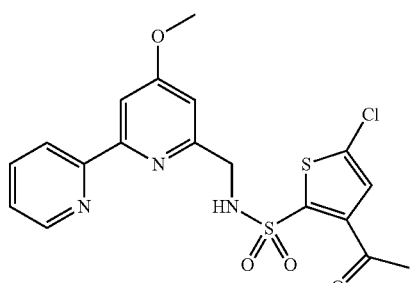
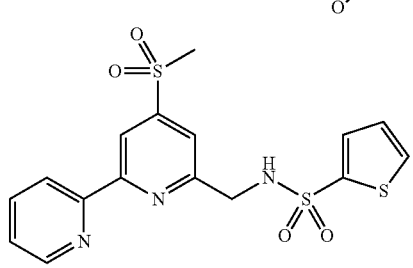
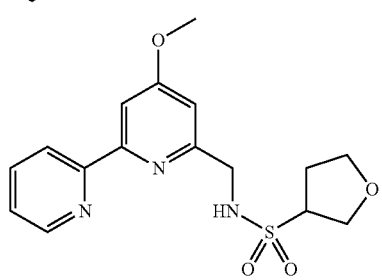
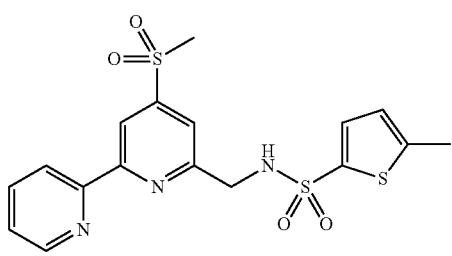
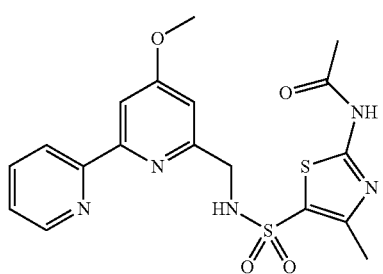
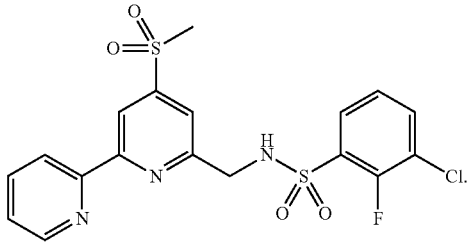
15. A compound according to claim 1, which is:
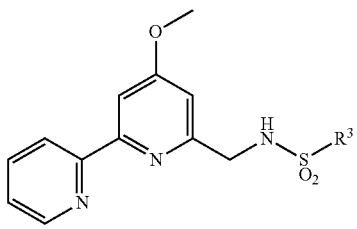
wherein $R^3$ is:
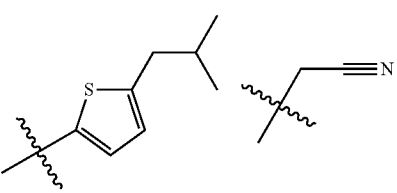
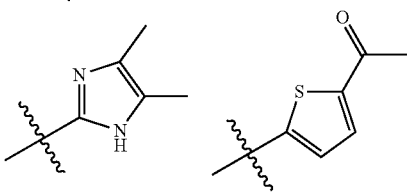

139
-continued
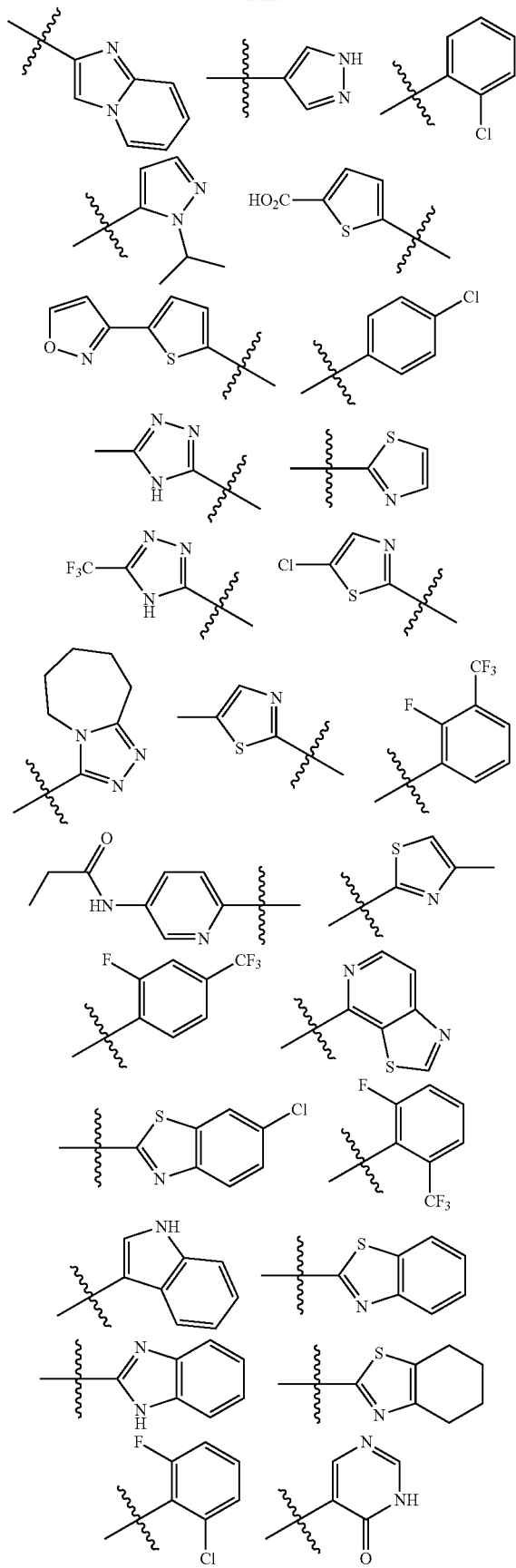
140
-continued
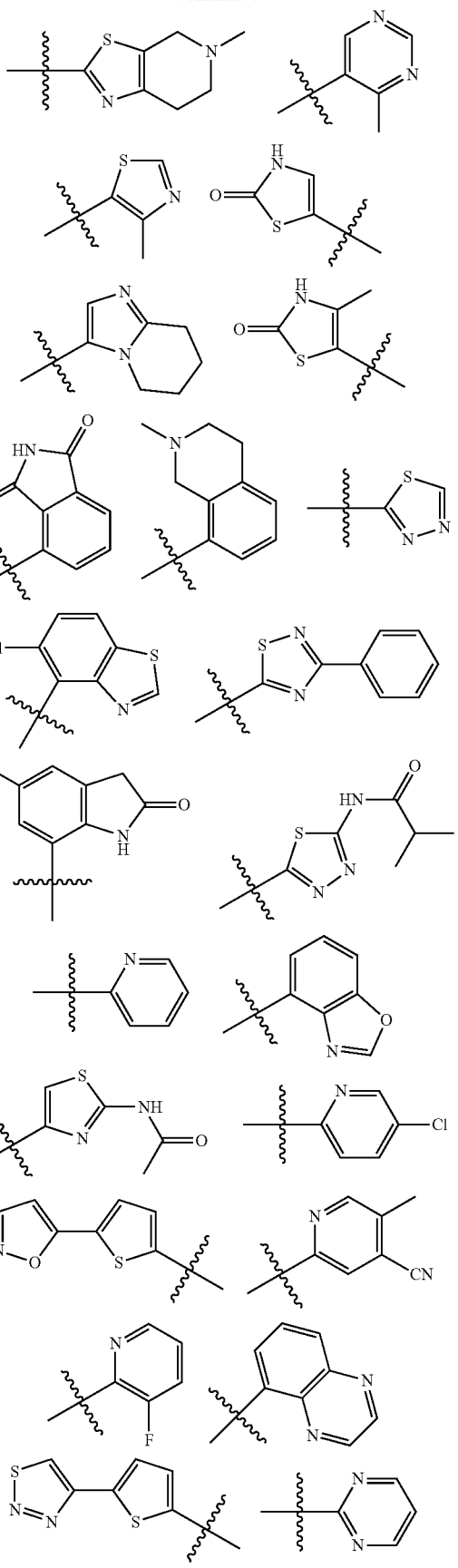

-continued

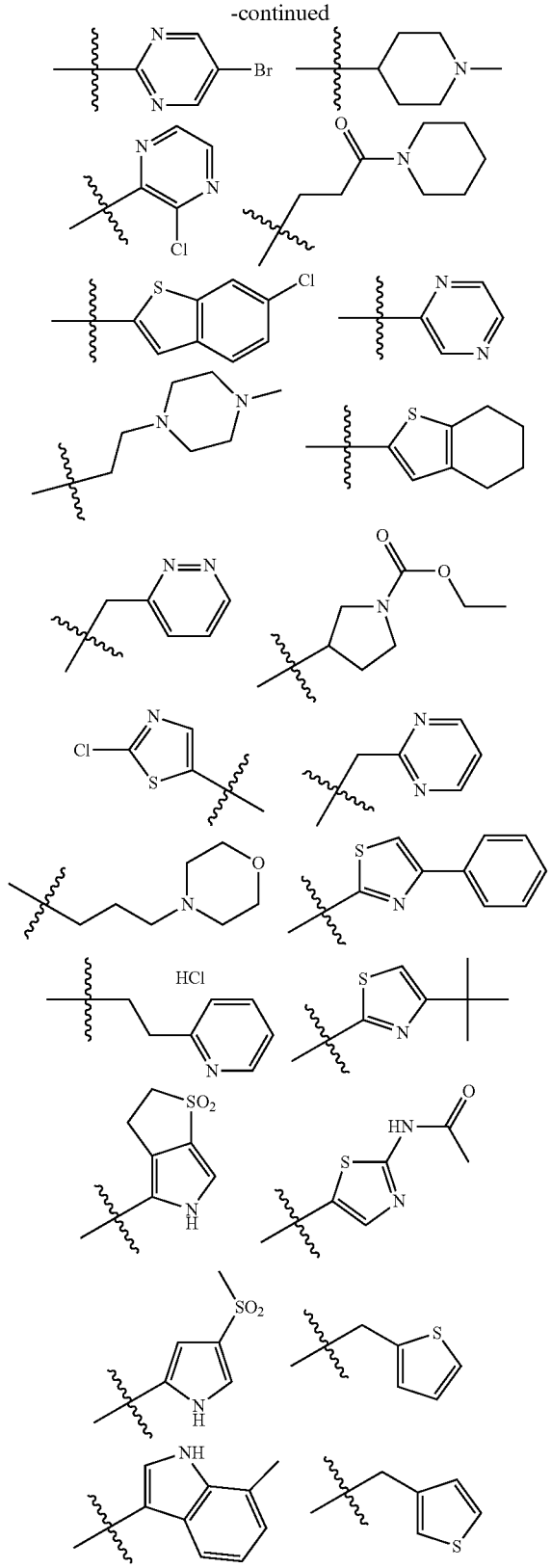

-continued

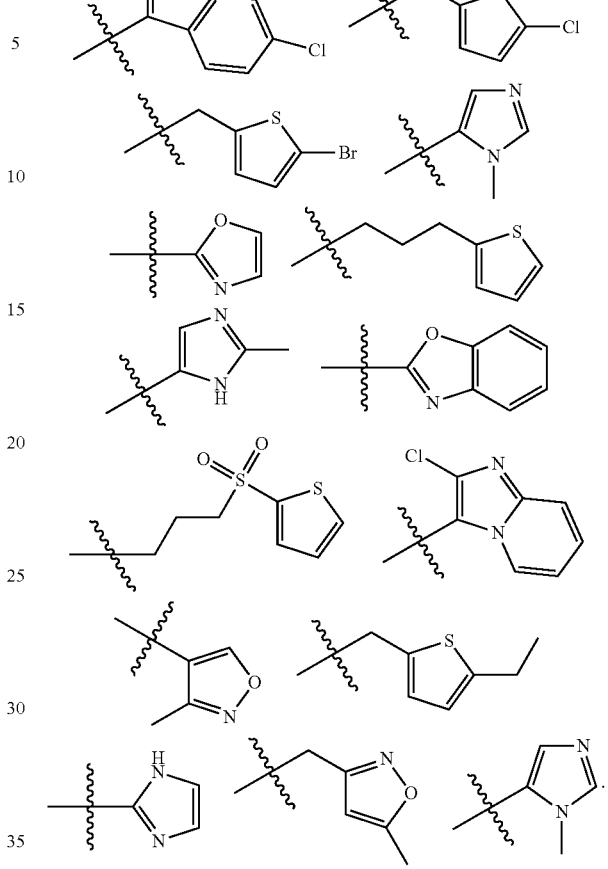

16. A compound according to claim 1, in a pharmaceutical dose form.

17. A pharmaceutical composition comprising at least one of the compounds according to claim 1, or tautomers, salts, solvates or prodrugs thereof, and at least one pharmaceutically acceptable carrier, adjuvant and/or vehicle.

18. A method of preparation of a compound according to claim 1, comprising mixing a compound of formula:

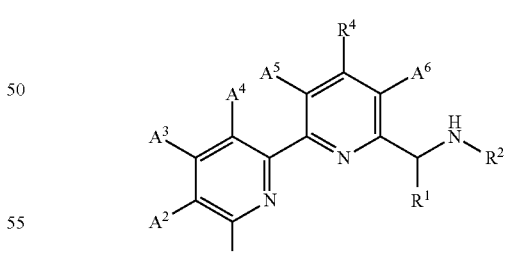

with a sulfonyl chloride of formula $ClSO_2R^3$ in an aprotic or protic solvent, wherein $R^1$-$R^4$ and $A^1$-$A^6$ are as defined in claim 1.

* * * * *

UNITED STATES PATENT AND TRADEMARK OFFICE
CERTIFICATE OF CORRECTION

PATENT NO. : 9,284,296 B2
APPLICATION NO. : 13/988722
DATED : March 15, 2016
INVENTOR(S) : Francisco Palomo Nicolau et al.

Page 1 of 1

It is certified that error appears in the above-identified patent and that said Letters Patent is hereby corrected as shown below:

Specification

Column 22, line 55-65, compound 36:

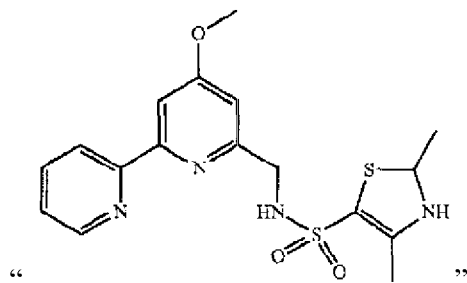

"      "

should be

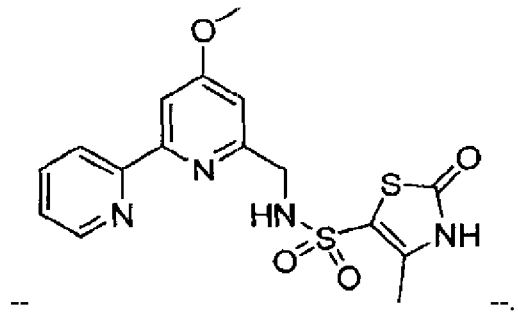

--      --.

Signed and Sealed this
Nineteenth Day of July, 2016

Michelle K. Lee
*Director of the United States Patent and Trademark Office*